(12) United States Patent
Chandler

(10) Patent No.: US 6,592,822 B1
(45) Date of Patent: Jul. 15, 2003

(54) MULTI-ANALYTE DIAGNOSTIC SYSTEM AND COMPUTER IMPLEMENTED PROCESS FOR SAME

(75) Inventor: Van S. Chandler, Austin, TX (US)

(73) Assignee: Luminex Corporation, Austin, TX (US)

( * ) Notice: Subject to any disclaimer, the term of this patent is extended or adjusted under 35 U.S.C. 154(b) by 0 days.

(21) Appl. No.: 09/311,115

(22) Filed: May 13, 1999

Related U.S. Application Data

(60) Provisional application No. 60/085,381, filed on May 14, 1998.

(51) Int. Cl.[7] .................... G01N 21/29; G01N 21/41; G01N 21/00; G01N 33/00; G01N 1/10; G01N 35/00; G01N 21/62; G01N 33/48; G01N 31/00; G01B 5/28; G01B 5/30; G01F 1/00; G01F 7/00; G01F 17/00

(52) U.S. Cl. .................... 422/82.05; 422/68.1; 422/73; 422/100; 422/105; 436/180; 436/43; 436/171; 702/19; 702/21; 702/22; 702/25; 702/27; 702/30; 702/45; 702/49; 356/72; 356/73

(58) Field of Search .................... 422/73, 100, 68, 422/158, 105, 82.05; 436/43, 171, 180; 702/19, 21–23, 25, 27–32, 45, 49, 50; 356/72, 73

(56) References Cited

U.S. PATENT DOCUMENTS

| | | | |
|---|---|---|---|
| 4,284,412 A | 8/1981 | Hansen et al. .................. 23/230 |
| 4,478,088 A | 10/1984 | Loveland .................. 73/861.28 |
| 4,661,913 A | 4/1987 | Wu et al. .................... 364/500 |
| 4,745,285 A | 5/1988 | Recktenwald et al. ... 250/458.1 |
| 5,260,029 A | 11/1993 | Hosoi et al. ............. 422/82.08 |
| 5,299,141 A | 3/1994 | Hungerford et al. ........ 364/510 |
| 5,448,706 A | 9/1995 | Fleming et al. ........ 395/421.07 |
| 5,550,058 A | 8/1996 | Corio et al. .................. 436/63 |
| 5,569,587 A | 10/1996 | Waggoner ...................... 435/6 |
| 5,602,039 A | 2/1997 | van den Engh ............. 436/164 |
| 5,701,012 A | 12/1997 | Ho .......................... 250/461.2 |
| 5,734,422 A | 3/1998 | Maurer et al. .............. 348/184 |
| 5,747,349 A | 5/1998 | van en Engh et al. ...... 436/172 |
| 5,780,865 A | * 7/1998 | Miura et al. |
| 5,824,269 A | 10/1998 | Kosaka et al. ................. 422/73 |
| 5,827,660 A | 10/1998 | Singer et al. .................. 435/6 |
| 5,851,835 A | * 12/1998 | Groner ........................ 436/63 |
| 5,879,628 A | * 3/1999 | Ridgeway et al. ............ 422/73 |
| 5,880,474 A | 3/1999 | Norton et al. ........... 250/458.1 |
| 5,909,278 A | 6/1999 | Deka et al. ................. 356/318 |
| 6,063,339 A | * 5/2000 | Tisone et al. .................. 422/67 |
| 6,133,995 A | * 10/2000 | Kubota ........................ 356/73 |
| 6,190,919 B1 | * 2/2001 | Mastny et al. ................ 436/63 |
| 6,221,671 B1 | * 4/2001 | Groner et al. ................ 436/63 |
| 6,232,125 B1 | * 5/2001 | Deka et al. ................... 436/63 |
| 6,245,572 B1 | * 6/2001 | Wall ............................. 436/63 |
| 6,246,786 B1 | * 6/2001 | Nishikiori et al. .......... 382/184 |
| 6,248,590 B1 | * 6/2001 | Malachowski ............... 436/63 |
| 6,275,777 B1 | * 8/2001 | Shimizu ..................... 702/30 |

* cited by examiner

*Primary Examiner*—Jill Warden
*Assistant Examiner*—Brian R Gordon
(74) *Attorney, Agent, or Firm*—Gilberto M. Villacorta; Robert R. Seabold; Katten Muchin Zavis Rosenman

(57) ABSTRACT

A multi-analyte diagnostic system for use with a computer. The diagnostic system includes a flow analyzer including a co-planar light source-optical detector array, the flow analyzer being communicatable with the computer. The diagnostic system also includes a memory medium readable by the computer and storing computer instructions. The instructions include the following steps. A biological sample is run through the flow analyzer. The identity and quantity of at least one analyte of interest in the biological fluid is determined substantially simultaneously to the sample-running step.

12 Claims, 43 Drawing Sheets

LASER HOUSING 175

DETECTOR HOUSING 185

MULTI-ANALYTE DIAGNOSTIC SYSTEM AND COMPUTER IMPLEMENTED PROCESS FOR SAME

RELATED APPLICATIONS

This application claims priority to U.S. Provisional Application Ser. No. 60/085,381, filed May 14, 1998 and incorporated herein by reference.

FIELD OF THE INVENTION

The present invention pertains generally to a diagnostic system and/or method, and more particularly to a substantially simultaneous and multiplexed, multi-analyte diagnostic system and/or method for performing assays using a flow analyzer.

BACKGROUND OF THE INVENTION

Flow cytometry utilizes an optical technique that analyzes particles in a fluid mixture based on the particles' optical characteristics using a flow cytometer. Background information on flow cytometry is, for example, found in Shapiro, *Practical Flow Cytometry*, Third Ed. (Alan R. Liss, Inc. 1995), incorporated herein by reference.

Conventional flow cytometers have been commercially available since the early 1970s and presently cost, for example, more than $120,000. They can be behemoths in size, occupying upwards of 13 cubic feet and weighing well over 200 pounds.

In conventional flow cytometers, as shown in FIGS. 1 and 2, sample fluid containing sample cells or microspheres having reactants on their surfaces is introduced from a sample tube into the center of a stream of sheath fluid. The sample fluid stream is injected into, at, or near, the center of the flow cell or cuvette. This process, known as hydrodynamic focusing, allows the cells to be delivered reproducibly to the center of the measuring point. Typically, the cells or microspheres are in suspension in the flow cell.

A continuous wave laser 1900 focuses a laser beam on them as they pass through the laser beam by a flow of a stream of the suspension. Lasers in conventional flow cytometers often require shaping a round beam into an elliptical beam to be focused on the flow cell. As shown in FIG. 2, this elliptical beam is often formed from the round beam using a beam shaping prismatic expander 1960 located between the laser and the flow cell.

When an object of interest 1905 in the flow stream is struck by the laser beam, certain signals are picked up by detectors. These signals include forward light scatter intensity and side light scatter intensity. In the flow cytometers, as shown in FIGS. 1 and 2, light scatter detectors 1930, 1932 are located opposite the laser (relative to the cell) to measure forward light scatter intensity, and to one side of the laser, aligned with the fluid-flow/laser beam intersection to measure side scatter light intensity.

In front of the forward light scatter detector 1930 can be an opaque bar 1920, called a beam stop, that blocks incident light from the laser. Thus, the beam stop ensures that as little of the beam as possible will interfere with the measurement by the forward light scatter detector of the relatively small amount of light which has been scattered, by the flow cell, at small angles to the beam. Forward light scatter intensity provides information concerning the size of individual cells, whereas side light scatter intensity provides information regarding the relative size and refractive property of individual cells.

Known flow cytometers, such as disclosed in U.S. Pat. No. 4,284,412 to HANSEN et al., incorporated herein by reference, have been used, for example, to automatically identify subclasses of blood cells. The identification was based on antigenic determinants on the cell surface which react to antibodies which fluoresce. The sample is illuminated by a focused coherent light and forward light scatter, right angle light scatter, and fluorescence are detected and used to identify the cells.

As described in U.S. Pat. No. 5,747,349 to VAN DEN ENGH et al., incorporated herein by reference, some flow cytometers use fluorescent microspheres, which are beads impregnated with a fluorescent dye. Surfaces of the microspheres are coated with a tag that is attracted to a receptor on a cell, an antigen, an antibody, or the like in the sample fluid. So, the microspheres, having fluorescent dyes, bind specifically to cellular constituents. Often two or more dyes are used simultaneously, each dye being responsible for detecting a specific condition.

Typically, the dye is excited by the laser beam from a continuous wave laser 1900, and then emits light at a longer wavelength. As shown in FIG. 1, dichroic filters 1940 split this emitted light and direct it through optical detectors 1950, 1952, 1954 that can be arranged relative to the laser. The optical detectors 1950, 1952, 1954 measure the intensity of the wavelength passed through, respective filter. The fluorescence intensity is a function of the cells' absorption of fluorescent dye.

FIG. 2 depicts a prior art flow cytometer which uses beam splitters 1942, 1944, 1946 to direct light from the flow cell 1910 to photo-multiplier and filter sets 1956, 1958, 1959 and to side light scatter detector 1932. This flow cytometer employs a mirror 1970 to reflect forward light scatter to forward light scatter detector 1930.

However, I have determined that the properties of the fluorescent dyes themselves limit this flow cytometric technique to about three different wavelengths. The difference in energy, and hence wavelength, between an excitation photon and emission photon is known as Stokes shift. Generally, the larger the Stokes shift from the excitation wavelength, the broader and weaker the emission spectra At any given excitation wavelength, I have determined that there are often only a limited number of dyes that emit a spectrum of wavelengths narrow enough and sufficiently separated enough that they are individually measurable simultaneously. Of these, there are fewer dyes still that exhibit good quantum efficiency, for example, between 5and 40%. Other values for quantum efficiency are also acceptable. For example, values of 75 to 80% are acceptable. Consequently, researchers in flow cytometry and other fields have been limited to roughly three fluorescent labels, namely, for green, yellow-orange, and red light.

The limitation on the number of fluorescent labels necessarily crimps the amount of analysis that can be done on any one sample. Therefore, for meaningful analysis, a larger quantity of sample is required and more runs of the sample through the flow cytometer must be performed. This necessarily increases the time needed to analyze the sample. However, time is often not available in an emergency room environment, for example, where a small blood sample, must be screened simultaneously for many diagnostic indicators, including therapeutic and abused drugs, hormones, markers of heart attack and inflammation, and markers of hepatic and renal function. In addition, for efficiency reasons, it is desirable to minimize the testing time to increase the number of tests that can be performed over a predetermined time interval.

One way to overcome the limitation on the number of fluorescent labels, I have determined, is to use two lasers of different frequencies, each focused on a different spot along the flow stream. Such a configuration is called a multi-station flow cytometer. As a particle passes a first laser, up to three fluorescence measurements are taken. Then, as the particle passes the second laser, up to three more measurements are taken using a time-gated amplifier at a predetermined time interval after signals have been detected at the upstream observation point. FIG. 3 illustrates this method.

It should be noted that the upper pair of particles A, B show the lower pair of particles A, B at a later time as the particles progress upward through the flow cell; the particles themselves are the same. In this case, laser #1 strikes particle A. A detector for Laser #2 must wait for a particle to pass through the beam of Laser #2.

Despite this dual laser approach, I have determined that it is often impossible to know for certain whether the measurements are made on the same particle. Because the measurement events at the sets of detectors are separated temporally and spatially, I have discovered that, besides laser emission timing problems, even the slightest flow turbulence can mix particles in suspension, thereby increasing the likelihood that subsequent measurements are not made on the same particle as the previous measurements.

Further, particles in the sample fluid exhibit different velocities as they pass through the flow cell depending on their respective distances from the center of the sample fluid flow stream. Plainly, a an particle closer to the center would travel faster than a particle further away from the center. As such, it is difficult or impossible to be sure exactly when a particle detected by a detector for Laser #1 will pass through a beam of Laser #2.

Referring to FIG. 3, flow turbulence, for example, causes particle B to change places with particle A such that laser #2 strikes particle B, instead of particle A. By extension, this unacceptable problem compounds as lasers and detectors are added to the device.

Despite this flaw, such multiple illumination beam capabilities have been limited to expensive, complex sorters and are not typically found in smaller, less expensive instruments. Besides being large and expensive, such machines are often fully burdened in the clinical setting with CD4–CD8 lymphocyte analysis.

Compounding the above-mentioned shortcomings of existing devices and methods, I have discovered that existing methods of data collection and analysis thereof is tedious, slow, and non-real-time. That is, substantially simultaneous detection of multiple analytes, or of separately identifiable characteristics of one or more analytes, through single-step assay processes is presently not possible, or to the extent possible, has provided limited capability and thus has yielded unsatisfactory results. Reasons for these disappointing results include the following. First, the length of time typically required to enable detection and classification of multiple analytes is unacceptably long. Second, the prior art assays exhibited low analyte sensitivities, which often lead to significant analytical errors and unwieldy collection, classification, and analysis of prior art algorithms relative to large amounts of collected data.

An existing bead set separation method involves the following steps. First, a test tube having sample fluid and sets of reporter beads must be loaded into the flow cytometer and depress the "Acquire" button. Second, when the desired number of data events have been collected, the "Stop" button must be pressed. Third, a file containing the collected data must be saved to a hard drive of a computer. Fourth, a control and analysis software package must be opened. Fifth, the file must be loaded into the control and analysis software package. Sixth, an x-y plot of FL2 v. FL3 must be charted, where FL2 and FL3 are orange and red fluorescence classification parameters for the sets of beads. Seventh, the sets of beads in the plot, represented by clouds of dots, must be visually located and a polygon gate must be drawn around the first set of interest to eliminate stray data points. Eighth, the file must be filtered for events that fall within the polygon gate. Ninth, the statistics must be displayed and the mean value of FL1 must be noted, wherein FL1 is the green fluorescence measurement for the analyte of interest. Tenth, FL1 to FL2 percent spill-over must be calculated and subtracted from the mean value of FL2 to correct the value of FL2. Eleventh, the corrected value of FL2 is used to look up manually which bead set was located in the polygon gate. Twelfth, the FL2 to FL1 percent spill-over is calculated and subtracted from the mean value of FL1. Thirteenth, the assay result is determined from the adjusted value of FL1. The previous thirteen steps are manually repeated for each remaining set of beads.

In addition to the tedium associated with the above-described bead set separation method, I have discovered that the subjectivity associated with estimating the boundaries of the polygon gates is unacceptable. The value of any assay using this method depends largely on the variable judgment of a lab technician. It is often impossible to separate some sets of beads because of overlap of bead regions on the FL2-FL3 plot. Moreover, because of FL1 to FL2 spill-over, the FL2 value of a subset increases sufficiently to overlap with other fluorescence values of other bead sets. Consequently, because of the spill-over, two subsets occupy substantially the same region, making them impossible to distinguish visually there between. The net result of these difficulties is the inability to determine during a sample run, the existence and quantity of an analyte of interest.

In view of the above, I have determined that it would be desirable to have a system and/or method for detecting multiple analytes in a fluid sample by flow cytometric analysis and for analyzing and presenting the data in real-time.

I have determined that it would be desirable to have such a system and/or method, which eliminates the variability of human judgment and subjectivity from the data collection and analysis by performing data collection, bead set classification, and analysis techniques all carried out substantially simultaneously or contemporaneously.

I have also determined that it would be desirable to have such a system and/or method using a flow analyzer that is a fraction of the size, weight, and cost of conventional flow cytometers. That is, I have determined that the current "mainframe-style" flow cytometer must be replaced by a "desktop-style" personal cytometer.

I have further determined that it would be desirable to have such a system that is many times as fast as conventional flow cytometers and yet requires a fraction of the sample volume demanded by the conventional flow cytometers.

I have also recognized a deficiency in the current approach to signal processing in flow cytometry, which uses peak detectors to measure an event. When a peak is found, the peak detectors are disabled while the peaks are measured and processed. "Dead time," the time period during which events can pass through the laser focal point undetected, is highly problematic when the flow cytometer is being used to search for rare events.

Prior art methods, such as U.S. Pat. No. 5,550,058 to Corio et al., incorporated herein by reference, are largely unsuccessful. However, no known prior art method and/or system, including that of Corio et al., has reduced dead time to zero. For example, Corio et al. pre-qualifies an event electronically to reduce the chance that a rare event slips by during dead time. The Corio et al. system sorts particles at a selected yield/purity ratio which ratio can include an intermediate value of the maximum yield and the maximum purity.

Prior art systems and/or methods, which do not use peak detection, use an integrator to measure the area under the pulse. Again, events pass through the laser beam undetected while the measurement is made. Thus, use of an integrator also fails to reduce dead time to zero.

In view of the above-described dead time problem, I have determined that it would be desirable to have a system and/or method for detecting multiple analytes in a fluid sample that reduces dead time in flow analysis to zero.

SUMMARY OF THE INVENTION

It is, therefore, a feature and advantage of the instant invention to provide a system and/or method for detecting multiple analytes in a fluid sample by flow cytometric analysis and for analyzing and presenting the data in real-time.

It is also a feature and advantage of the present invention to provide such a system and/or method, which eliminates the variability of human judgment and subjectivity from the data collection and analysis by performing data collection, bead set classification, and analysis techniques, substantially simultaneously or contemporaneously.

It is another feature and advantage of the instant invention to provide such a system and/or method using a flow analyzer that is a fraction of the size, weight, and cost of conventional flow cytometers. That is, I have determined that to deliver the maximum benefit of the instant diagnostic system to the greatest number of users, the current "mainframe-style" flow cytometer must be replaced by a "desktop-style" personal cytometer.

It is also a feature and advantage of the present invention to provide such a system that is many times as fast as conventional flow cytometers and yet requires a fraction of the sample volume demanded by the conventional flow cytometers.

It is also a feature and advantage of the present invention to provide such a system and/or method that reduces dead time to zero. For example, the system and/or method include constant fixed rate over sampling where signal samples are continuously stored at a predefined interval. By using a second thread to analyze the contents of the circular buffer and process the events, events are never missed, and, hence, there is no dead time.

To this end, it is a feature and advantage of the instant invention to provide a system including a flow analyzer that is approximately one-eighth the size, weight, and cost of most conventional flow cytometers. The system, optionally, is approximately eight times as fast, and, for example, requires one-eighth the sample volume. The system, optionally, is modular to facilitate easy on-site repair and component upgrade. Optionally, it is also controlled by an industry-standard serial or parallel interface, allowing the system to run on a variety of, for example, personal computer environments and to form laptop or desktop factors, under the direction of, for example, a user-friendly graphical user interface.

By achieving the specifications described above, the instant invention provides heretofore uncommon applications for multi-analyte diagnostic systems, ranging from a large clinical laboratory to small point-of-care facility. That is, the speed and technical elegance of the system make it well-suited to, for example, an emergency room environment, where a small blood sample, for example, is screened simultaneously for many diagnostic indicators. Such indicators, for example, include therapeutic and abused drugs, hormones, markers of heart attack and inflammation, and/or those of hepatic and renal function.

The small size, low cost, and quiet operation of the system allows placement thereof in, for example, virtually every blood bank. Donors at such an equipped blood bank can be tested instantly for blood type and transmissible infectious diseases, thereby advantageously avoiding the collection of blood units destined for rejection. Additionally, the small sample volumes processed by the instant system bring the power of multi-analyte testing to, for example, neonatal and pediatric clinics, often advantageously performing complex analyses for less than the cost of a single analyte conventional test.

In an exemplary embodiment, the instant multi-analyte diagnostic system performs real-time bioassays using, for example, multiple classes of microspheres. Each microsphere in a class is coated with a reactant unique to that class. Each class, for example, serves to assay for a respective analyte of interest. Alternatively, more than one class of microspheres, for example, serves to assay for the same analyte of interest. The classes, optionally, are distinguishable by fluorescent labels and/or size so that each class has a respective color and/or size signature. Thus, using the multiple classes of microspheres, multiple analytes, for example, are assayed simultaneously.

The reactants of these assays, for example, are anchored or secured to the surface of the above-mentioned uniquely fluorescent microspheres. Each assay includes at least one microsphere, and preferably up to a thousand or more microspheres. Thus, for example, to conduct one hundred assays, the instant invention includes, for example, one hundred distinguishable classes of microspheres, totaling, for example, 100,000 microspheres. The instant invention, for example, individually analyzes each microsphere in a flow stream at a rate of up to 20,000 or more beads per second, accurately classifying each to its own unique class or subset based on its fluorescent color and/or size signature. Additionally, the instant invention scans each microsphere for the presence of a color, different from those used to provide class signatures, that quantifies the assay occurring at the surface of each microsphere.

By way of illustration, application of the instant invention is, for example, found in an allergist's office. An allergist, for example, screens a patient for various allergic sensitivities. Current methods require that a patient's blood sample be sent from the office to a large clinical laboratory, or that a standard "scratch" test be performed on a patient's skin. Plainly, waiting for blood test results from a large clinical laboratory necessarily limits immediate patient care.

Skin testing patients, using the "scratch" test, is used for suspected immediate-type hypersensitivity to one or more environmental substances. The test is performed by placing a drop of allergen(s) on the skin and making a needle prick through the drop(s) and into the underlying epidermis. Puncture sites are examined over the next 20 minutes for a wheal and flare skin response which, if present, indicates antibody-mediated (IgE) hypersensitivity to the test allergen. The scratch test is subject to an unacceptable rate of false-positives, false-negatives, and limited sensitivity.

In contrast, the instant invention, optionally, incubates, for example, a single drop, or more than a drop, of patient blood for less than fifteen minutes, between fifteen to thirty minutes, or greater than thirty minutes. Then, running the incubated sample through the instant invention in a matter of seconds, the diagnostic system provides a highly accurate, quantitative analysis, and if desired, a qualitative analysis, of hypersensitivity to, for example, the sixty-four allergens simultaneously or substantially simultaneously. In these assays, the reagent or reactant used is, for example, 0.1% or less than that required for a conventional enzyme linked immunosorbent assay (ELISA) format.

More specifically, the instant invention provides a multi-analyte diagnostic system for use with a computer. The diagnostic system, for example, includes a flow analyzer including, a substantially co-planar optical assembly having at least one light source and at least one optical detector. The flow analyzer is, optionally, communicatable with the computer. The diagnostic system, optionally, also includes a memory medium readable by the computer and storing computer instructions. The instructions, for example, include the following sequential, non-sequential, or independent steps. A biological sample, for example, is run through, or processed using, the flow analyzer. An identity and quantity of one or more analytes of interest in the biological sample, for example, is determined substantially simultaneously to the running or processing step. The one or more light sources optionally include a plurality of light sources and the one or more optical detectors optionally include a plurality of optical detectors. The plurality of light sources includes identical, similar, or overlapping focal regions. The plurality of light sources, for example, includes a plurality of laser diodes emitting continuous wave light. The plurality of laser diodes optionally includes laser diodes emitting a plurality of wavelengths of continuous wave light. Optionally, the laser diodes include one or more diode pumped lasers, such as YAG lasers.

The flow analyzer, optionally, includes a cuvette having a flat air-to-glass interface relative to each light source and relative to each optical detector. The cuvette, optionally, includes a cuvette having a hexagonal cross-section. Optionally, the cuvette includes a substantially flat glass-to-fluid interface. The cuvette optionally includes a neck region having one of an internal rectangular cross-section and an internal square cross-section.

The one or more light sources, optionally, include two light sources. Each light source, optionally, emits respective two distinct wavelengths of light. The one or more optical detectors, optionally, includes four optical detectors.

The flow analyzer, optionally, includes a multi-pass filter or a plurality of bandpass filters optically coupled in parallel to one or more optical detectors via a respective multi-mode cable. The flow analyzer, optionally, includes, for each band-pass filter, a standard amplifying photo-detector and a standard analog-to-digital converter connected in series thereto. The amplifying photo-detector includes a standard photomultiplier tube, a standard avalanche photo-diode, or a standard p-i-n photo-diode. The flow analyzer, for example, includes for each band-pass filter, an optional standard inverting amplifier in series with a standard low pass Nyquist filter, connected between the amplifying photo-detector and the analog-to-digital converter.

The flow analyzer, optionally, includes one or more magnification lens for magnifying light emission or reflection from the cuvette. For example, the magnification lens may include a lens having a magnification of up to or more than 15x. Advantageously, the magnification lens obviates use of the above-mentioned multi-mode cable or optical fiber. For example, the flow analyzer optionally-includes a mirror reflecting the light from the cuvette to appropriate detectors.

The diagnostic system optionally includes a digital interface board in the flow analyzer and connectable to the computer via a serial or parallel interface. The digital interface board, optionally, includes a standard microcontroller in communication with the flow analyzer, and a standard digital signal processor in communication with the microcontroller and each analog-to-digital converter. The digital signal processor, optionally, includes a standard circular memory buffer having a first movable pointer, a second movable pointer, and a plurality of storage positions. The first pointer, optionally, points to an oldest storage position into which new sample data can be stored. The second pointer, optionally, points to a storage position from which the digital signal processor is to read the next sample data to be analyzed. The flow analyzer includes a cuvette, a sample pump communicating with the microcontroller and connected to the cuvette, and a sheath fluid reservoir communicating with the microcontroller and connected to the cuvette. The flow analyzer, optionally, includes a waste receptacle. The microcontroller, upon assay completion, optionally, communicates with the sample pump to halt sample fluid flow or divert any remaining sample to the waste receptacle, and, optionally, communicates with the sheath fluid reservoir to halt sheath fluid flow or divert any remaining sheath fluid to the waste receptacle. Optionally, the flow analyzer includes a single-filter light path from each optical detector to each amplifying photo-detector.

The diagnostic system, optionally, further includes a vertically and/or horizontally moveable platform. The flow analyzer, optionally, includes a vertically moveable aspirator. The platform, optionally, cooperates with the aspirator. The platform, optionally, supports a microtiter plate for the flow analyzer.

The instruction for running the instant flow analyzer, optionally, includes exposing a pooled population of subsets of particles to the biological sample, the particles in each subset having (i) one or more classification parameters that distinguish the particles of one subset from those of another subset, and (ii) a reactant specific for each analyte of interest. The running instruction, optionally, further includes passing the exposed pooled population of subsets of particles through an examination zone.

The instruction for determining the identity and quantity of one or more analytes of interest in a biological sample, optionally, includes assessing the identity and quantity of each analyte of interest, if present, in the sample by substantially contemporaneously performing the following steps. Data is, optionally, collected relating to at least one characteristic classification parameter, including data on fluorescence emission intensities. Data is, optionally, collected relating to a presence or absence of a complex formed between the reactant and an analyte of interest specific to the reactant. Without relying exclusively, if at all, on difference's in particle size, each particle is classified according to its subset. An amount of complex associated with each subset is quantified. The step of collecting data relating to a presence or absence of a complex includes collecting analyte data on fluorescence emission intensities. The bead subset data and the analyte data optionally exhibit spectral overlap. The classifying step, optionally, includes reducing the spectral overlap sufficiently to identify each bead according to its subset.

The diagnostic system, optionally, further includes a circular memory buffer communicatable with the flow analyzer. The circular memory buffer optionally includes first movable pointer in operation, pointing to a storage position available for storing new data, and a second movable pointer, in operation, pointing to a storage position having unanalyzed data.

It is also a feature and advantage of the instant invention to provide a cuvette holder. The cuvette holder, optionally, includes a cuvette holder top including one or more optional viewing grooves along one of a diameter and a width of the top. The cuvette holder, optionally, further includes a cuvette holder base for cooperating with the top to hold a cuvette. Optionally, the cuvette holder further includes a base frame. The cuvette holder top is secured to the base frame. The cuvette holder also optionally includes a stability bracket secured to the base frame and securing a top of the cuvette.

It is another feature and advantage of the instant invention to provide a computer program product. The computer program product, for example, includes a memory medium. The computer program product, for example, also includes a computer program stored on the memory medium. The computer program, for example, contains sequential, non-sequential, or independent instructions as follows. A biological sample is run through a flow analyzer. The biological sample includes a pooled population of bead subsets. Each bead subset has one or more characteristic classification parameters. The characteristic classification parameters, for example, includes one or more characteristic fluorescence emission intensities. Substantially contemporaneously to the running step, data related to the at least one characteristic classification parameter, for example, including bead subset data on fluorescence emission intensities is collected. Substantially contemporaneously to the running step, data related to the presence or absence of an analyte of interest, including, for example, analyte data on fluorescence emission intensities is collected. The bead subset data and the analyte data optionally exhibit spectral overlap. Substantially contemporaneously to the running step, the spectral overlap is optionally reduced sufficiently to identify each bead according to its subset.

The computer program optionally includes instructions for determining, substantially contemporaneously to the running step, a presence and quantity of one or more analytes of interest in the biological sample.

The computer program, optionally, further includes instructions for providing a simplex analysis application module and/or a multiplexed analysis application module. The computer program, optionally, further comprises or stores instructions for providing a main menu, a results table, a system monitor, a dot plot display including a density dot plot and/or a decaying dot ploy, a histogram tab, an optical amplifier control tab, a color compensation control tab, and/or a doublet discriminator control tab.

It is also a feature and advantage of the instant invention to provide a computer program product for use with a flow analyzer and a computer. The computer program product includes a memory medium and a computer program stored on the memory medium. The computer program contains the following sequential, non-sequential, or independent instructions. A biological sample is processed using, or run through, a flow analyzer. The biological sample includes a pooled population of bead subsets. Each bead subset has one or more characteristic classification parameters. The one or more characteristic classification parameters includes one or more characteristic fluorescence emission intensities. Substantially contemporaneously to the processing step, data, related to the at least one characteristic classification parameter including bead subset, data on fluorescence emission intensities, is collected. Substantially contemporaneously to said processing step, data, related to a presence or absence of an analyte of interest, including analyte data on fluorescence emission intensities, is collected. Substantially contemporaneously to the processing step, an identify and quantity of at least one analyte of interest in the biological sample is determined. The computer program product also includes an application programming interface library interfacing with the flow analyzer and the computer program, in operation. The computer program further includes a mathematics library communicating with the computer program, in operation.

The application programming interface library optionally includes one or more of the following functions: a function for initializing a device interface for the flow analyzer; a function for closing a device session with a flow analyzer; a function for loading a map file for distinguishing between the bead subsets; a function for defining bead subsets to be associated with an assay; a function for acquiring bead statistics of a selected bead subset; a function for copying flow analyzer settings into a user-supplied buffer; and a function for changing the flow analyzer settings.

The computer program product optionally includes one or more of the following functions: a function for initiating acquisition of bead statistics for a current sample loaded on the flow analyzer; a function for ending the acquisition of bead statistics; a function for copying most current bead statistics into a user-supplied buffer; and a function for one of returning and displaying data acquisition statistics.

It is another feature and advantage of the instant invention to provide a multi-analyte diagnostic method having the following sequential, non-sequential, or independent steps. A biological sample is processed using, or run-through, a flow analyzer. The biological sample includes a pooled population of bead subsets. Each bead subset has one or more characteristic classification parameters. The one or more characteristic classification parameters includes one or more characteristic fluorescence emission intensities. Substantially contemporaneously to the processing step, data, related to the at least one characteristic classification parameter including bead subset data on fluorescence emission intensities, is collected. Substantially contemporaneously to the processing step, data related to a presence or absence of an analyte of interest, including analyte data on fluorescence emission intensities, is collected. The bead subset data and the analyte data exhibit spectral overlap. Substantially contemporaneously to the processing step, the spectral overlap is reduced sufficiently to identify each bead according to its subset. Substantially contemporaneously to the processing step, an identify and quantity of at least one analyte of interest in the biological sample is determined.

It is another feature and advantage of the instant invention to provide a management system. The management system includes a file system storing static portions of substantially all data pages in a data site. The system also includes a server communicatably connected to the file system. The server retrieves the static portions of one or more data pages stored by the file system and transmits to a site user the static portions of one or more data pages.

Optionally, the management system further includes a data page generator generating the static portions of substantially all data pages based on the data site for storage in the file system. The management system further includes a dynamic data transmit device to transmit dynamic data to be cooperatively presented with the static portions as the at least one data page to the site user. Optionally, the data page generator generates the static portions of the substantially all data pages and provides corresponding indexes therewith. Optionally, the server transmits the static portions to the site user responsive to the corresponding index associated with the at least one data page.

It is another feature and advantage of the instant invention to provide a method of managing a data site having the following sequential, non-sequential, or independent steps. Static portions of substantially all data pages in a data site, are stored using a file system. The static portions of at least one data page stored by the file system, are retrieved using a server communicatably connected to the file system. The static portions of the at least one data page, are transmitted to a site user using the server.

Optionally, the static portions of the substantially all data pages based on the data site for storage in the file system, are generated using a data page generator. Optionally, dynamic data to be cooperatively presented with the static portions as the at least one data page to the site user, are transmitted using a dynamic data transmit device. Optionally, the data page generator generates the static portions of the substantially all data pages and provides corresponding indexes therewith. Optionally, the server transmits the static portions to the site user responsive to the corresponding index associated with the at least one data page.

It is another feature and advantage of the instant invention to provide an analysis or diagnostic method, having the following sequential, sequence independent, or non-sequential, steps. A plurality of pooled subsets are processed through an inspection area, each of the plurality of pooled subsets including one or, more indication parameters. Each of the plurality of samples are illuminated, substantially simultaneously and not sequentially, with two or more light beams from one or more sources, at substantially the same time. One or more indication parameters are determined responsive to the illuminating step. Optionally, each of the light beams according to this method includes continuous wave light.

It is another feature and advantage of the instant invention to include a novel flow cytometer including a base section. A plurality of light sources is mounted to the base section. A plurality of selectors is mounted to the base section. A sample viewing chamber is mounted to the base section and in optical relationship with the plurality of light sources and the plurality of detectors.

It is another feature and advantage of the instant invention to include an analysis or diagnostic system. The instant diagnostic system according to this embodiment includes an initialization system initializing a device interface for a flow cytometer, including a termination system terminating a device session for the flow cytometer; a bead map file system loading a file defining a bead map indicative of an associated bead type; a reset system resetting beads to be used in the analysis or diagnostic system; and a user bead component system used to acquire bead statistics for the beads and the associated bead type.

The instant diagnostic system according to this embodiment further includes a machine control and monitoring system, responsively coupled to the initialization system, and monitoring and controlling the analysis or diagnostic system, including: a panel setting system maintaining current flow cytometer settings in a buffer or storage area; and a change panel setting system changing at least one of the current flow cytometer settings responsive to a command.

The instant diagnostic system according to this embodiment also includes a sample acquisition and reporting system, responsively coupled to the machine control and monitoring system, collecting data for analysis or diagnosis, including: a test start system indicating when to begin collecting the data from the machine control and monitoring system; a test stop system indicating when to stop collecting the data from said machine control and monitoring system; a test stop system indicating when to stop collecting the data from said machine control and monitoring system; a test storage system storing the data in another buffer or storage area; and a test query system performing the analysis or diagnosis on the data responsive to a predetermined program or user query.

It is another feature and advantage of the instant invention to include an analysis or diagnostic method having the following independent, sequential, or non-sequential steps. A device interface for a flow cytometer is initialized. The initializing step includes terminating a device session for the flow cytometer; loading a bead map file defining a bead map indicative of an associated bead type; resetting beads to be used in the analysis or diagnostic system; and acquiring bead statistics for the beads and the associated bead type.

An analysis or diagnosis is controlled and monitored using a machine control and monitoring system. The controlling and monitoring step includes: maintaining current flow cytometer settings in a buffer or storage area; and changing at least one of the current flow cytometer settings responsive to a command.

Data is collected for analysis or diagnosis. The data collection step includes: indicating when to begin collecting the data from the machine control and monitoring system; indicating when to stop collecting the data from the machine control and monitoring system; storing the data in another buffer or storage area; and performing the analysis or diagnosis on the data responsive to a predetermined program or user query.

It is another feature and advantage of the instant invention to provide a detector apparatus including a U-block assembly. The detector apparatus includes one or more optical beam splitters and one or more optical detectors secured to the U-block assembly. The detector apparatus further includes one or more push-pull assemblies adjustably securing the one or more optical beam splitters to the U-block assembly, and directing the one or more optical beam splitters to be sufficiently optically couplable with the one or more optical detectors.

Optionally, the U-block assembly includes a unitary or integrated body having an inner portion. The one or more optical beam splitter bordered, in part, by the inner portion of the U-block assembly. The body of the U-block assembly includes first and second legs. The one or more optical detectors are secured within the first leg, and the one or more push-pull assemblies are secured within the second leg. Optionally, the detector apparatus further includes an optical assembly base frame, wherein the U-block assembly is secured thereto. The one or more push-pull assemblies includes a screw tap and spring assembly for pushing a side of the one or more beam splitters toward the one or more optical detectors, and/or pulling another side of the one or more beam splitters away from the one or more optical detectors.

Optionally, the one or more optical beam splitters includes one or more dichroic mirrors. The one or more dichroic mirrors includes a plurality of dichroic mirrors. Each dichroic mirror directs a respective band of wavelengths of light to a respective optical detector and transmitting a remainder of wavelengths of light therethrough. Optionally, the detector apparatus further comprises one or more filters, interposed between the one or more optical beam splitters and the one or more optical detectors.

It is also a feature and advantage of the instant invention to provide, in a flow analyzer including a pressure sensor and a sheath fluid reservoir, a de-bubbler. The novel de-bubbler includes a bottle including an upper portion and a lower portion. The upper portion of the bottle includes an inlet operatively connected to the sheath fluid reservoir to receive sheath fluid therefrom. The lower portion of the bottle includes an outlet operatively connected to the pressure sensor. The bottle further includes a substantially waterproof vent sealing a top of the bottle and exposing an interior of the bottle to an atmosphere external to the bottle so that, in operation, sheath fluid is output via the outlet substantially free of a gas bubble.

Optionally, the flow analyzer further includes a sample pump. The pressure sensor optionally transmits a command to deactivate the sample pump upon sensing a decreased fluid pressure in the de-bubbler.

It is another feature and advantage of the instant invention to provide a multi-analyte diagnostic system for analyzing a sample fluid for one or more analytes of interest. The multi-analyte diagnostic-system includes a flow analyzer, which includes a cuvette including, in operation, a fluid core, and including a neck region having a substantially flat glass-to-fluid interface and a substantially flat air-to-glass interface. The flow analyzer also includes a first magnification lens optically cooperative with the cuvette and having a magnification power. The flow analyzer further includes a filter and optical amplifier assembly including an entrance aperture. The entrance aperture is dimensioned to cooperate with the magnification power to transmit light from the fluid core in the cuvette with substantially no light distortion from the glass-to-fluid interface and/or the air-to-glass interface.

Optionally, the flow analyzer is communicatable with a computer. The multi-analyte diagnostic system optionally includes a memory medium readable by the computer and storing computer instructions executed by the computer. The computer instructions include processing the sample fluid using said flow analyzer, and analyzing the sample fluid and determining a presence and quantity of at least one analyte of interest in the sample fluid substantially simultaneously to the processing step.

Optionally the multi-analyte diagnostic system further includes a first mirror optically coupled to the first magnification lens and reflecting a first plurality of wavelengths of the light to the entrance aperture, at least one of the first plurality of wavelengths indicative of a presence of one or more analytes of interest in the sample fluid.

Optionally, the flow analyzer further includes one or more light sources to radiate the cuvette. The one or more light sources include a laser diode and/or a diode pumped laser.

Optionally, the cuvette includes upper and lower portions. Optionally, the multi-analyte diagnostic system further includes an optical assembly base frame. The first magnification lens, the filter and optical amplifier assembly, and the one or more light sources are secured to the optical assembly base frame. The multi-analyte diagnostic system further includes a cuvette holder secured to the optical assembly base frame and securing a bottom of the cuvette. The diagnostic system also includes an optional stability bracket secured to the optical assembly base frame and securing a top of the cuvette.

Optionally, the multi-analyte diagnostic system further includes a second magnification lens optically cooperative with the cuvette. The diagnostic system optionally includes one or more optical beam splitters optically cooperative with the second magnification lens. The diagnostic system optionally includes one or more optical detectors identifying one or more particles as belonging to a respective particle subset, and optically cooperative with the one or more optical beam splitters.

Optionally, the multi-analyte diagnostic system further includes a second mirror optically coupled to the second magnification lens and the one or more beam splitters. The second mirror reflects a second plurality of wavelengths of light to the one or more optical beam splitters. One or more of the second plurality of wavelengths are indicative of the identity of the one or more particles.

Optionally, the multi-analyte diagnostic system further includes a side scatter optically cooperating with the one or more beam splitters and identifying a doublet.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the. U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

NOTATIONS AND NOMENCLATURE

The detailed descriptions which follow may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

BRIEF DESCRIPTION OF THE DRAWINGS

FIG. 37 is an illustrative embodiment of a bead details graphical display window;

BEST MODE FOR CARRYING OUT THE INVENTION

Generally, the instant multi-analyte diagnostic system performs on a biological sample, bioassays including, for example, immunoassays, complex genetic analyses, and enzymatic assays. To this extent and others U.S. application Ser. No. 08/540,814 to Van S. Chandler et al. is incorporated herein by reference in its entirety.

The biological sample to be tested using the instant invention, for example, includes plasma, serum, tears, mucus, saliva, urine, pleural fluid, spinal fluid, gastric fluid, sweat, semen, vaginal secretion, fluid from ulcers and/or other surface eruptions, blisters, abscesses, and/or extracts of tissues, such as biopsies of normal, malignant, and/or suspect tissues.

The analytes of interest for these bioassays include, for example, antigens, antibodies, autoantibodies, peptides, proteins, nucleic acid sequences, and/or enzymes. The antigenic analytes, for example, includes bacterial, viral, fungal, mycoplasmal, ridkettsial, chlamydial, and/or protozoal antigens. Alternatively, the antigens, for example, include antigens borne by pathogenic agents responsible for a sexually transmitted disease, antigens borne by pathogenic agents responsible for a pulmonary disorder, and/or antigens borne by pathogenic agents responsible for gastrointestinal disorder.

The analyte of interest, for example, includes a substance of abuse or a therapeutic drug. The analyte of interest, for example, includes an antigen or antibody associated with a pathological syndrome, such as cardiovascular disorders, malignancy, allergy, autoimmune diseases, and/or blood-borne viruses. The analyte, for example, is an indicator for pregnancy or specific hormones.

The enzymatic analytes includes, for example, proteases, glycosidases, nucleotidases, oxidoreductases, hydrolases, esterases, convertases, ligases, transferases, phosphorylases, lyases, lipases, peptidases, dehydrogenases, oxidases, phospholipases, invertases, aldolases, transaminases, synthetases, and/or phosphotases.

Figure 1:
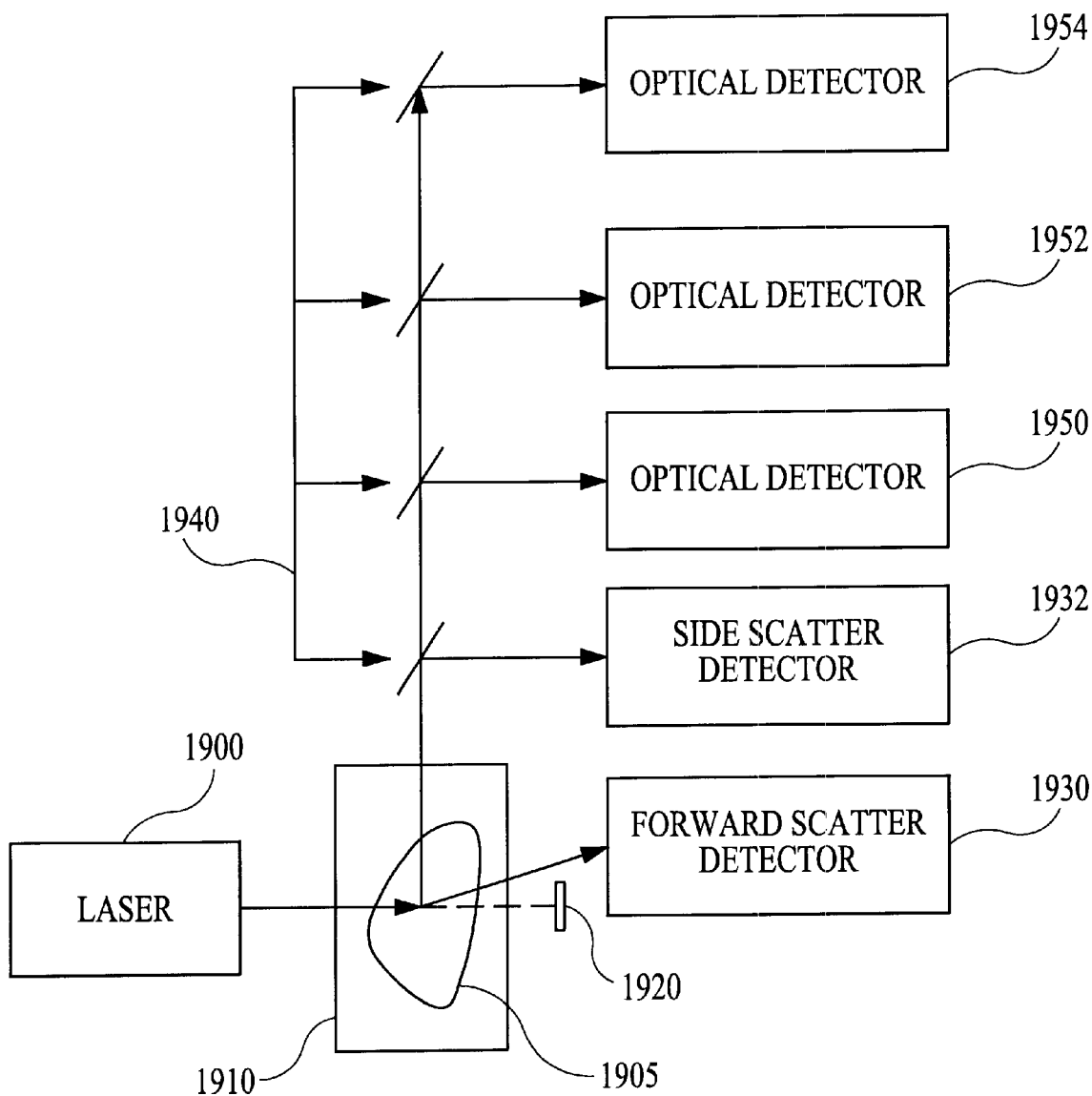
FIG. 1 is a schematic of a prior art flow cytometer.
Figure 2:
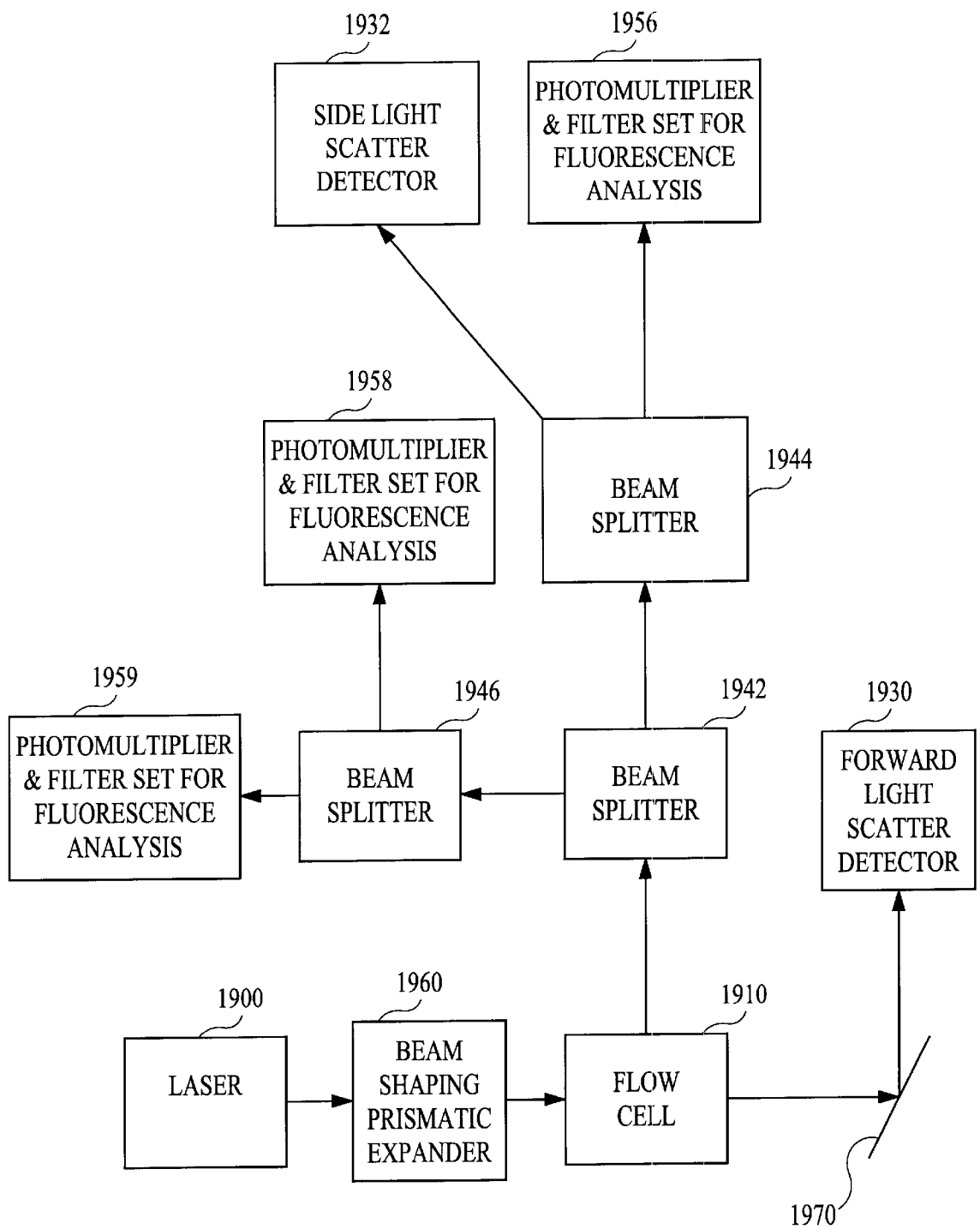
FIG. 2 is a schematic of a prior art flow cytometer.
Figure 3:
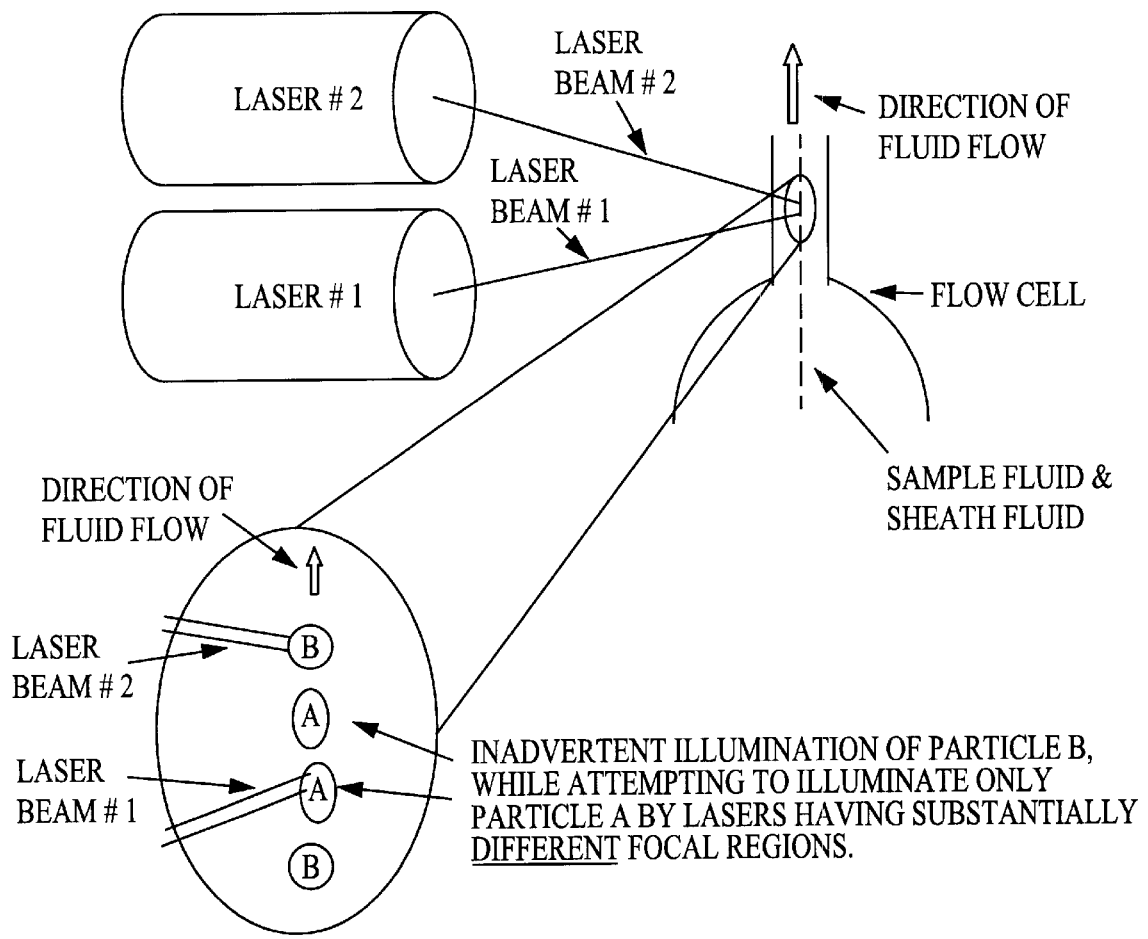
FIG. 3 is a schematic showing operation of a flow cytometer.
Figure 4:
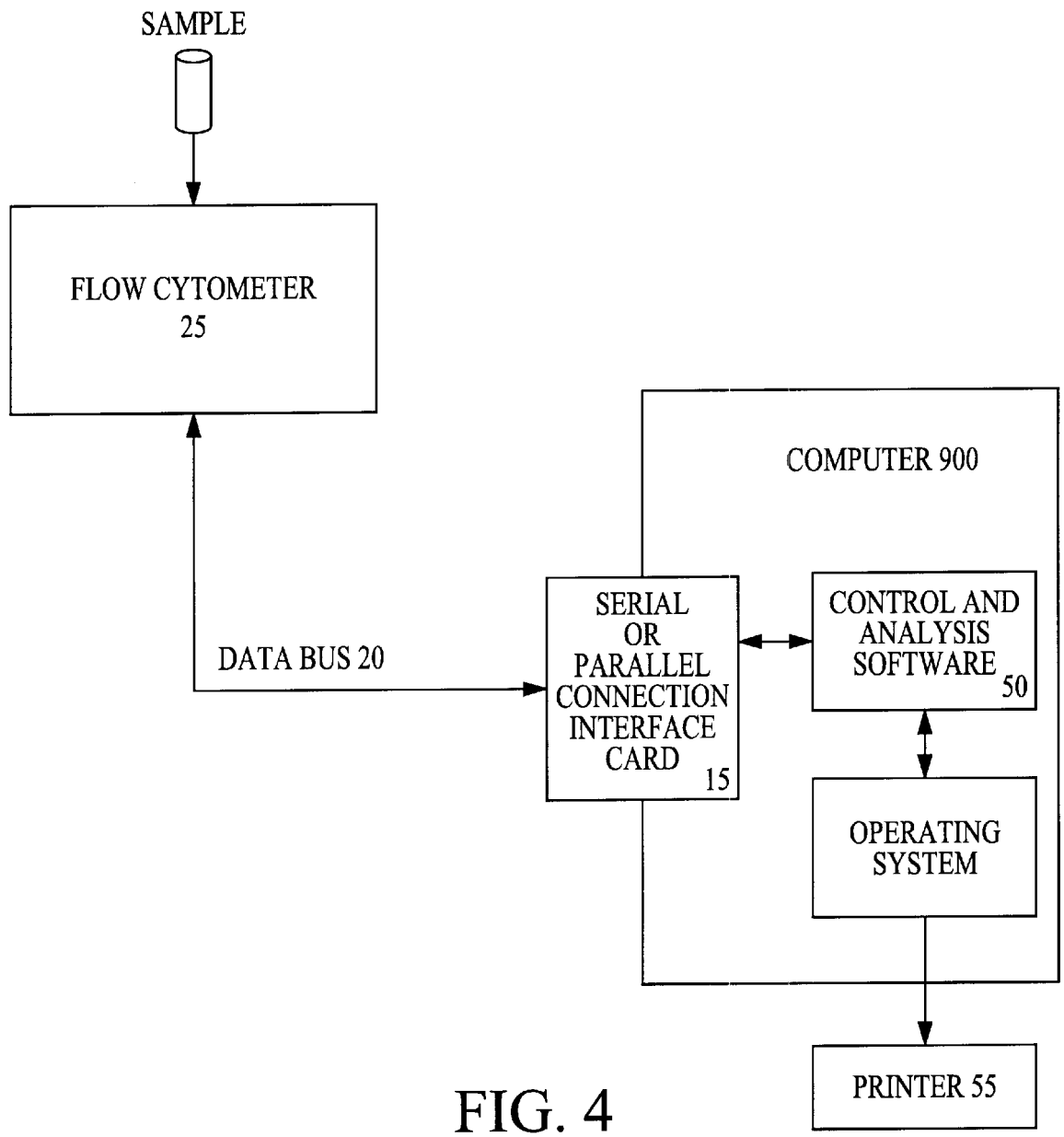
FIG. 4 is a general schematic of an illustrative embodiment of the instant diagnostic system.

As shown in FIG. 4, the system components of the instant invention include a flow analyzer 25, such as a flow cytometer, and a cooperative control and analysis software package 50. Hardware components for use with the instant invention, for example, include a power source, interface cable, and/or a standard computer. Consumables for use of the instant invention, for example, include microliter tubes, for example, of 1 mL each, sheath fluid, and microspheres. Optional components, for example, include, for example, a standard spreadsheet software package cooperatively linked to the control and analysis software of the instant invention.

The microspheres are alternately termed microparticles, beads, polystyrene beads, microbeads, latex particles, latex beads, fluorescent beads, fluorescent particles, colored particles and colored beads. The microspheres serve as vehicles for molecular reactions. Microspheres for use in flow cytometry are obtained from manufacturers, such as Luminex Corp. of Austin, Tex. Illustrative microspheres and methods of manufacturing same are, for example, found in U.S. patent application Ser. No. 09/234,841 to Mark B. Chandler and Don J. Chandler, entitled Microparticles with Multiple Fluorescent Signals, and in U.S. patent application Ser. No. 09/172,174 to Don J. Chandler, Van S. Chandler, and Beth Lambert, entitled Precision Fluorescently Dyed Particles and Methods of Making and Using Same, both patent applications incorporated herein by reference in their entirety. By way of example, if a user were performing an Ig G, A, M Isotyping Assay, the user opts for bead sets, such as Luminex 8070 IgG, 8060 IgA, and 8050 IgM bead sets.

Preferably, the microspheres used according to the instant invention include a pooled population of classes or subsets of microspheres. Each subset of microspheres includes one, two, or more microspheres. Advantageously, a plurality of microspheres per subset are used, for example, up to 1000 or more. Each microsphere in a respective subset of microspheres includes one, two, three, four, five or more classification parameters. For example, one classification parameter includes a forward light scatter, parameter, and another includes a side light scatter parameter.

The classification parameters of each microsphere advantageously includes one, two, three, or more standard fluorochromes or fluorescent dyes. The one or more fluorochromes are affixed to or embedded in each microsphere by any standard method, for example, by attachment to the microsphere surface by covalent bonding or adsorption. Alternatively, the dye(s) may be affixed by a copolymerization process, wherein monomers, such as an unsaturated aldehyde or acrylate, are allowed to polymerize in the presence of a fluorescent dye, such as fluoroscein isothiocynate (FITC), in the resulting reaction mixture.

Another method by which one or more dyes are embedded in a microsphere includes adding a subset of microspheres to for example an organic solvent to expand the microspheres. An oil-soluble or hydrophobic dye, for example, is subsequently added to the subset of microspheres, thereby penetrating into each microsphere. After incubating the resulting combination, an alcohol or water-based solution, for example, is added to the combination and the organic solvent is removed. The microsphere shrinks, retaining the dye(s) inside. Each fluorochrome in the microsphere optionally serves as an additional or alternative classification parameter.

The microsphere classes include respective reporter substances such as antibodies, antigens, peptides, proteins, enzymes and/or nucleic acid probes to provide. specific signals for each reaction in a multiplexed assay. Each reporter substance is selected to react, optionally uniquely, to an analyte of interest in a biological sample.

Figure 39:
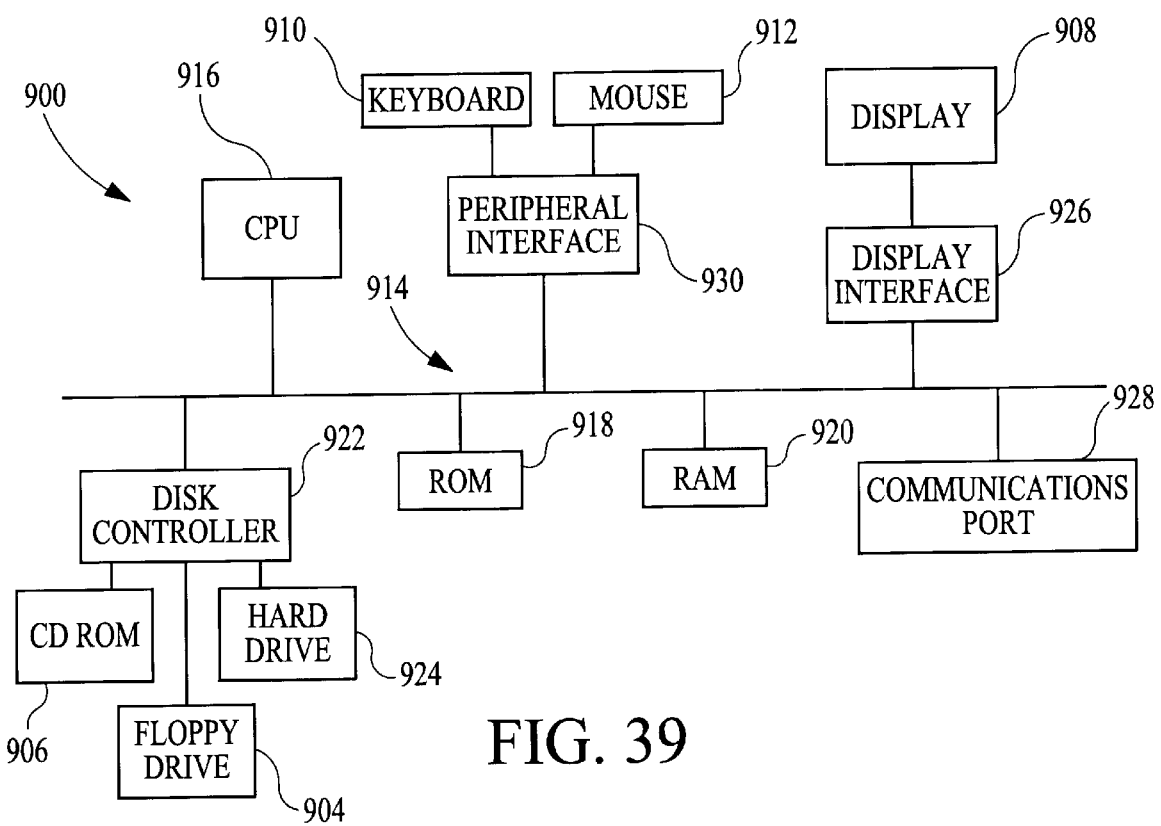
FIG. 39 is an illustrative embodiment of computer architecture consistent with the instant invention.

FIG. 39 is an illustration of a main central processing unit for implementing the computer processing in accordance with a computer implemented embodiment of the present invention. The procedures described herein are presented in terms of program procedures executed on, for example, a computer or network of computers.

Viewed externally in FIG. 39, a computer system designated by reference numeral 900 has a computer 902 having disk drives 904 and 906. Disk drive indications 904 and 906 are merely symbolic of a number of disk drives which might be accommodated by the computer system. Typically, these would include a floppy disk drive 904, a hard disk drive (not shown externally) and a CD ROM indicated by slot 906. The number and type of drives varies, typically with different computer configurations. Disk drives 904 and 906 are in fact optional, and for space considerations, are easily omitted from the computer system used in conjunction with the production process/apparatus described herein.

The computer system also has an optional display 908 upon which information is displayed. In some situations, a keyboard 910 and, a mouse 902 are provided as input devices to interface with the central processing unit 902 Then again, for enhanced portability, the keyboard 910 is either a limited function keyboard or omitted in its entirety. In addition, mouse 912 optionally is a touch pad control device, or a track ball device, or even omitted in its entirety as well. In addition, the computer system also optionally includes at least one infrared transmitter and/or infrared received for either transmitting and/or receiving infrared signals, as described below.

Figure 38:
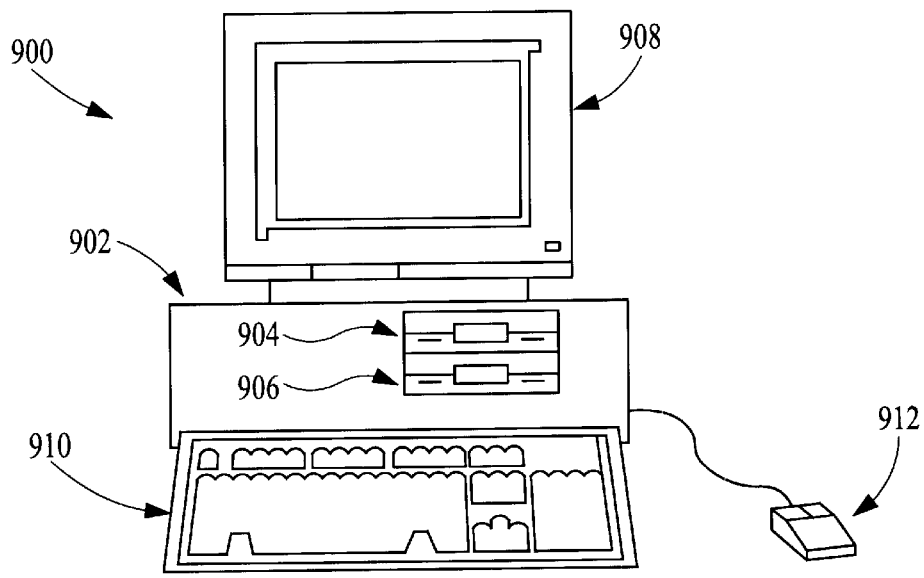
FIG. 38 is an illustrative embodiment of a computer and assorted peripherals.

FIG. 39 illustrates a block diagram of the internal hardware of the computer, system 900 of FIG. 38. A bus 914 serves as the main information highway interconnecting the other components of the computer system 900. CPU 916 is the central processing unit of the system, performing calculations and logic operations required to execute a program. Read only memory (ROM) 918 and random access memory (RAM) 920 constitute the main memory of the computer. Disk controller 922 interfaces one or more disk drives to the system bus 914. These disk drives are, for example, floppy disk drives such as 904, or CD ROM or DVD (digital video disks) drive such as 906, or internal or external hard drives 924. As indicated previously, these various disk drives and disk controllers are optional devices.

A display interface 926 interfaces display 908 and permits information from the bus 914 to be displayed on the display 908. Again as indicated, display 908 is also an optional accessory. For example, display 908 could be substituted or omitted. Communications with external devices, for example, the components of the apparatus described herein, occurs utilizing communication port 928. For example, optical fibers and/or electrical cables and/or conductors and/or optical communication (e.g., infrared, and the like) and/or wireless communication (e.g., radio frequency (RF), and the like) can be used as the transport medium between the external devices and communication port 928. Peripheral interface 930 interfaces the keyboard 910 and the mouse 912, permitting input data to be transmitted to the bus 914.

In addition to the standard components of the computer, the computer also optionally includes an infrared transmitter and/or infrared receiver. Infrared transmitters are optionally utilized when the computer system is used in conjunction with one or more of the processing components/stations that transmits/receives data via infrared signal transmission. Instead of utilizing an infrared transmitter or infrared receiver, the computer system optionally uses a low power radio transmitter and/or a low power radio receiver. The low power radio transmitter transmits the signal for reception by components of the production process, and receives signals from the components via the low power radio receiver. The low power radio transmitter and/or receiver are standard devices in industry.

Figure 40:
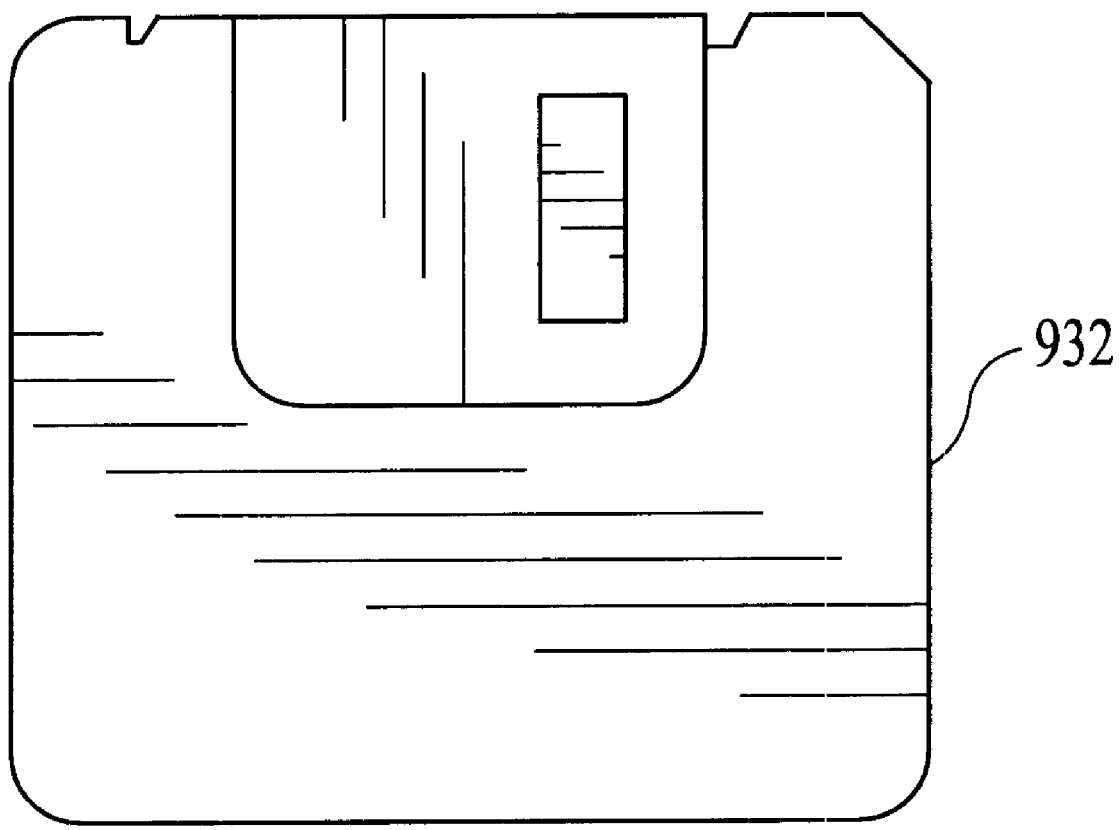
FIG. 40 is an illustrative embodiment of a memory medium.

FIG. 40 is an illustration of an exemplary memory medium 932 which can be used with disk drives illustrated in FIGS. 38 and 39. Typically, memory media such as floppy disks, or a CD ROM, or a digital video disk will contain, for example, a multi-byte locale for a single byte language and the program information for controlling the computer to enable the computer to perform the functions described herein. Alternatively, ROM 918 and/or RAM 920 illustrated in FIGS. 38 and 39 can also be used to store the program information that is used to instruct the central processing unit 916 to perform the operations associated with the production process.

Although computer system 900 is illustrated having a. single processor, a single hard disk drive and a single local memory, the system 900 is optionally suitably equipped with any multitude or combination of processors or storage devices. Computer system 900 is, in point of fact, able to be replaced by, or combined with, any suitable processing system operative in accordance with the principles of the present invention, including sophisticated calculators, and hand-held, laptop/notebook, mini, mainframe and super computers, as well as processing system network combinations of the same.

Conventional processing system architecture is more fully discussed in *Computer Organization and Architecture*, by William Stallings, MacMillan Publishing Co. (3rd ed. 1993); conventional processing system network design is more fully discussed in *Data Network Design*, by Darren L. Spohn, McGraw-Hill Inc. (1993), and conventional data communications is more fully discussed in *Data Communications Principles*, by R. D. Gitlin, J. F. Hayes and S. B. Weinstain, Plenum Press (1992) and in *The Irwin Handbook of Telecommunications*, by James Harry Green, Irwin Professional Publishing (2nd ed. 1992) Each of the foregoing publications is incorporated herein by reference. Alternatively, the hardware configuration is, for example, arranged according to the multiple instruction multiple data (MIMD) multiprocessor format for additional computing efficiency. The details of this form of computer architecture are disclosed in greater detail in, for example, U.S. Pat. No. 5,163,131; Boxer, A., Where Buses Cannot Go, IEEE Spectrum, February 1995, pp. 41–45; and Barroso, L. A. et al., RPM: A Rapid Prototyping Engine for Multiprocessor Systems, IEEE Computer February 1995, pp. 26–34, all of which are incorporated herein by reference.

In alternate preferred embodiments, the above-identified processor, and, in particular, CPU 916, may be replaced by or combined with any other suitable processing circuits, including programmable logic devices, such as PALs (programmable array logic) and PLAs (programmable logic arrays). DSPs (digital signal processors), FPGAs (field programmable gate arrays), ASICs (application specific integrated circuits), VLSIs (very large scale integrated circuits) or the like.

By way of illustration, the computer 900 includes a personal computer, such as, a Pentium MMX 166 microprocessor-powered personal computer, as manufactured, for example, by Dell Computer Corporation of Round Rock, Tex., and having, for example, 32 megabytes of RAM, 2 megabytes of VRAM, a 2.0 gigabyte hard drive, a keyboard, a mouse, a 1024×768 resolution SVGA color monitor, a CD-ROM, and/or a digital signal processor. The personal computer, for example, is network capable. The computer 900 runs the control and analysis software including initialization calibrations set-up, data acquisition, filtering, statistics, results calculation, and report printing.

It is, of course, understood that the computer is alternatively embodied as a thin client, such as a network computer or a NetPC, in communication with a flow analyzer, wherein control and analysis software, discussed below, resides on a network accessible by the thin client. Alternatively, the computer is embodied as a minicomputer or a mainframe in communication with a flow analyzer, wherein resides the control and analysis software.

Figure 5:
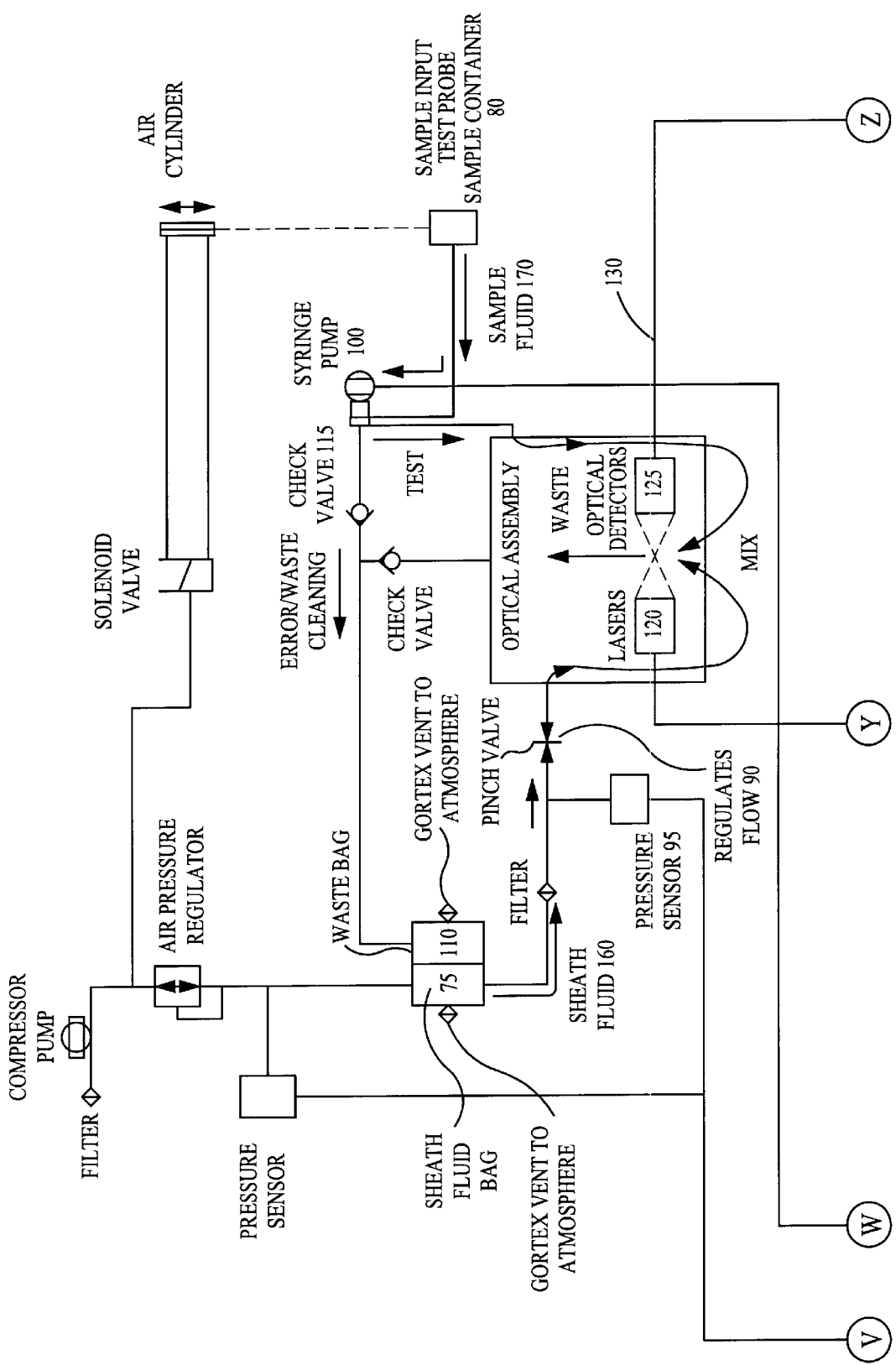
FIG. 5 is a detailed schematic of an illustrative embodiment of part of the present system.
Figure 6:
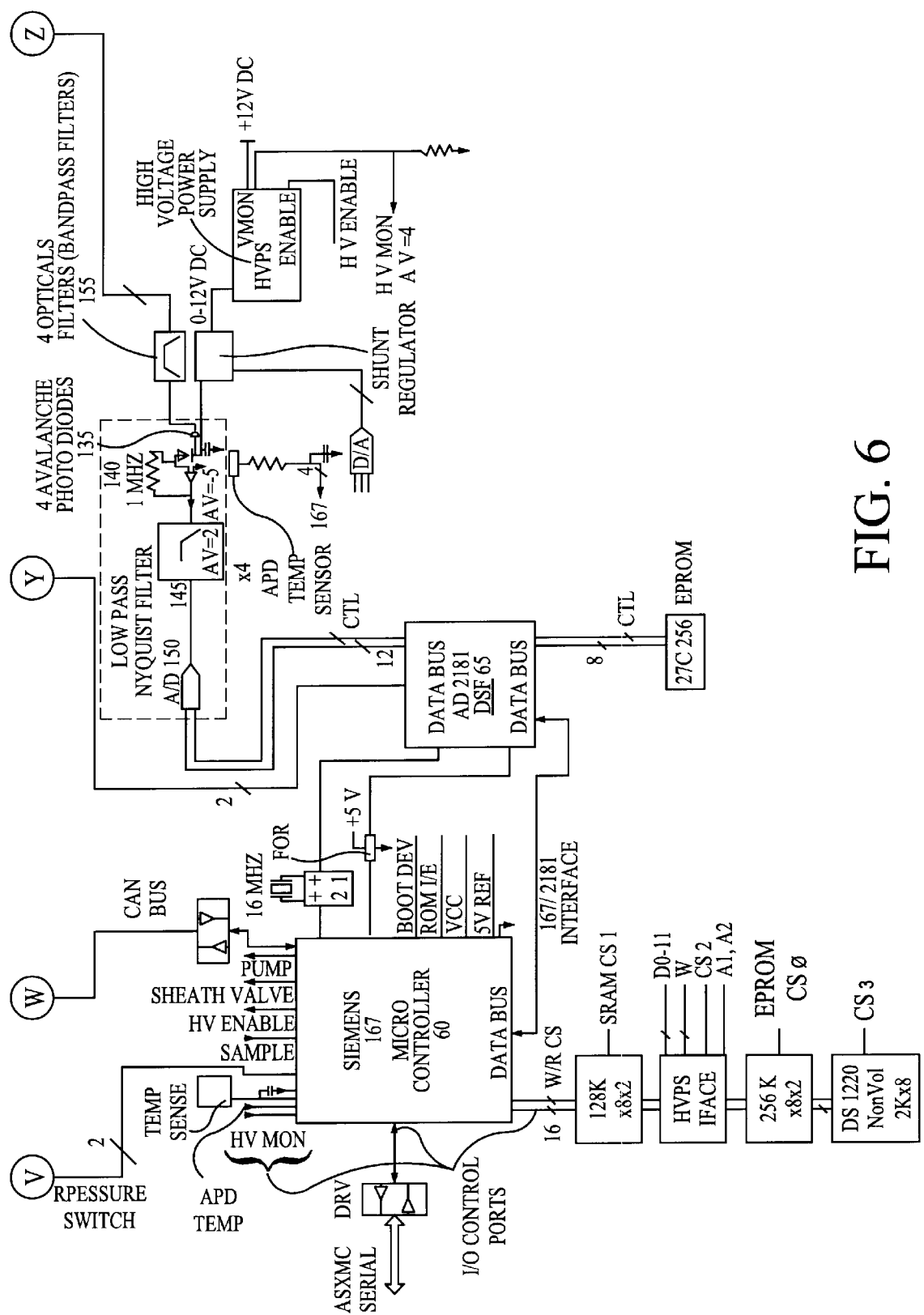
FIG. 6 is a detailed schematic of an illustrative embodiment of part of the present system.

As shown in FIGS. 4–6, the personal computer 90 is operatively connected to a flow analyzer, for example, via a standard serial or parallel connection interface card 15, which provides a communications interface between the computer bus of the computer and a flow analyzer data bus 20 of the flow analyzer 25.

The software 50 in the computer communicates with the flow analyzer 25 through the serial or parallel connection interface card 15 as follows. The flow analyzer 25 updates the communications interface with a block of parameters describing the flow analyzer's current state. Pertinent information includes, for example, the state of one or more of its photomultiplier tubes, fluid levels, etc. Using the serial or parallel connection interface card 15, the software optionally reports the current status of these parameters to the user. For example, the software 50 warns the user if, for example, the sheath fluid container is empty and/or requires refilling. The software 50 optionally also warns the user if, for example, the waste fluid container is full and/or requires emptying. The software 50 optionally further notifies the user if, for example, a pressure-related problem exists. An error message, such as "Bad Link," is optionally displayed, if, for example, it is determined that the flow analyzer 25 and the computer 10 are not communicating properly. The software 50 optionally monitors and compares the flow analyzer's settings to ensure that they fall within acceptable calibrated setting guidelines or settings. The software 50 optionally reports a parameter change to the user promptly after receiving the change via the serial or parallel connection interface card 15.

The flow analyzer 25, for example, reports light scatter events in the sample that passes therethrough and, for example, are detected above a threshold value, that is pre-set or user-defined. The flow analyzer 25 sends the events across the serial or parallel connection interface card 15 in, for example, a standard list mode data format, which facilitates data export to standard third-party programs and spreadsheets. Advantageously, such a format aids in systems integration of elements produced by disparate manufacturer's to create the instant invention. By way of illustration, events are optionally sent in blocks of an arbitrary fixed number, such as fifteen, or a variable number. Each event contains the detected amount of light at each photomultiplier tube, for example, and, optionally, a checksum to ensure proper transmission. Each event from a photomultiplier, for example, as represented by the amount of detected light is received as, for example, a linear value of a number of bits in length. The number of bits is, for example, one, two, three, ten, twenty, or more. Plainly, an event being described by a number of bits lower than ten is coarser than one being described by ten or more bits. By increasing or decreasing the number of bits used in the event value parameter, the resolution of the event, and thus the dynamic range thereof, is increased or decreased, respectively. Optionally, the software 50 in the computer 10 discards events that produce the checksum errors.

As shown in FIG. 6, the digital interface board 15 includes a standard microcontroller 60, such as the C167 microcontroller manufactured by Siemens AG of Munchen, Germany, and a standard digital signal processor (DSP) 65, such as the ADSP-2181 processor manufactured by Analog Devices, Inc. of Norwood, Mass. Advantageously, the digital interface board 15 is optionally protected from radiated noise by a standard shield. In addition, an optional heatsink covers the amplifying photo-detectors, such as, avalanche photodiodes, so as to equalize temperature while providing a secure mount for the light collimation optics and the optical fibers.

The digital interface board 15, for example, measures collected light from up to three or more channels and may, for example, resolve total light emitted for every event. In flow analysis, a light scatter event, for example, includes an instance of a cell or other particle passing through a spot or focal region of light, such as a laser, and scattering both the excitation light and, often, one or more fluorescent colors emitted from dye in the particle or cell. As the event occurs, the measured light increases as the particle enters the beam. The high speed analog-to-digital converters on the digital interface board 15, according to the instant invention, optionally continually or intermittently measures the light. Every channel is optionally sampled or measured, for example, every millionth of a second. Channels, of course, are optionally measured at rates greater than or less than every millionth of a second.

Figure 7:
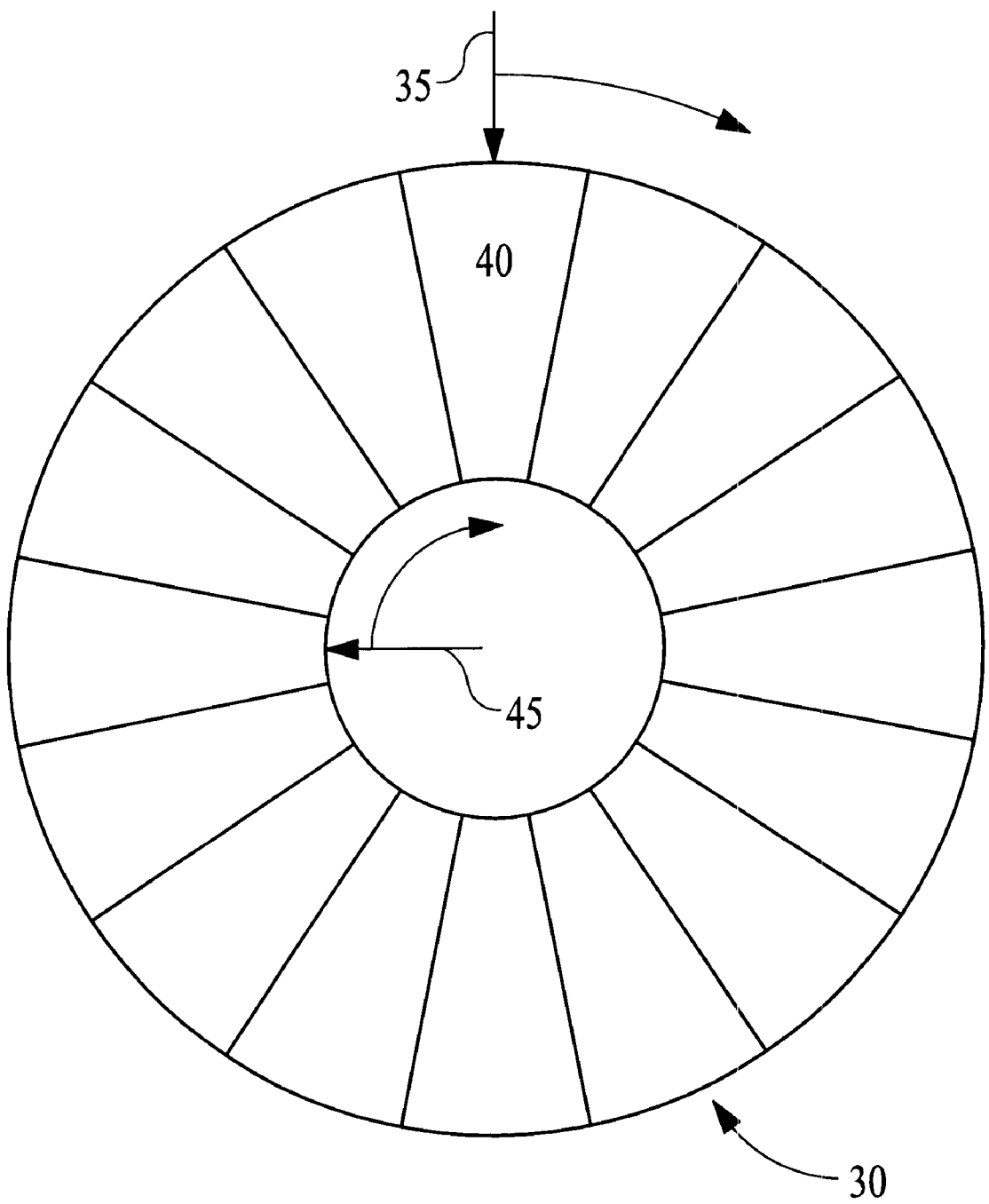
FIG. 7 is a schematic of an illustrative embodiment of a circular memory structure.
Figure 8:
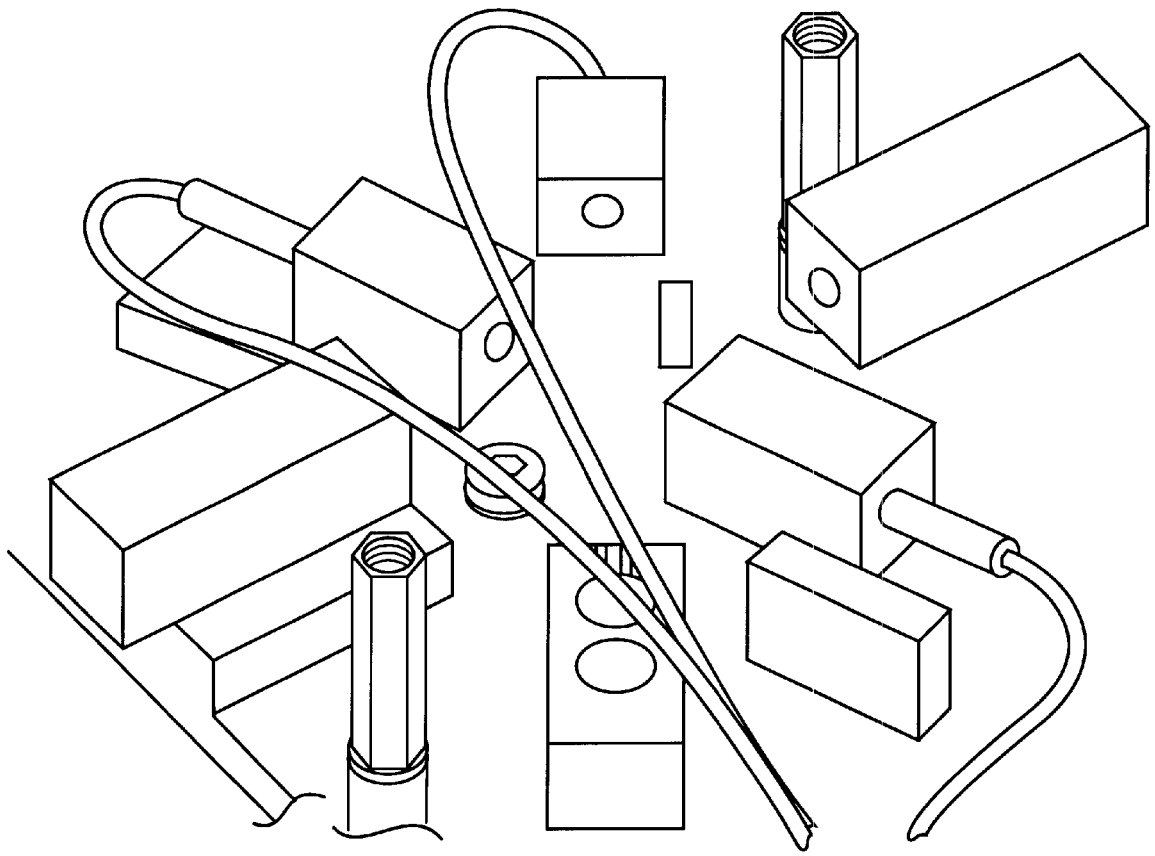
FIG. 8 is a perspective view of an illustrative embodiment of an array of light sources and optical detectors in the instant flow analyzer.

These measurements are optionally stored sequentially in an optional standard circular memory or standard buffer 30 in the interface card 15, as shown schematically in FIG. 7. A first pointer indicates the oldest storage position 40 in the memory, which is the position where the next measured channel sample will be stored. The circular buffer 30 has, for example, 1,000 storage positions for measurements from each channel. Note the number of storage positions depicted in FIG. 4 is solely intended for drawing convenience and is in no way intended to be limiting the scope of the invention. The circular buffer optionally includes greater than 1,000 storage positions or less than 1,000 storage positions, as the speed of the flow analyzer 25 sampling warrants. Then, for example, if the flow analyzer 25 according to the instant invention samples at 1,000,000 samples per second and the buffer includes 1,000 storage positions, the circular buffer 30 optionally holds measurements for analog-to-digital conversion from the previous 1/1000 of a second.

The DSP 65 on the digital interface board 15 optionally controls a second pointer 45 for the circular buffer 30. The second pointer optionally is programmed to stay a fixed trailing distance in time behind the first pointer 35 until the measured light exceeds a threshold value, e.g., a desired signal to noise ratio. It then moves forward, processing the measurements and analyzing the pulse. There are a number of processes known to those of ordinary skill in the art that are optionally performed on the pulse measurements, including digital filtering and/or waveform analysis, for example, that improve the quality of the measurement by extracting a signal in the presence of noise. By way of illustration, standard FIR filtering is advantageously used to improve the signal-to-noise ratio and, therefore, sensitivity.

At the conclusion of this signal processing, the DSP 65 advances its second pointer 45 until a new event is detected or until the second pointer reaches the fixed trailing distance.

The process optionally continues until all or substantially all events have been measured. It is important to note that digital filtering may take considerable time. The circular buffer size advantageously is optionally-large enough to handle the worst case scenario for maximum data storage to adequately accommodate processing time. A fast flow cytometer 25 handles, for example, 20,000 cells or beads per second. In the preferred embodiment, wherein, for example, 1,000 events are processed per second, that rate results in an average of only twenty meaningful measurements of a given event in the circular buffer 30. Thus, for example, a buffer 30 having 1,000 storage positions would far exceed this data storage need.

The interface data bus cable 20 provides a conduit for setup parameters to the flow analyzer 25 from the computer 90 via the serial and parallel connection 15. The cable 20 also provides a conduit for flow analyzer data output from the flow analyzer 25 to the computer 90 via the serial or parallel connection interface card 15.

The computer 90 is optionally also operatively connected to an optional printer 55 for printing one or more reports generated by the control and analysis software of the instant invention. The printer interfaces with the computer via a standard printer port, such as a Centronics printer port manufactured by Genicon Corporation of Waynesboro, Va.

FLOW ANALYZER OVERVIEW

As illustrated in FIGS. 8–13, flow analyzer 25 includes, for example, a standard flow cytometer capable of analyzing cells or particles by size and/or by fluorescence, distinguishing up to three, for example, or more fluorescent colors simultaneously. Optionally, the flow cytometer is a benchtop type model. The instant flow analyzer 25 is operatively connected to the personal computer 910 via a communications port. In general, the flow cytometer 25 advantageously integrates lasers, optics, fluidics, and advanced signal processing and/or have a small, for example, 17"×20" footprint. Such a flow cytometer 25, for example, includes a largely solid-state device.

More specifically, the flow cytometer 25 includes an examination zone 70, for example, a sample delivery viewing chamber or flow cell. The viewing chamber 70 is a standard quartz cuvette used in standard flow cytometers. Optionally, the cuvette 70 includes one or more flat air-to-glass interfaces. For example, as shown schematically in FIG. 14, the cuvette 70 has a hexagonal cross-section, thus effectively having six flat air-to-glass interfaces. Optionally, the number of air-to-glass interfaces of the cuvette equals the number of light sources and detectors.

Figure 15A:
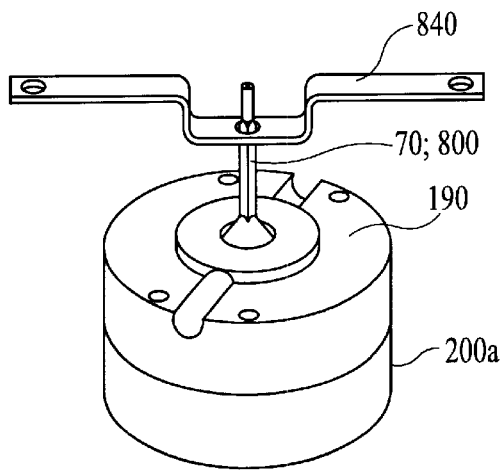
FIG. 15*a* is a perspective view of an illustrative embodiment of a cuvette holder.
Figure 15B:
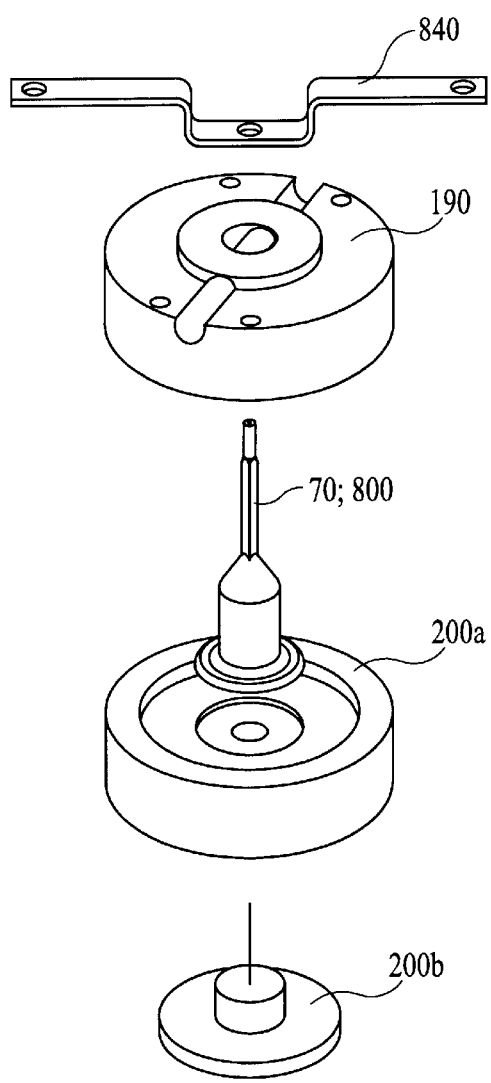
FIG. 15*b* is an exploded, perspective view of the cuvette holder shown in FIG. 15*a;*
Figure 16:
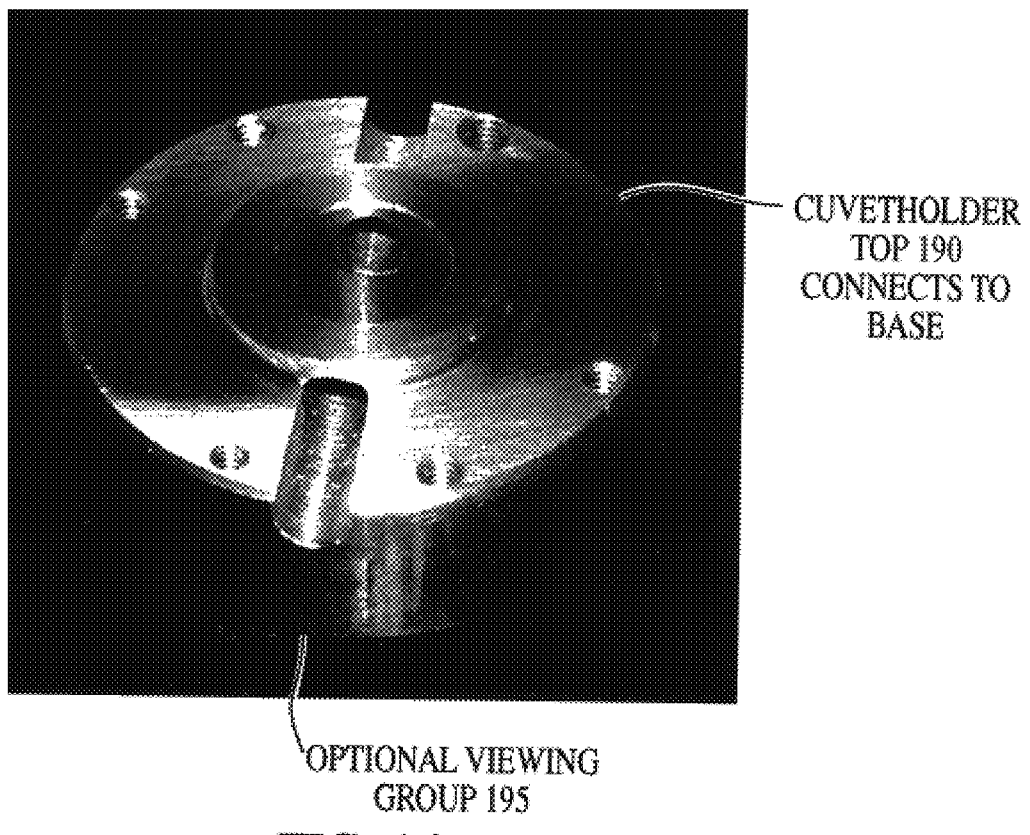
FIG. 16 is a perspective view of an illustrative embodiment of a cuvette holder top.

As illustrated in FIGS. 15 and 16, the flow analyzer 25 includes an optional cuvette holder top 190 which, for example, connects to a top plate or laser base of the light sources. The cuvette holder top 190 includes an optional viewing groove or grooves along a diameter or width of the holder top. The flow analyzer 25 includes a cuvette holder base, which optionally comprises two units 200a, 200b, wherein the cuvette 70 is held between the cuvette holder base 200a, 200b and the cuvette holder top 190.

Figure 14:
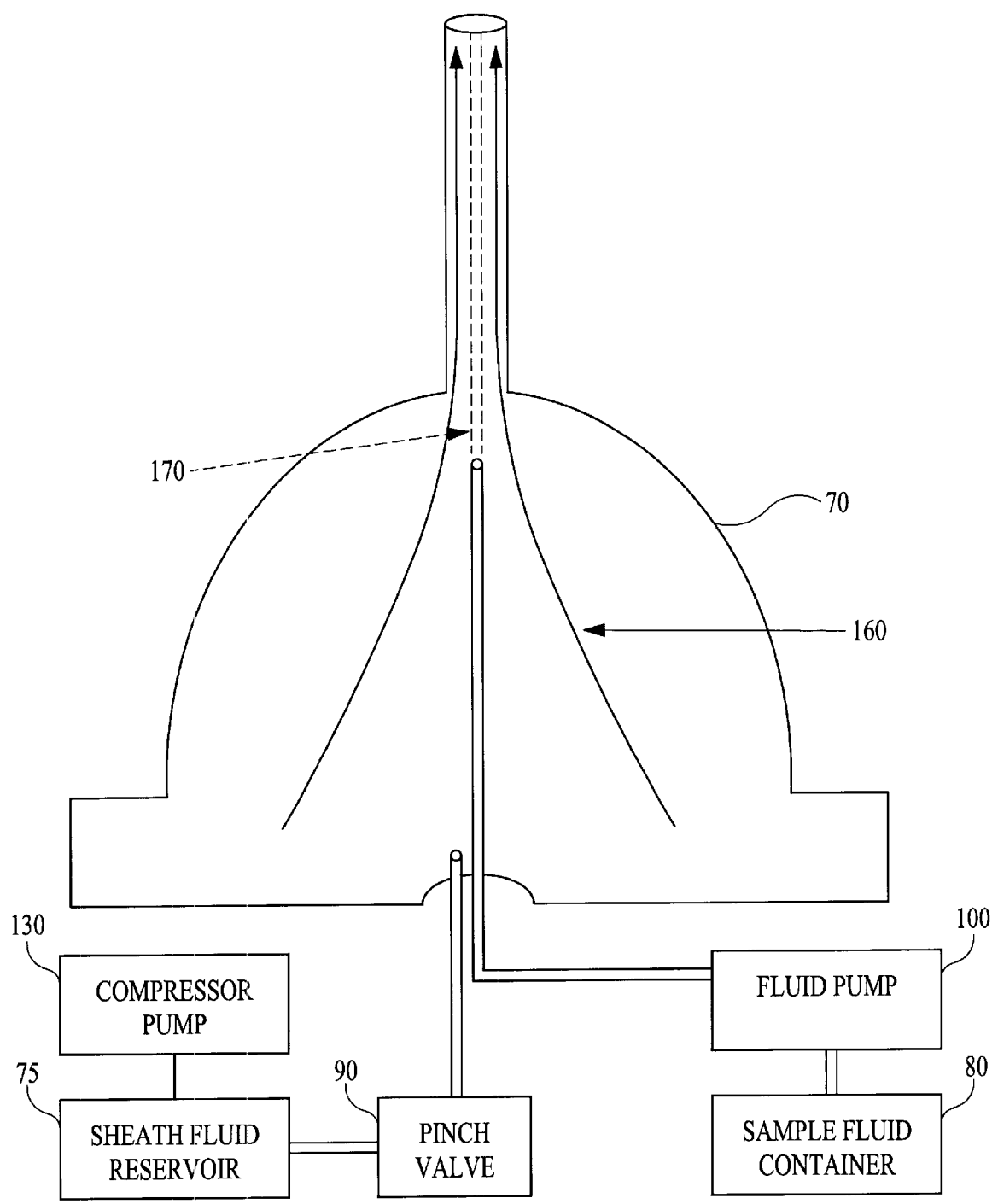
FIG. 14 is a schematic of an illustrative embodiment of the instant fluidics system.

As shown in FIG. 14, the cuvette is operatively connected to a sheath fluid reservoir or bag 75 and a sample fluid container 80. A standard compressor pump 165, for example, pumps air into the reservoir 75, forcing sheath fluid to flow from the sheath fluid reservoir 75 through a standard filter 85 and a standard flow arrestor 90, which is operatively connected to a standard sheath fluid pressure sensor 95, to the cuvette. The flow arrestor 90, for example, includes a pinch valve or a solenoid valve. The sample container 80, is connected to the cuvette 70 via, for example, a standard syringe pump 100 in such a manner as to ensure that the sheath fluid from the sheath fluid bag 75 ensheathes the sample fluid 170 before or in the cuvette 70. Optionally, the exit end of the cuvette 70 is operatively connected via a standard check valve 105 to a waste fluid bag 110. Optionally, the syringe pump 100 for the sample fluid is also connected by a check valve 115 to the same waste fluid bag 110 or a different waste fluid bag.

Figure 9:
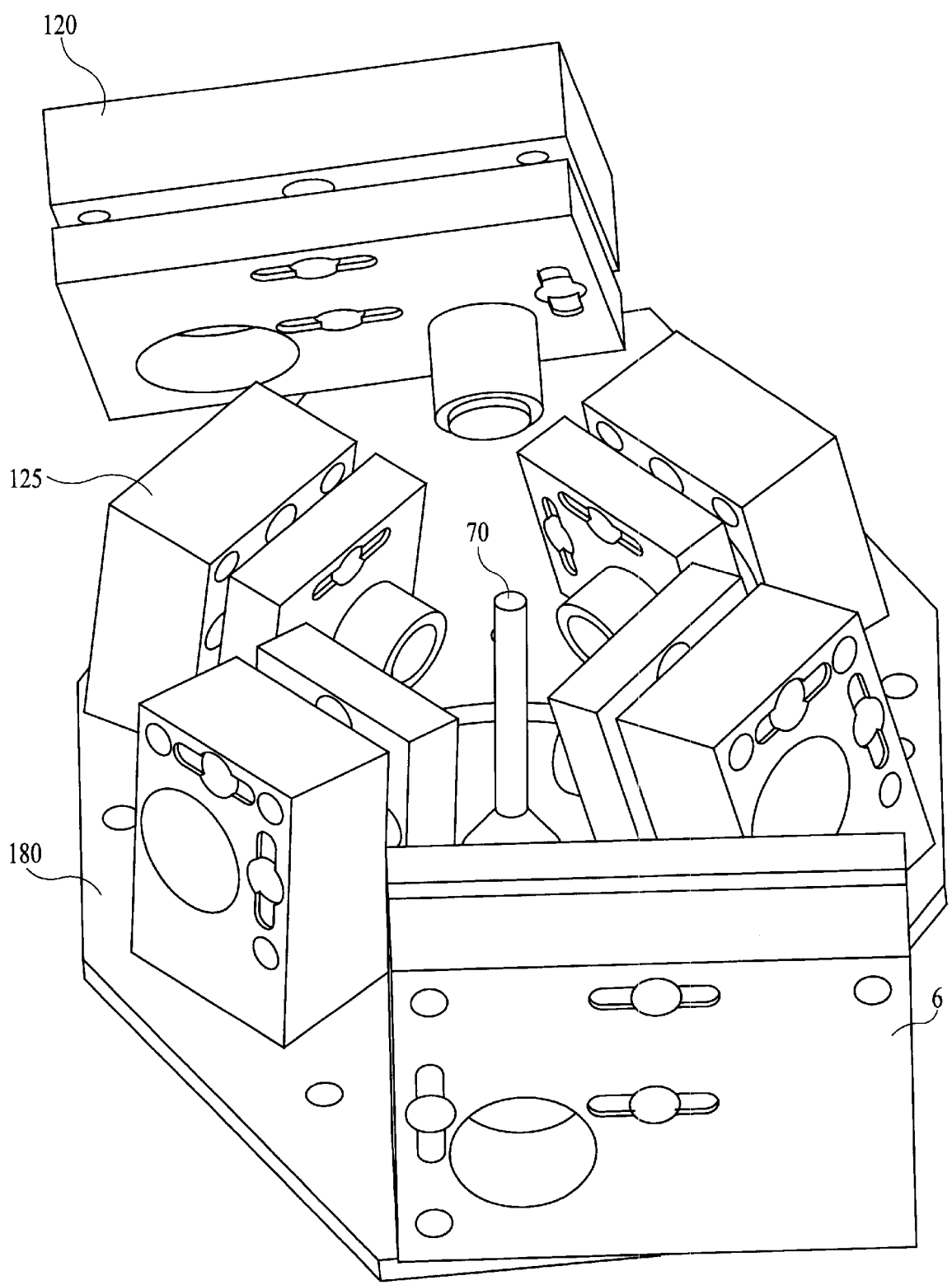
FIG. 9 is a perspective view of an illustrative embodiment of the present light source-optical detector array.
Figure 10:
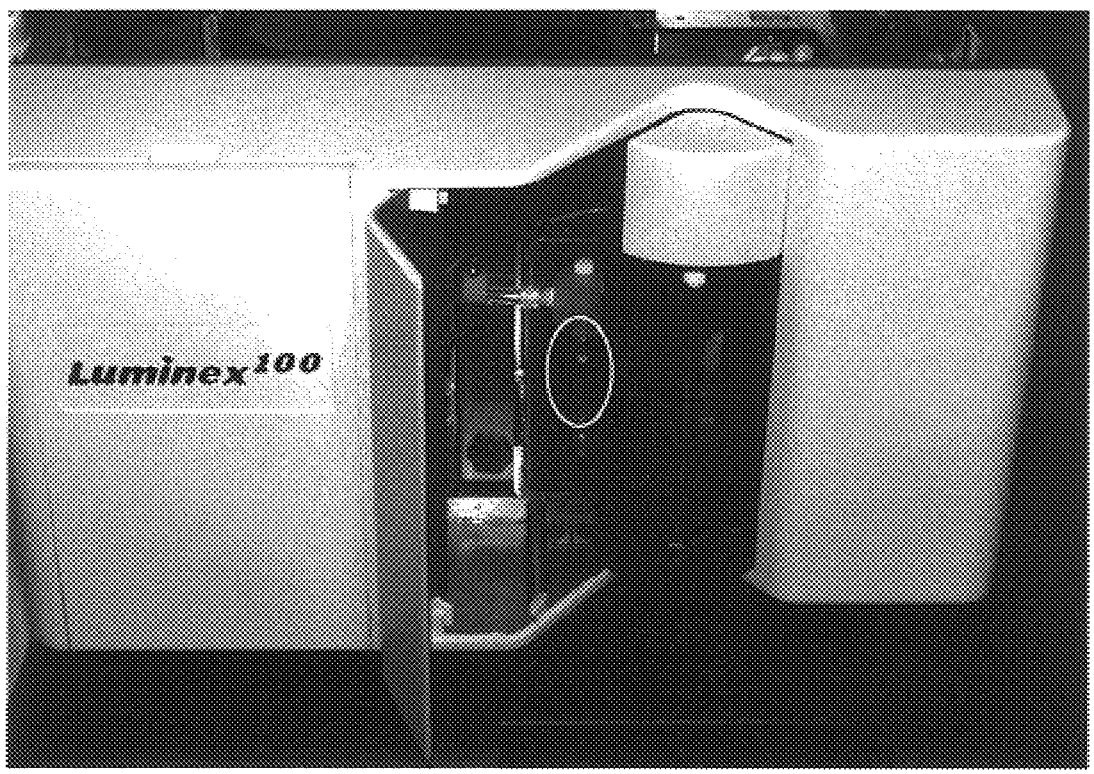
FIG. 10 is a perspective view of an illustrative embodiment of the instant flow analyzer.
Figure 11:
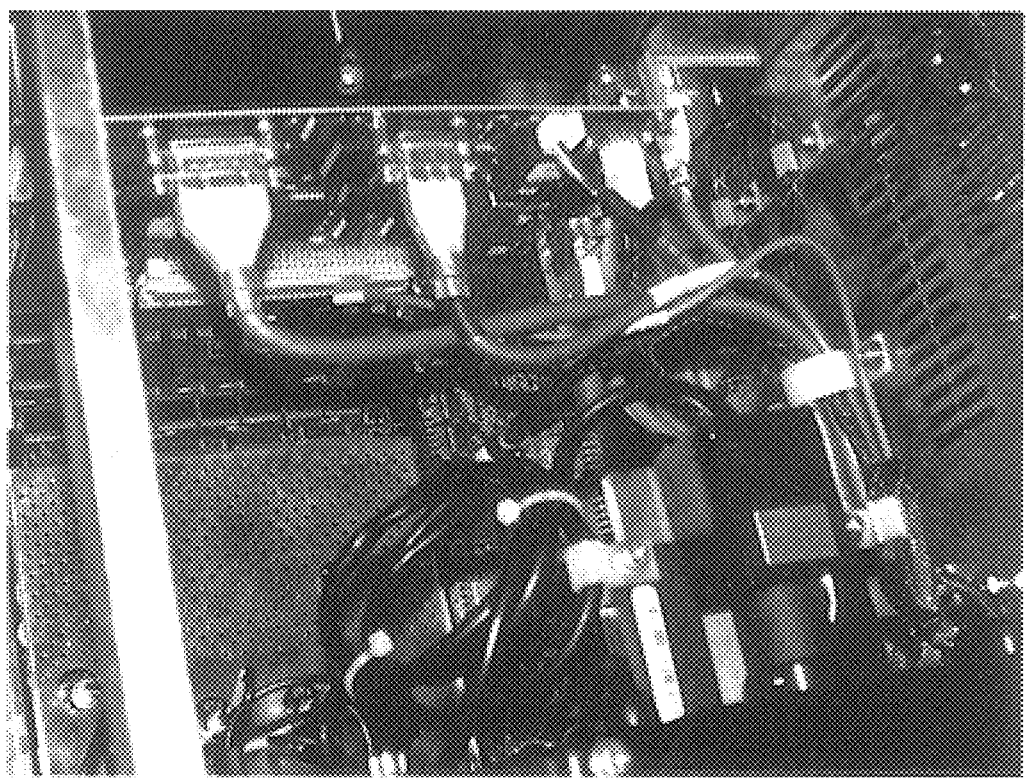
FIG. 11 is a perspective view of an illustrative embodiment of the circuitry of the instant flow analyzer.

On an optional top plate or laser base 180, standard light sources 120 and standard optical detectors 123 optionally surrounds the periphery of the viewing chamber 70, as configured, by way of example, in FIG. 9. The light sources 120, for example, includes standard laser diodes or standard light emitting diodes. For example, dual diode lasers are optionally horizontally opposed and are optionally horizontally pitched down approximately five degrees. A pitch having a fewer number or a greater number of degrees is also acceptable. By way of further illustration, one or both of the light emitting diodes optionally includes continuous wave (CW) light emitting diodes emitting one, two, or more wavelengths or wavelength bands of light. All of the light sources 120 share identical, substantially identical, similar, or overlapping focal regions in the viewing chamber 70 on the flowing sample fluid 170, in operation. The focal region includes a cross-section of, for example, 60 microns×30 microns, although other geometries and sizes are also applicable to the present invention.

The optional top plate or laser base 180 is, for example, a unitary plate or a rigidly connected plurality of plate for providing stability to the optical assembly. Such stability, for example, facilitates the maintenance of the above-mentioned identical, similar, or overlapping focal regions. Advantageously, the rigid top plate 180 reduces the frequency for any recalibration of the focal regions of the light sources.

Figure 17:
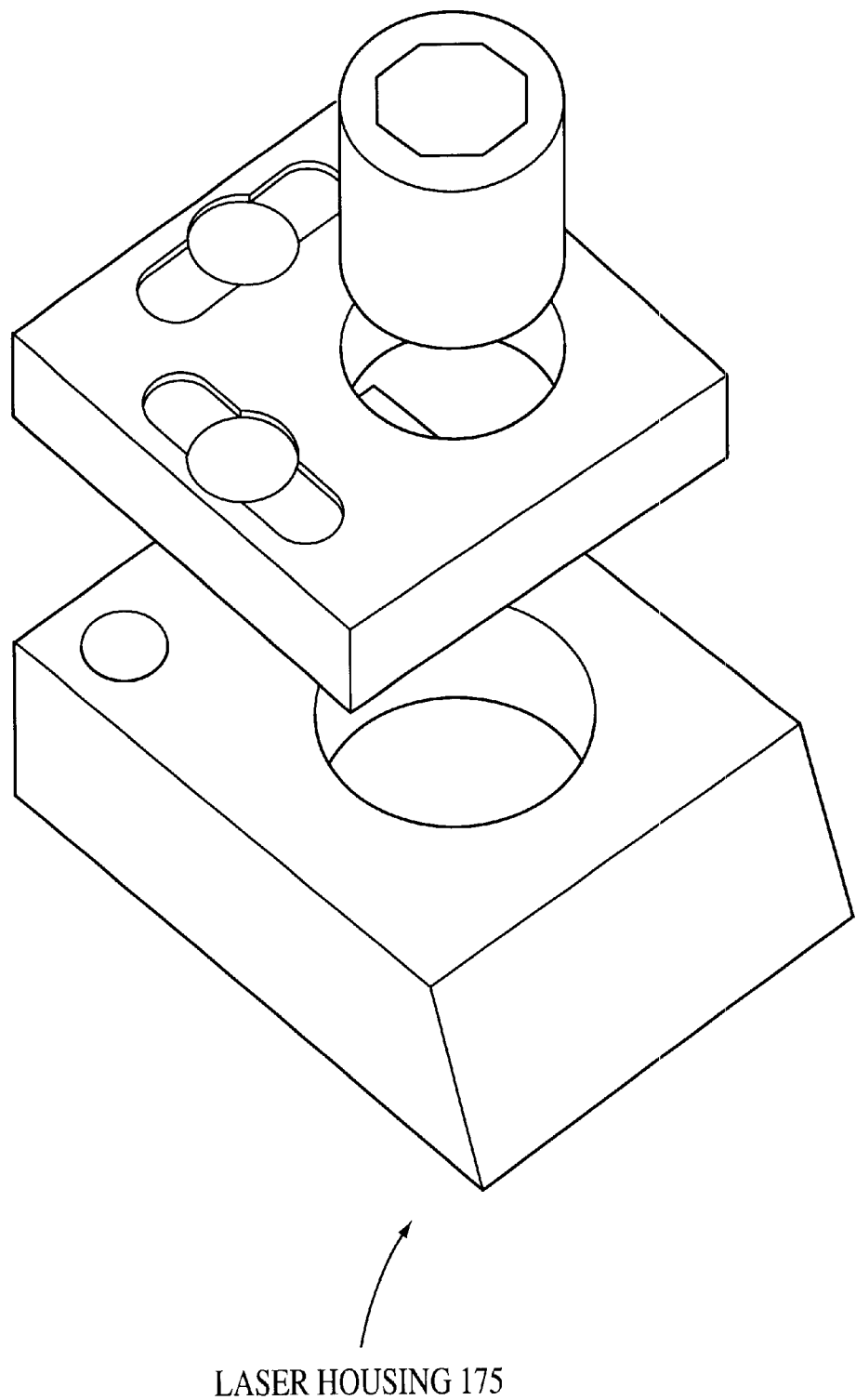
FIG. 17 is a perspective view of an illustrative embodiment of a laser housing.
Figure 18:
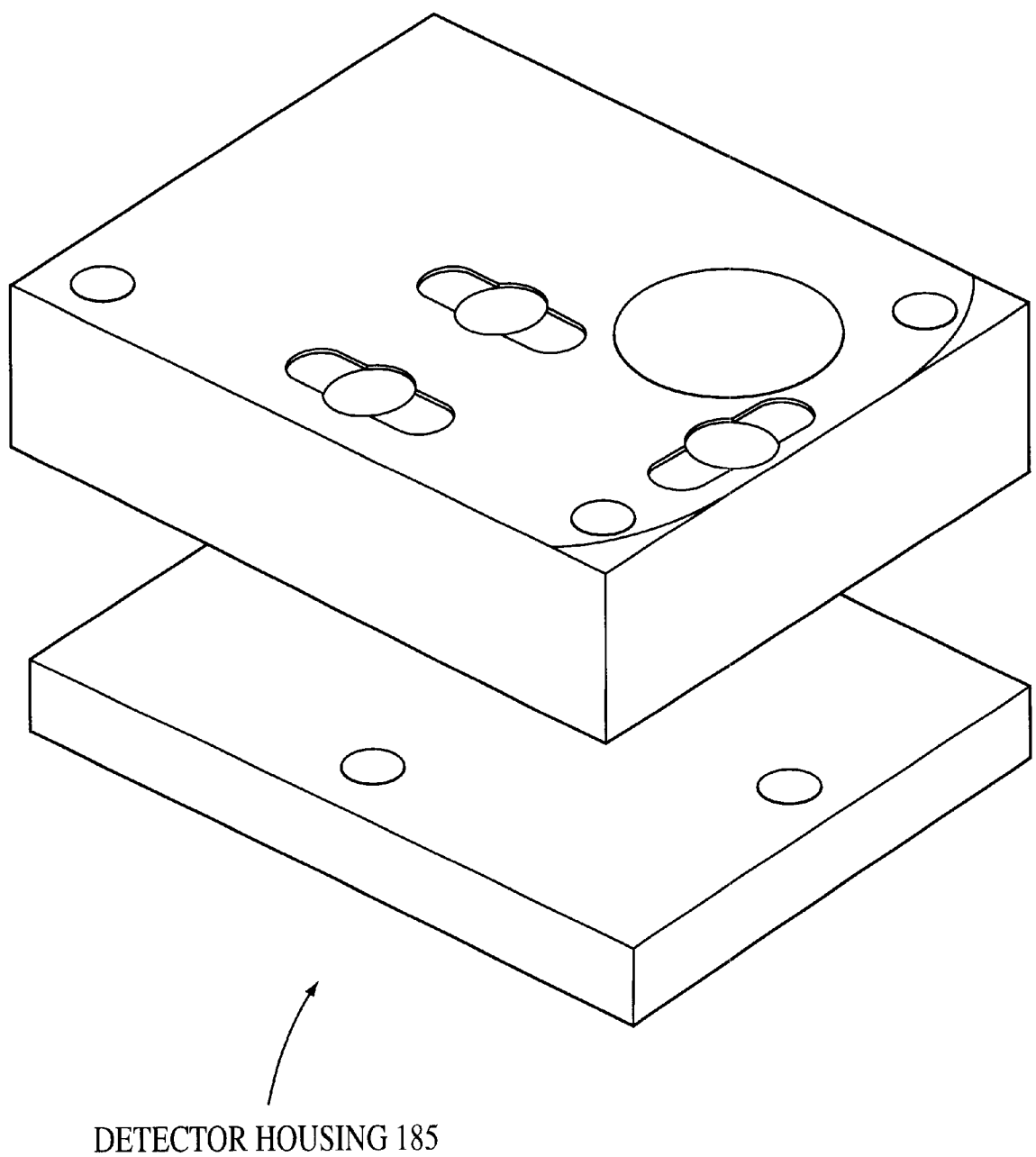
FIG. 18 is a perspective view of an illustrative embodiment of a detector housing.

Optionally, one or more light sources are optionally located in a housing, such as laser housing 175, which advantageously enhance the rigidity of the light source detector assembly, as shown in FIG. 17. Each laser housing is optionally and advantageously affixed to the top plate 180. Similarly, optionally, one or more optical detectors is located in a detector housing 185, which is also or alternatively, affixed to the top plate 180, as shown in FIG. 18.

The above-mentioned light sources, alternatively or in addition, include, by way of example, laser diodes, broad spectrum arc lamps, including mercury and xenon arc lamps, standard flash lamps, as well as lasers, including He—Ne, Ar—ion, Ar/Kr, UV, and YAG lasers, and other suitable standard light sources.

Lasers that can emit light at more than one wavelength simultaneously or substantially simultaneously can also be used. For example, in this regard, there is at least one laser which emits at 488 nm and 357 nm simultaneously. In this situation, one laser would replace two single beam lasers/light sources. Alternatively, frequency tunable lasers are also acceptable. Frequency tunable lasers include, for example, dye lasers, excimer lasers, and semiconductor lasers. Use of a frequency tunable laser optionally reduces the number of required light sources. Likewise, frequency tunable laser diodes and other frequency tunable light sources are also within the scope of the invention.

The arc lamps optionally require conventional polarizers in the light path toward the viewing chamber. The lasers require standard beam shaping prismatic expanders or their equivalents between the light sources and the flow cell. A possible disadvantage to using arc lamps and lasers as well as polarizers and prismatic expanders, is increased size of the overall apparatus relative to an embodiment using laser diodes. Also, the lasers that emit at more than one wavelength often require different prismatic expanders for each wavelength. But, for practical reasons, one set of prismatic expanders are, for example, used for both wavelengths.

It is to be understood that references made hereinafter to lasers and/or light sources, unless otherwise specified, are made by way of convenience and are not intended to exclude the above-mentioned acceptable light sources.

The standard optical detectors 125 are connected via, for example, at least one standard multi-mode fiber optic cable 130 to serially connected amplification, filtering, and digital conversion units. The amplification units optionally include standard optical amplifiers 135, for example, one or more standard avalanche photodiodes. The multi-mode fiber optic cable 130 includes, for example, at least as many bundles as amplification units, each bundle operatively connected to a respective standard amplification unit. Each amplification unit is operatively connected to a respective filtering unit. Each filtering unit includes one or more band-pass filters 155, each having a band-pass frequency or frequency bands corresponding to known emission wavelengths or wavelength bands. Optionally, each bundle in the multi-mode fiber optic cable is connected to a standard single amplification, filtering, and digital conversion unit via a multiplexer or selector. Such an implementation, for example, trades off processing time for manufacturing complexity.

The number of optical detectors 125, optionally, depend at least in part on the total number of wavelengths emitted by the light sources 120. That is, for example, if there are two light emitting diodes, each emitting two, respective, distinct wavelengths of light, four optical detectors are optionally implemented, one for each emitted wavelength of light.

Alternatively, the number of optical detectors 125 may not be so correlated. That is, for example, if there are two light emitting diodes, each emitting two respective, distinct wavelengths of light, then, for example, one optical detector, connected to a multi-mode fiber optic cable having four or more bundles, is optionally implemented. Alternatively, if there are two light emitting diodes, each emitting two, respective, distinct wavelengths of light, for example, two optical detectors, each having a multi-mode fiber optic cable including two bundles, is optionally implemented.

Optionally, if multiple optical detectors are implemented, the multi-mode fiber optic cables therefrom are optionally connected to one or more standard multi-pass filters. Alternatively, if a single optical detector is implemented, the multi-mode fiber optic cable therefrom are optionally connected to one or more multi-pass filters. Use of a multi-pass filter optionally entails serially connected low pass filters to isolate signals in desired frequency bands. Implementation of one or more multi-pass filters and additional low-pass filters, for example, add to the size and complexity of the instant invention in comparison to implementation of multiple band-pass filters.

As shown in FIG. 6, each band-pass filter 155 optionally is connected in series with for example, a standard avalanche photodiode 135, a standard inverting amplifier 140, a standard low-pass Nyquist filter 145, and a standard analog-to-digital converter 150. Alternatively, one or more of the avalanche photodiodes 135 is optionally replaced with optical amplifiers or photo-detectors known in the industry, such as photomultiplier tubes and optically amplified photodiodes. The cutoff frequency for the Nyquist filter 145, for example, is 450 kHz. It is understood that the cutoff frequency optionally includes another value consistent with the characteristics of the Nyquist filter 145 in the instant configuration. The analog-to-digital converters 150, in turn, are optionally connected in parallel to standard digital signal processor 65. The DSP 65 optionally polls the parallel inputs sequentially, substantially simultaneously or simultaneously. Alternatively, the analog-to-digital converters 150 are optionally coupled or connected to a standard selector or standard multiplexer, which in turn is optionally connected to the digital signal processor 65. The selector passes signals from a single analog-to-digital converter 150 to the digital signal processor 65. Such a selector advantageously permits implementation of a less sophisticated digital signal processor than might otherwise be needed to handle parallel inputs from multiple analog-to-digital converters.

Optionally, the instant invention optionally includes two or more digital signal processors working in parallel or in sequence. In such a case, a selector, such as the serially configured multiplexer and demultiplexer, selects which of the analog-to-digital converters can transfer its data to which of the digital signal processors at a given time. Parallel digital signal, processors may increase the cost of the instant invention, but may also increase the speed of data processing for analyte determination.

Figure 45:
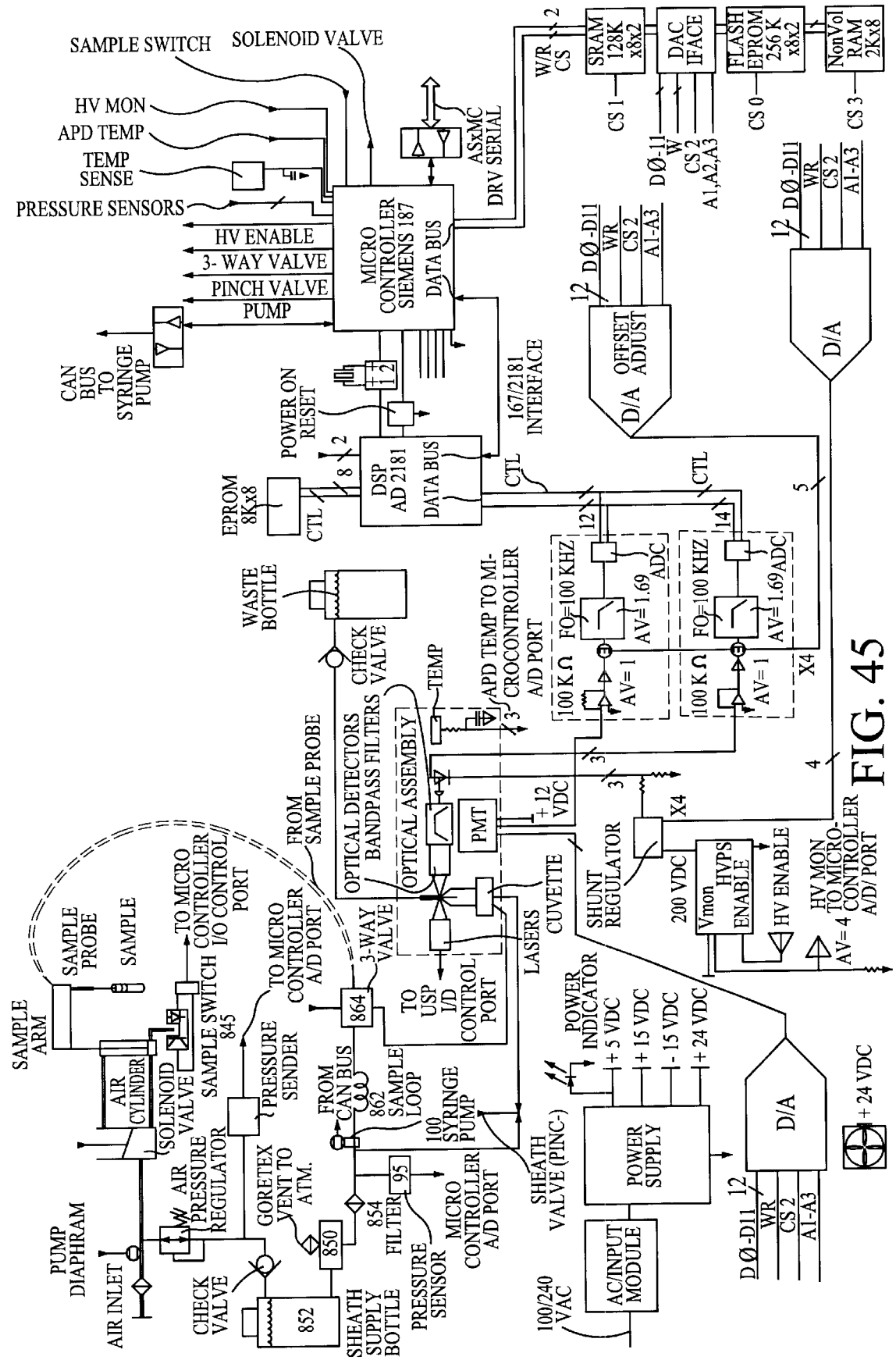
FIG. 45 is a schematic of an alternative embodiment of the instant invention.

An alternative embodiment of the instant flow analyzer is shown, by way of example, in FIG. 45. Components identical to those in the above-described embodiment are given identical reference numerals. As such, only the differing components or configurations of the alternative embodiment will be described hereinbelow.

I have recognized that a curved or rounded inner interface of a cuvette, for example, the sheath fluid-to-glass interface of a quartz cuvette, is a contributor to light distortion or background noise levels. Such an inner interface impedes measurement of emitted fluorescence because the curved interface effects a sub-optimal level of light scattering within the cuvette.

Figure 46:
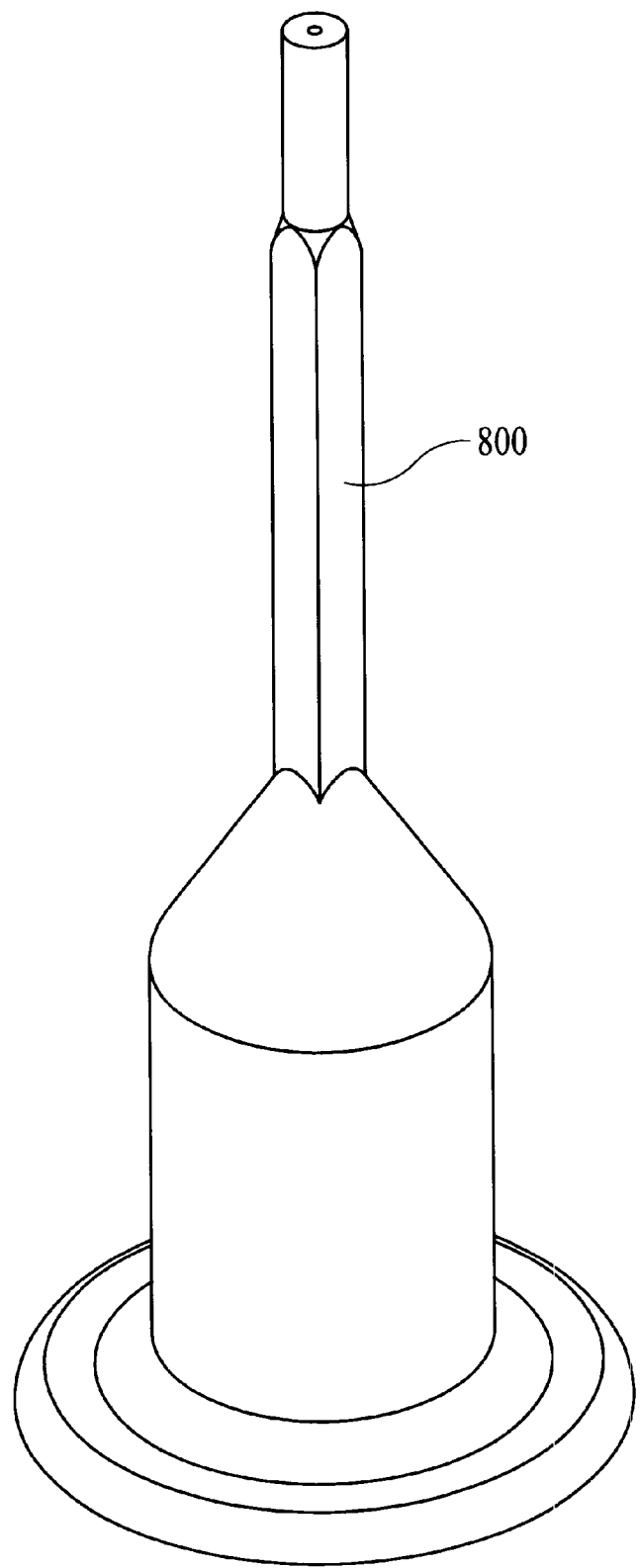
FIG. 46 is a perspective view of a modified cuvette.

I have determined that optional modified cuvette 800 including a flat air-to-glass interface and a flat glass-to-fluid interface, as shown, by way of example, in FIG. 46, addresses this very shortcoming. Modified cuvette 800 includes a square or rectangular cross-section. Advantageously and unexpectedly, the modified cuvette 800 including a neck-up region having a flat air-to-glass interface, a flat-glass-to-fluid interface, and a square cross-section improves sensitivity of the instant invention between ten and one hundred times than otherwise possible with a cuvette having a rounded glass-to-fluid interface.

Figure 47:
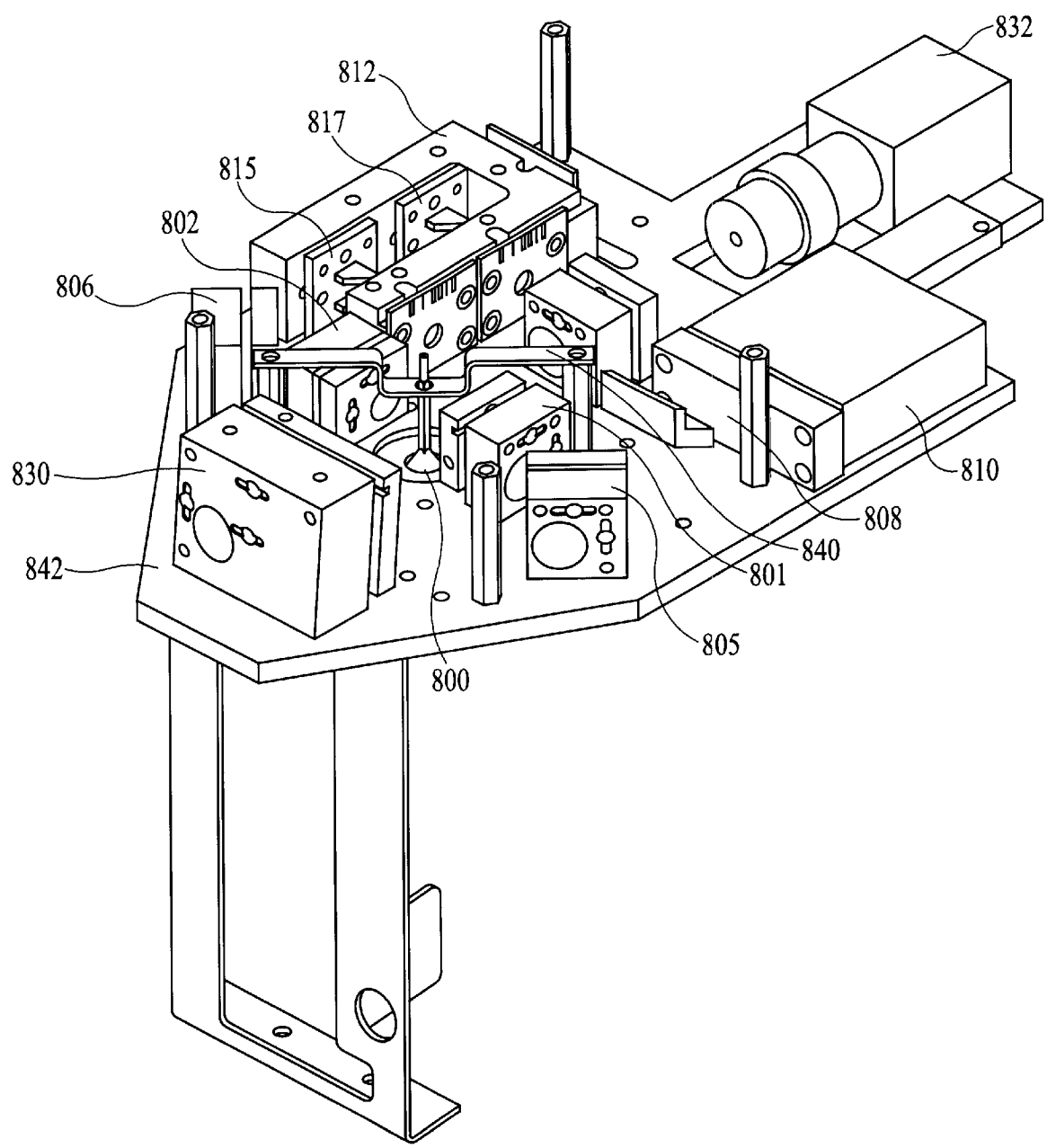
FIG. 47 is a perspective view of exemplary optical assembly components of the alternative embodiment.
Figure 48:
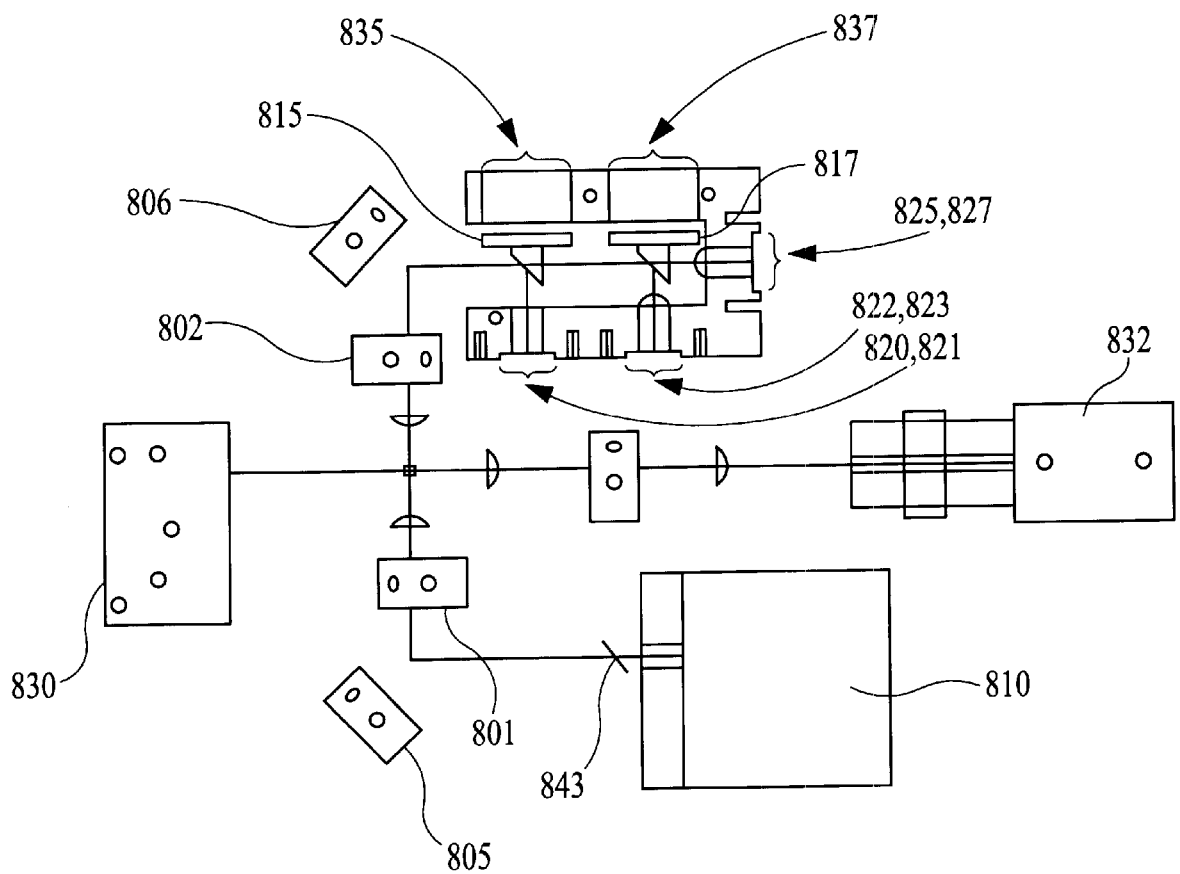
FIG. 48 is a planar view of exemplary optical assembly components of the alternative embodiment.

By way of illustration, the modified cuvette 800 optically cooperates with one or more optional standard magnification lens 801, 802, as shown in FIGS. 47 and 48. Optionally, magnification power of the lenses 801, 802 is between approximately 20× and 40×. Advantageously, the magnification power of lenses 801, 802 is 25×. The magnification lens 801 magnifies light from the modified cuvette 800, directing the light via an entrance slit 808 to a filter and optical amplifier assembly 810. Advantageously, optional mirror 805 reflects light from lens 801 to, the entrance slit 808. The mirror 805 optionally includes a dichroic mirror reflecting light having wavelengths, for example, in a range of 550 nm and 610 nm. Use of the mirror 805 facilitates miniaturization of the flow analyzer.

The entrance slit 808 is sized sufficient to pass light relating to the fluid in the cuvette. Optionally, the size of the entrance slit 808 is limited so as to block light from the glass-to-fluid interface to the glass-to-air interface. For example, if the fluid core in a cuvette is twelve microns in cross-section, the slit 808 is between about twelve microns and about one tenth of an inch or 40 microns. Light from, for example, a twelve micron fluid core falls well within a forty micron. entrance slit 808, thereby permitting jiggling of the instant apparatus with little or no degradation of performance.

Optionally, a dichroic mirror or reflector 843, as shown, by way of example, in FIG. 48, is placed in front of the entrance slit 808 to reflect light having wavelengths associated with bead identification. For example, the dichroic reflector 843 reflects light in a range of 630 nm to 760 nm to eliminate wavelengths of light to be used by the infrared wavelength detector, the red wavelength detector, and/or the side scatter detector, as described below.

Optionally, the filter and optical amplifier assembly 810 identifies a presence and/or quantity of one or more analytes of interest in a sample fluid. By way of illustration, the presence of an analyte of interest is identified by one or more fluorescence emission intensities, such as an orange fluorescence emission having a 585 nm wavelength. By way of example, the filter and optical amplifier assembly 810 includes a bandpass filter and a photomultiplier tube. Other suitable types of optical amplifiers, such as avalanche photodiodes, are acceptable. The bandpass filter passes, for example, 565 to 585 nm light so that the photomultiplier tube detects a presence of 585 nm light. Plainly, other colors and/or wavelengths are acceptable for identifying an a presence of an analyte of interest, provided that they are distinguishable from any other fluorescence emissions excited during the course of operation of the instant invention.

Advantageously, magnification lens 802 magnifies light emitted from the cuvette 800 to one or more optical detectors, for example, for bead identification. For example, the one or more detectors include three detectors for detecting, one or more characteristic classification parameters of a bead. By way of illustration, classification parameters optionally include characteristic fluorescence emission intensities and/or bead size. For instance, beads of a bead subset in a multiplexed analysis are optionally distinguished from beads of another subset by dyes having differing fluorescence emission intensities of red light, e.g., 658 nm light, and infrared light, e.g., 712 nm light. In such a case, for example, red wavelength detector 822 and an infrared wavelength detector are advantageously implemented. By way of illustration, referring to FIG. 48, light passing through magnification lens 802 partially reflects off of a beam splitter through a standard bandpass filter 821 passing, for example, light having wavelengths in a range of 700 nm to 760 nm so that 712 nm light is detected by the infrared wavelength detector 820. The beam splitter, for example, includes dichroic mirror 815 reflecting light having wavelengths exceeding 700 nm. For example, the dichroic mirror is stainless steel, though other suitable materials are acceptable. The infrared wavelength detector optionally includes an avalanche photodiode. Other suitable detectors, such as photomultiplier tubes, are acceptable.

Optionally, light passing through the dichroic mirror 815 is subject to a bandpass filter 823, which passes, for example, light having wavelengths in a range from 648 to 658 nm so that 658 nm light is detected by the red wavelength detector 822. The infrared wavelength detector 822 optionally includes an avalanche photodiode. Other suitable detectors, such as photomultiplier tubes, are acceptable.

Alternatively, light passing through the dichroic mirror 815 partially reflects off of a beam splitter through a standard bandpass filter 823, which passes 658 nm light to the red wavelength detector 822. The beam splitter, for example, includes dichroic mirror 817, which reflects light having wavelengths about 650 nm. Optionally, light passing through dichroic mirror 817 is subject to a standard bandpass filter 827, which passes light having wavelengths about 645 nm to an optional side scatter detector 825. Advantageously, the side scatter detector is optionally used as a doublet discriminator so as not to mis-identify two or more beads as a single bead.

I have also recognized that light path differences exist between the modified cuvette 800 and the various detectors described above in the alternative embodiment. Optionally, to compensate for the light path differences, magnification lens 802 is focused to maximize a signal received at the infrared wavelength detector 820. Optionally, additional standard lenses are positioned between the dichroic mirror 817 and the red wavelength filter 823 and between the dichroic mirror 817 and the side scatter filter 827 to correct for light path differences thereto.

Optionally, light sources for the either the first described embodiment or the above-described alternative embodiment include a laser diode 830 and/or a diode pumped laser 832, as shown, by way of example, in FIG. 47. For instance, the laser diode 830 includes a laser diode emitting red light, such as 635 nm light, and the diode pumped laser 832 includes diode pumped laser emitting a green light, such as 532 nm light. Optionally, one, two, or more lenses shaped the round beam from the diode pumped laser 832 into an elliptical. spot on the cuvette. The resulting elliptical spot, for example, includes a 20 micron by 60 micron cross-section, wherein the major axis is horizontal. Advantageously, light from the laser diode on the cuvette is optionally already in the desired elliptical shape and need not require shaping optics.

I have also recognized that performance of flow analyzers, such as described herein, is facilitated by stability of the components thereof. I have determined that an optional optical assembly base or platform 842, as shown, by way of example, in FIG. 47, advantageously enhances stability of the components of the flow analyzer 25. For instance, a top of the modified cuvette 800 is effectively immobilized by an optional stability bracket 840 connected to the optical assembly base frame 842. A bottom of the modified cuvette is effectively immobilized by a cuvette holder top 190, described above and optionally connected to the optical assembly base frame 842, though not shown in FIG. 47 for clarity.

Further to my goal of enhancing stability, the instant flow analyzer 25 includes an optional U-block frame or assembly 812 affixed to the optical assembly base frame 842. Optionally, one or more of the dichroic mirrors 815, 817 is adjustably connected to the U-block assembly 812 by a respective push-pull assembly, such as a screw tap and spring assembly 835, 837. Screw tap and spring assembly 835 is optionally used to aim, automatically or manually, dichroic mirror 815 to the infrared wavelength detector 820. For example, the screw tap in the assembly 835 pushes optional holders on the dichroic mirror 815, and the spring in the assembly 835 pulls the dichroic mirror 815. Likewise, screw tap and spring assembly 837 is optionally used to aim, automatically or manually, dichroic mirror 817 to the infrared wavelength detector 820. The holders include, for example, a stainless steel material, or other suitable material.

I have further recognized that it is desirable to avoid sample fluid from entering the sample pump, for example, around the seals thereof. I have determined that a standard sample loop 862, as shown, by way of example, in FIG. 45, advantageously solves this very problem. Specifically, the sample loop 862 is dimensioned so that sample fluid enters the sample loop, but not the sample pump 100. By way of illustration, referring to FIG. 45, sample fluid is drawn by the sample pump 100 into the sample loop 862. Then, for example, an optional standard three way valve 864 closes a valve to the sample injection needle, opens a valve to cuvette 70, 800, and pumps the sample fluid from the sample loop 862 into the cuvette.

Figure 49:
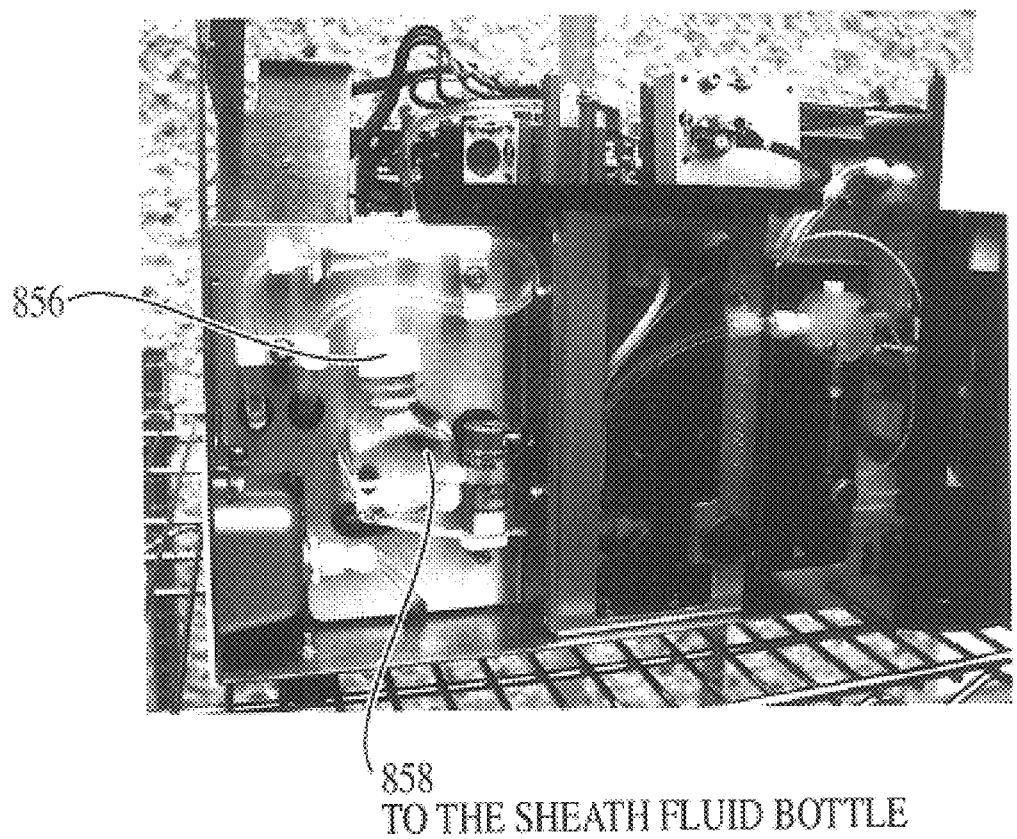
FIG. 49 is a perspective view of a de-bubbler according to the instant invention.

I have also recognized that air bubbles in the sheath fluid stream hinder flow in the cuvette by clinging to the sides thereof, and are difficult to remove. An optional de-bubbler 850, as shown, by way of example, in FIGS. 45 and 49, is situated between a sheath fluid supply bottle 852 and a fluid filter 854 downstream therefrom. The de-bubbler 850 includes, for example, a linear polyethylene or polypropylene bottle, such as a NALGENE™ bottle. The bottle includes a vent or cap 856 of which at least the top includes a breathable, substantially waterproof material, such as a GORE-TEX™ material. The de-bubbler 850 includes an inlet 858 toward a top of the bottle and an outlet 860 toward a bottom of the bottle. The inlet 858 is connected via a tube to the sheath fluid supply bottle 852.

In operation, sheath fluid enters the de-bubbler 850 through inlet 858 at a constant pressure, for example, at 7 psi. The pressure forces the sheath fluid out of the outlet 860. Air enters through the inlet 858, for example, when the sheath fluid supply bottle 852 is empty or substantially empty. When air enters through the inlet 858, there is an insufficient pressure to drive the water lower and out of the outlet 860 because the air escapes via the vent 856. The net effect is that no more sheath fluid is driven out of the outlet 860. When pressure sensor 95 senses little or no fluid pressure, optionally the sample pump 100 is stopped. Advantageously, as such, the instant de-bubbler facilitates "on-the-fly" sheath fluid supply bottle changes without wasting or losing sample fluid, namely, by expending sample fluid without using it. Optionally, substantially simultaneously, the control and analysis software 50 notifies the user to replace the empty sheath fluid supply bottle with a full one. Alternatively, or in addition, the flow analyzer 25 includes an optional, externally visible indicator, for example, a light emitting diode, indicates to the user to replace the sheath fluid supply bottle.

Other acceptable flow analyzers include those manufactured by Luminex Corporation of Austin, Tex., as disclosed in U.S. patent application Ser. No. 09/102,034 to Applicant, incorporated herein by reference. It is understood that, some commercially available flow cytometers, for example, the Becton Dickinson FACScan flow cytometer include an original control computer typically supplied by the flow cytometer manufacturer. However, such a flow cytometer optionally is used alternatively with the present invention using, for example, a GPIO 2-position switch box. The switch box advantageously communicates with the original control computer and the instant computer, permitting the user to select between the original control computer and the computer described hereinbelow. Such a switch box advantageously permits retrofitting of an existing flow cytometer for use in the instant invention with limited, if any, effect on performance. Thus, commercially available flow cytometers are easily used in combination with the remaining elements of the present invention, providing additional usage and/or versatility of the existing flow cytometer.

FLOW CYTOMETER DSP CONTROL

The flow cytometer has an external interface which allows a host computer to communicate with it and control it. This communication uses a standard serial or parallel protocol.

Flow Cytometer Monitoring

The flow cytometer updates its external interface with a block of parameters, which describes the current state of the cytometer. The pertinent information includes, for example, the state of all of its photomultiplier tubes (PMTs), fluid levels, etc. The software optionally reports the current status of these parameters to the user.

For example, the software optionally warns a user if the sheath fluid container is empty and requires refilling. The software optionally also warns the user if the waste fluid container is full and requires emptying. The software optionally notifies the user if a pressure-related problem exists. A "Bad Link" message optionally appears, if it is determined that the flow cytometer and the control and analysis software or DSP Interface Card firmware is not communicating properly. The software optionally monitors the flow cytometer to ensure that the setting match the calibrated settings required and set by the application.

Flow Cytometer Control

There are a plurality of flow cytometer parameters available to the serial or parallel connection interface card 15. The host computer, if needed, optionally changes at least one, most, or all of these parameters. The software is optionally capable of changing any of the appropriate flow cytometer settings available through the external interface. The changed setting is relayed to the flow cytometer and is optionally monitored as previously required. The software generally issues its request for a parameter change to the flow cytometer promptly after entering an initial request.

Flow Cytometer Event Acquisition

The flow cytometer reports, some, and preferably all light scatter events in the sample that pass through the flow cytometer and, optionally, are detected above a set threshold value. The software collects these events for analysis.

The flow cytometer sends events across the serial or parallel connection interface, for example, as list mode data. By way of illustration, events are optionally sent in blocks of 15. Fewer than 15 events and more than 15 events per block are optionally included in acceptable, alternative embodiments. Each event will contain the detected amount of light at each photomultiplier (PMT) and an optional check sum to ensure proper transmission. Each PMT event is received as, for example, a ten set linear value or other appropriate set. The software optionally discards events that produce checksum errors.

Each event optionally contains the level of scatter for any or all of the following PMTs: forward scatter, side scatter, FL1, FL2, FL3, FLA, and FLW. FL1, for example, designates fluorescence channel one and is optionally designed to capture light of a given color, for example, green. That is, the light first passes through a wavelength filter and is then collected by the FL1 PMT. FL2, for example, designates fluorescence channel two and is optionally designed to capture light of a given color, for example, orange. That is, the light first passes through a wavelength filter and is then collected by the FL2 PMT. FL3, for example, designates fluorescence channel three and is optionally designed to capture light of a given color, for example, red. That is, the light first passes through a wavelength filter and is then collected by the FL3 PMT. The PMT values are optionally reported in, for example, linear and/or logarithmic form. By way of illustration the linear values of the PMTs is, for example, between 0 and 1023, and the logarithmic values of the PMT setting may be converted from its linear form into a four-decade log scale. In this illustration, there are 1024 fluorescence channels. The software may be capable of processing, for example, 1000 events per second.

Electronic and Filter Components of the Flow Analyzer

A standard power supply switch, for example, turns the instant flow analyzer on and off. Optionally, the switch optionally automatically detects whether 110 V or 220 V voltage is being used. Otherwise, a standard adapter or external switch is optionally connected to the switch, when operated in locations outside of the United States.

Additional equipment optionally includes a sheath fluid/air filter access door to removably cover a replaceable standard air filter 85 that filters air used to pressurize the sheath fluid. An optional standard fan is used to cool the flow analyzer. Optionally, the fan is located adjacent to a wall of the flow analyzer 25 to facilitate replacement thereof. Also, an optional air intake filter is located on the bottom of the flow analyzer. The air intake filter optionally is also configured to facilitate regular or irregular cleaning thereof.

Fluidic Components of the Flow Analyzer

Disposal of, and prevention of exposure to, hazardous waste is also facilitated by the fluid dispensing and collecting components of the instant invention. Advantageously, these components together comprise a substantially completely integrated, closed fluidic system. Optionally, the instant invention includes a wall between fluidic components and electronic components.

It is understood that human sample fluids may contain hazardous infectious agents. Users of the instant invention should follow appropriate biosafety procedures when handling the samples and their containers. The waste-fluid collecting component's, advantageously, facilitate compliance with local, state, and federal biohazard handling regulations as to disposing of biohazardous waste material.

Figure 19:
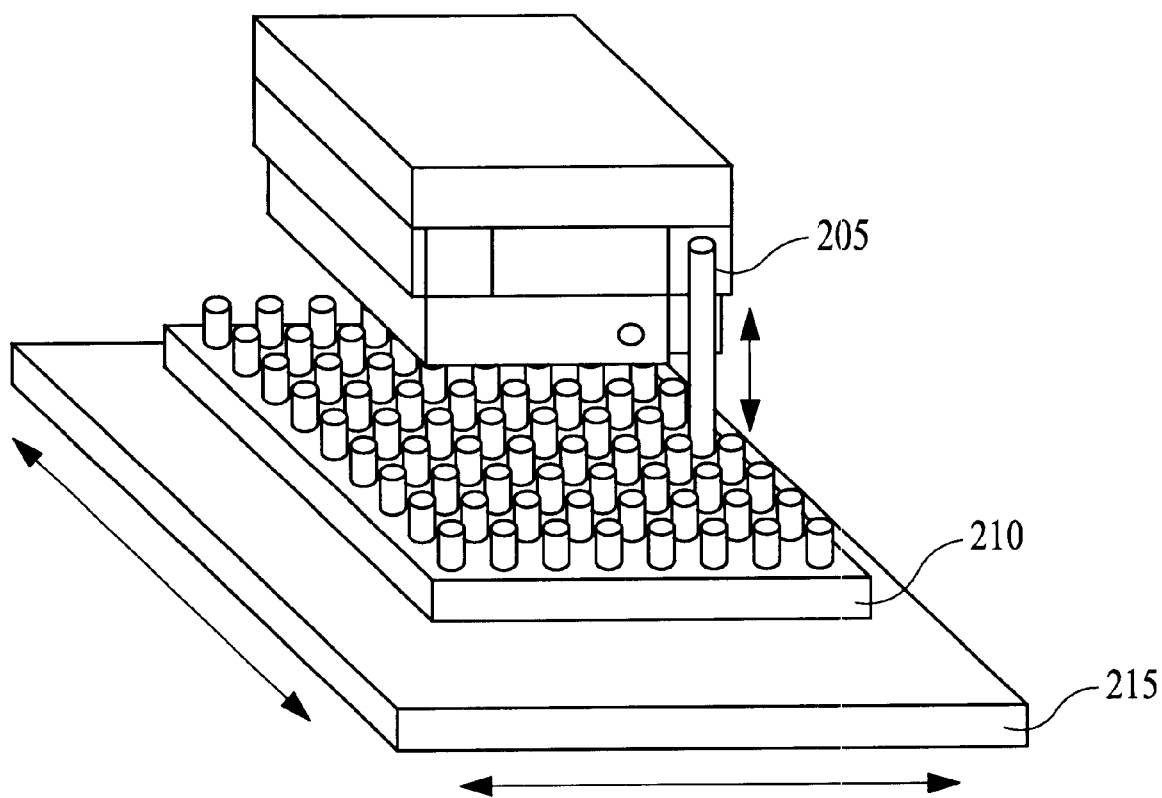
FIG. 19 is a perspective view of an illustrative embodiment of a movable plate transport cooperating with a flow analyzer.
Figure 50:
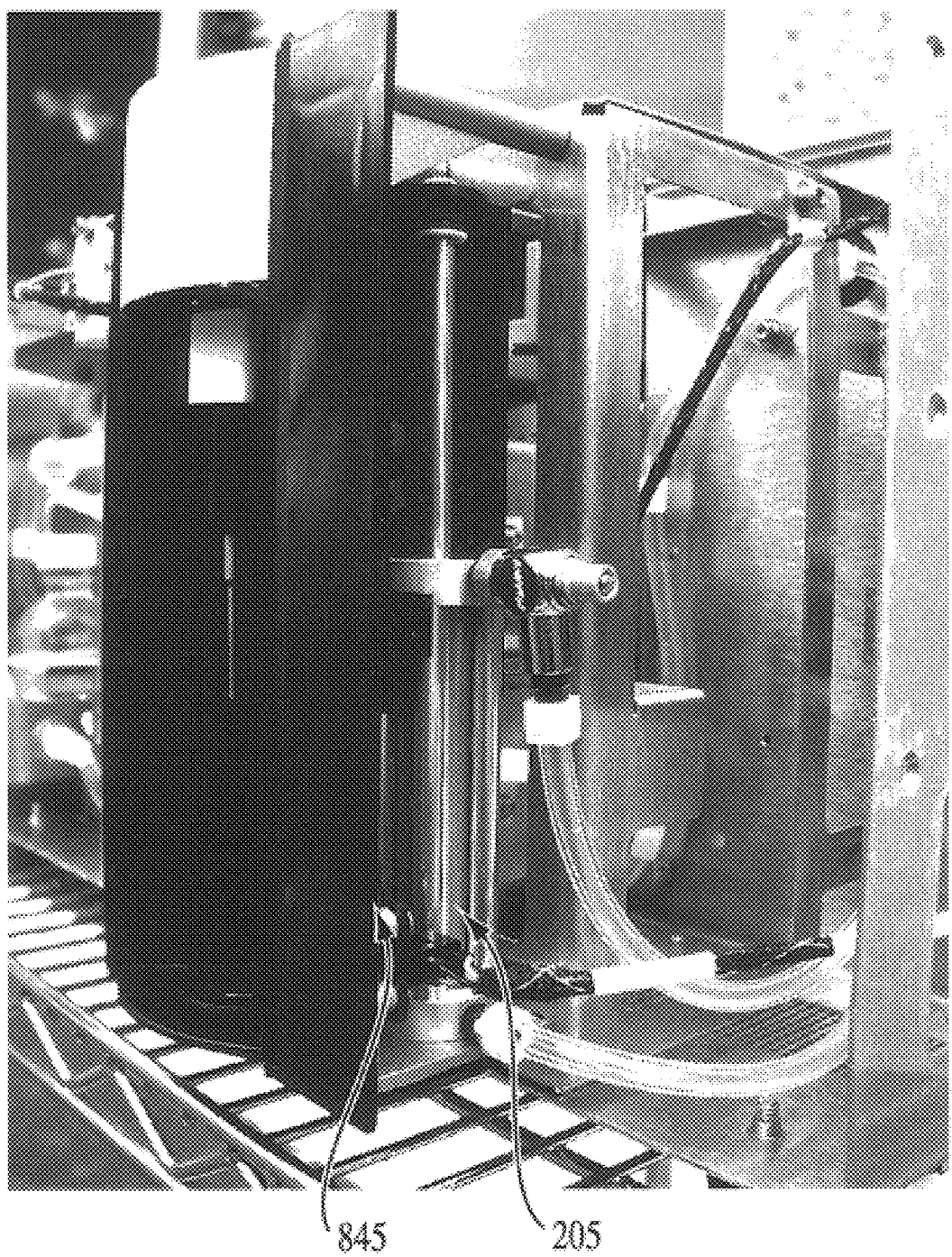
FIG. 50 is a perspective view of an exemplary optical switch according to the instant invention.

The instant flow analyzer 25 optionally cooperates with standard laboratory automation equipment. For example, as shown in FIG. 19, a standard integral pneumatic actuator and sample aspirator 205 moveable along a vertical Z-axis optionally samples from wells of a standard microtiter plate 210 by incorporating a standard movable horizontal X-Y plate transport platform 215 underneath the flow analyzer 25. For example, an optional standard optical switch 845, as shown, by way of example, in FIG. 50, includes a tab which closes the switch when the arm of the pneumatic aspirator is fully or substantially fully extended in the down position. Optionally, when the optical switch determines that the arm is in the fully extended position, the sample pump 100 is automatically shut off.

Optionally, travel of the pneumatic actuator is optionally interrupted by substantially any obstruction, thereby preventing damage or injury to the user and/or the system. A standard communications port operatively connects the flow analyzer to the plate transport. Such a cooperating aspirator advantageously provides true "walk-away" capability. By extension, multiple flow analyzers, for example, eight or more flow cytometers, all connected to a single personal computer, are optionally configured to work in parallel or in series to address the needs of extremely high throughput operations.

Alternatively, the movable horizontal X-Y plate transport platform 215 optionally supports the microtiter plate 210, instead of the flow analyzer 25. In yet another embodiment, a plate transport optionally is obviated by an aspirator moveable in three directions, for example, each mutually perpendicular from another. For example, the above-mentioned vertically moveable pneumatic sample aspirator 205 optionally is operatively connected to at least two rack and pinion gear sets. moveable in a horizontal X-Y plane. As another example, the above-mentioned vertically moveable pneumatic sample aspirator 205 is optionally operatively connected to a pneumatic piston moveable in a horizontal X-direction and to a pneumatic piston moveable in a horizontal Y-direction.

For example, a sample aspirator carriage is optionally located on a face of the flow analyzer or in communication therewith. The carriage transports the sample fluid from the test tube to the cuvette of the flow cytometer. Upon operation, the carriage advantageously automatically drops to the microtiter plate in place for sample retrieval.

A standard sample fluid tube holder grips each microtiter tube in place beneath the sample aspirator carriage. When using the plate transport, however, the sample fluid tube holder is removed for the sample aspirator carriage to automatically retrieve sample from the plate transport.

A standard cover of the sample aspirator carriage optionally encases or covers a standard fitting, such as a Cheminert fitting manufactured by Valco Instruments Co. Inc. of Houston, Tex., which is optionally loosened to allow adjustment of the length of a sample injection tube.

A standard sample injection needle or syringe is optionally housed in, for example, a stainless steel tube or other material. Optionally, the location of the sample injection needle is determined to facilitate replacement thereof, if damaged. For example, the needle is optionally accessed via a front mounted door to facilitate replacement of the seal on the needle by a user. The sample injection tube or hose connected to the sample injection needle carries sample fluid from the microtiter tube into the interior of the flow analyzer 25. Advantageously, if the end of the tube becomes worn or frayed, the user may conveniently clip off the frayed end and re-adjust the tube length.

Figure 12:
FIG. 12 is a perspective view of an illustrative embodiment of a fluid bag and a vial.
Figure 13:
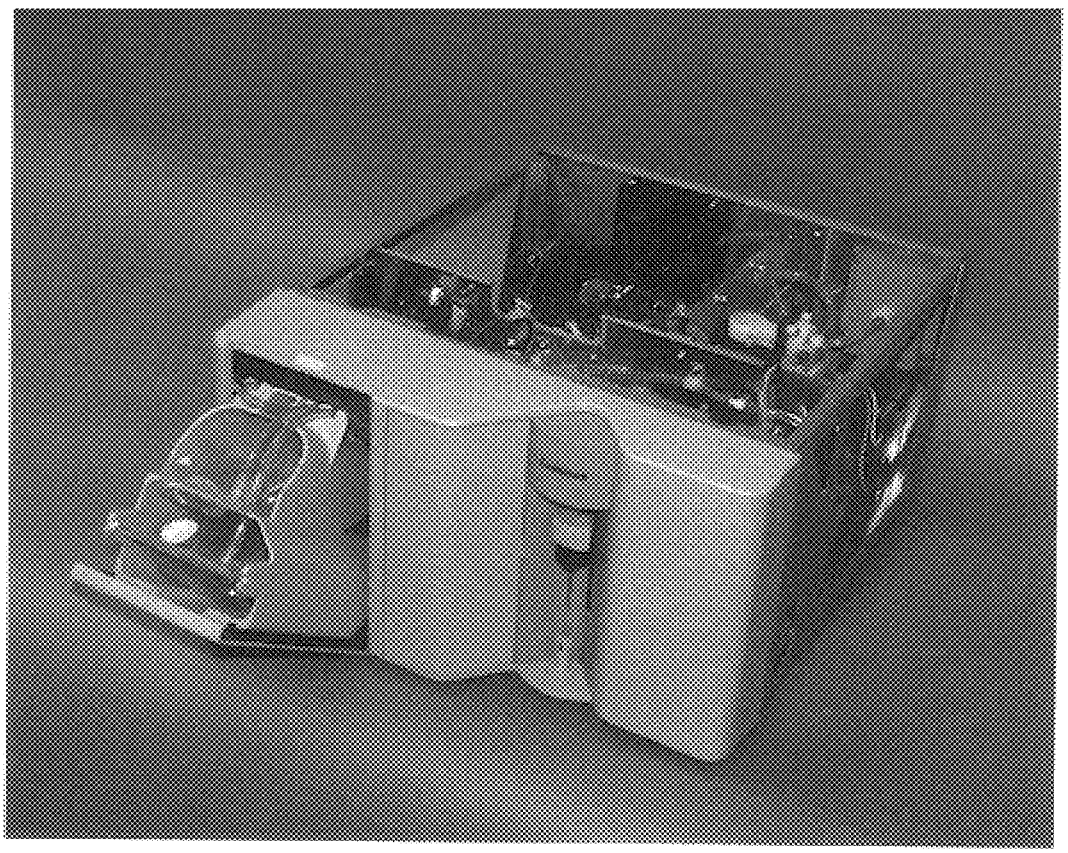
FIG. 13 is a perspective view of an illustrative embodiment of the fluidics system in the instant flow analyzer.

A sheath fluid reservoir and a waste water reservoir optionally stores sheath fluid 160 and/or waste water, respectively. The reservoirs include, for example, polyethylene bags 75, 110. Alternatively, the reservoirs include, for example, internally or externally situated bottles. Advantageously, implementation of the reservoirs using external bottles facilitates filling the same and permits a variety of sized bottles to be used. A sheath fluid bag 75 is optionally pressurized, thereby forcing fluid into the system. As shown in FIG. 12, optionally, each bag includes a semi-permeable membrane patch level sensor, for example, at a bottom thereof. The semi-permeable membrane patch includes, for example, a standard GORE-TEX® material, as manufactured by W. L. Gore & Associates, Inc. of Newark, Del. The sensor advantageously releases air pressure, when fluid level drops below the patch, thereby advantageously preventing any significant quantity of air from entering the system. When the electronic pressure sensor detects a drop in pressure, optionally, the operator is optionally prompted to replace the bag. A compartment containing the sheath fluid/waste water bag of the flow analyzer is optionally accessed by a user via an access door on the face of the flow analyzer.

Standard high volume connectors are optionally located on a side of the flow analyzer 25 to offer high volume users the option to connect directly to sheath fluid supply containers and waste water containers, for example, 20 L standard containers, rather than use the smaller internally stored-sheath fluid/waste water bag.

A standard pressure regulator is optionally located behind an access door, for example, closest to the sample aspirator carriage. The pressure regulator is optionally pre-set by a manufacturer thereof, and adjustments thereto optionally being made with the aid of Technical Assistance staff.

A syringe pump 100 optionally creates a vacuum that transports the sample fluid from the sample aspirator carriage and the flow cuvette. The syringe pump 100 is optionally located in the same compartment as the pressure regulator. Because positive pressure need not be used to load the sample fluid into the flow analyzer 25, advantageously the use of dangerous aerosols are optionally reduced or avoided.

To achieve system miniaturization, smaller than ordinary fluid reservoirs are optionally used. However, doing so necessarily entails conserving sheath fluid 160. A microcontroller optionally accomplishes this purpose, for example, by calculating substantially the exact interval prior to sample injection that flow must begin to achieve hydraulic stability at any measured pressure. As soon as an assay is complete, flow is optionally halted, and any remaining sample fluid is optionally diverted to the waste fluid bag.

Laser and Optical Components of the Flow Analyzer

As mentioned above, the flow analyzer 25 includes a co-planar laser/detector array. Fluorescent signals are delivered to optical amplifiers, such as avalanche photodiodes, where waveforms are photoelectronically converted and amplified for analysis by the DSP. Standard algorithms derived from the wireless communications industry optionally function with the DSP to greatly increase the signal-to-noise ratio and, therefore, sensitivity. The instant flow analyzer optionally includes interrupt driven, fixed rate sample acquisition into circular buffers, which provide zero inter-event dead time. That is, such circular buffers 30 allow the processing of patient samples with wide analyte concentration ranges without fear of losing rare events because of a slow processor.

Substantial miniaturization of the flow analyzer is optionally achieved using standard diode lasers as the light sources 120 for the flow analyzer 25. The laser/detector array, for example, two lasers and four detectors, are arranged in a co-planar configuration so as to allow close working distances, and a single-filter light path to, for example, the avalanche photodiodes. Optionally, more than one filter operatively connects a detector and a corresponding optical amplifier, such as an avalanche photodiode.

The laser assemblies are optionally inaccessible to the user. Optionally, all required maintenance are performed by a system factory.

As mentioned above, advantageously, lenses, mirrors, and detectors common to current flow cytometers for light collection are optionally replaced with a hexagonal cuvette, in the instant invention. Such a hexagonal cuvette provides a flat air-to-glass interface for the laser diodes and the detectors.

Optional Standard Lab Equipment

Equipment, for calibration of the instant invention, include, for example, a standard bath sonicator, probe sonicator and/or a standard vortex. Additional materials for calibration optionally include standard calibration beads, such as FlowMetrix Calibration Microspheres 41-55001, and a standard read tube, such as a FACS-compatible read tube.

SYSTEM OPERATIONS

The system is powered up to a known state and, optionally, indicates error conditions if errors occur during the power-up. A user powers up a flow cytometer, and optionally its host computer, including any peripherals. At the end of the power up sequence, the software is in a state such that the user can begin to operate the system and software with proper controls. available. The software advantageously and optionally indicates whether any flow cytometer errors occurred during power up and/or whether the flow cytometer communications were not available.

The software is optionally configured to allow a user or operator to set up and define a new sample diagnostic run. The user optionally invokes a new run via a graphical interface of the application. The software, for example, presents the user with an entry form containing fields pertinent to a new run. By way of illustration, the form includes a field for the user's name, a field for the number of samples contained in the run, and/or a field for the description of the run.

Standard maintenance and calibration procedures for the flow cytometer are optionally followed. By way of example, a calibration procedure for the instant invention optionally includes adjusting PMT voltages such that microspheres will advantageously produce similar readings across different flow cytometers of the same or different brands and/or models. For example, the user processes a sample containing a standard calibration solution having, one, two, three or more calibration bead types. Known, predicted, peak measurements, for example, side scatter, of FL1, FL2, and/or FL3 are targets for the calibration process, for each calibration bead type. Advantageously, the software automatically, or by user demand, makes adjustments to the flow cytometer, while the calibration sample is running until these target goals are achieved or within a feasible time period from the conclusion of the calibration run. That is, for example, the software is optionally calibrated using automatic adjustments implemented in the software such that all bead types are recorded in their predicted regions. To this end, the software optionally adjusts the PMT so that the measured peaks of the calibration bad types come to within one, two, three, four, five, or more channels of their target values. When using avalanche photodiodes as the optical detectors, optionally, calibration software advantageously computes or applies a temperature compensation table so as to ensure that the avalanche photodiodes have substantially constant gain at all or substantially all temperatures in a standard operating range.

METHOD OF OPERATION OVERVIEW

Figure 41:
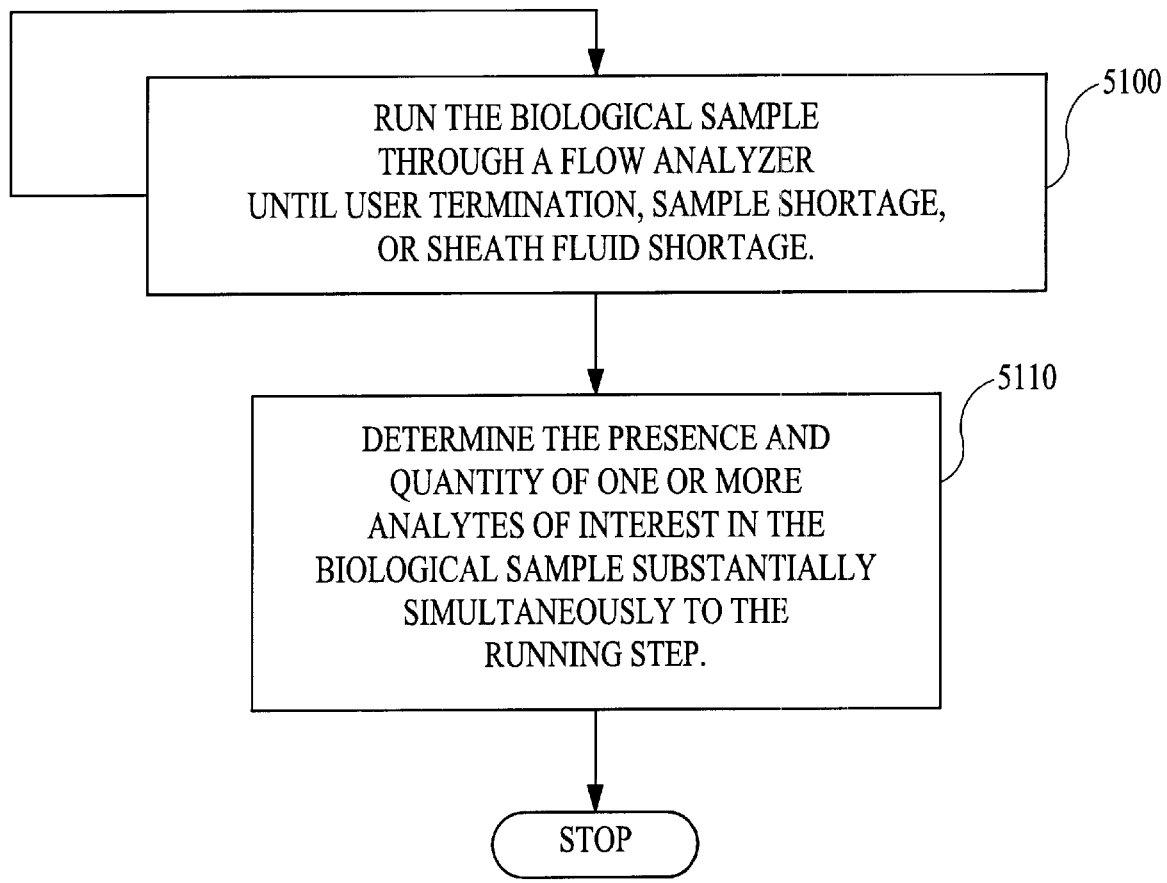
FIG. 41 is a flow chart of an illustrative embodiment of a method of operation for the instant diagnostic system.
Figure 42:
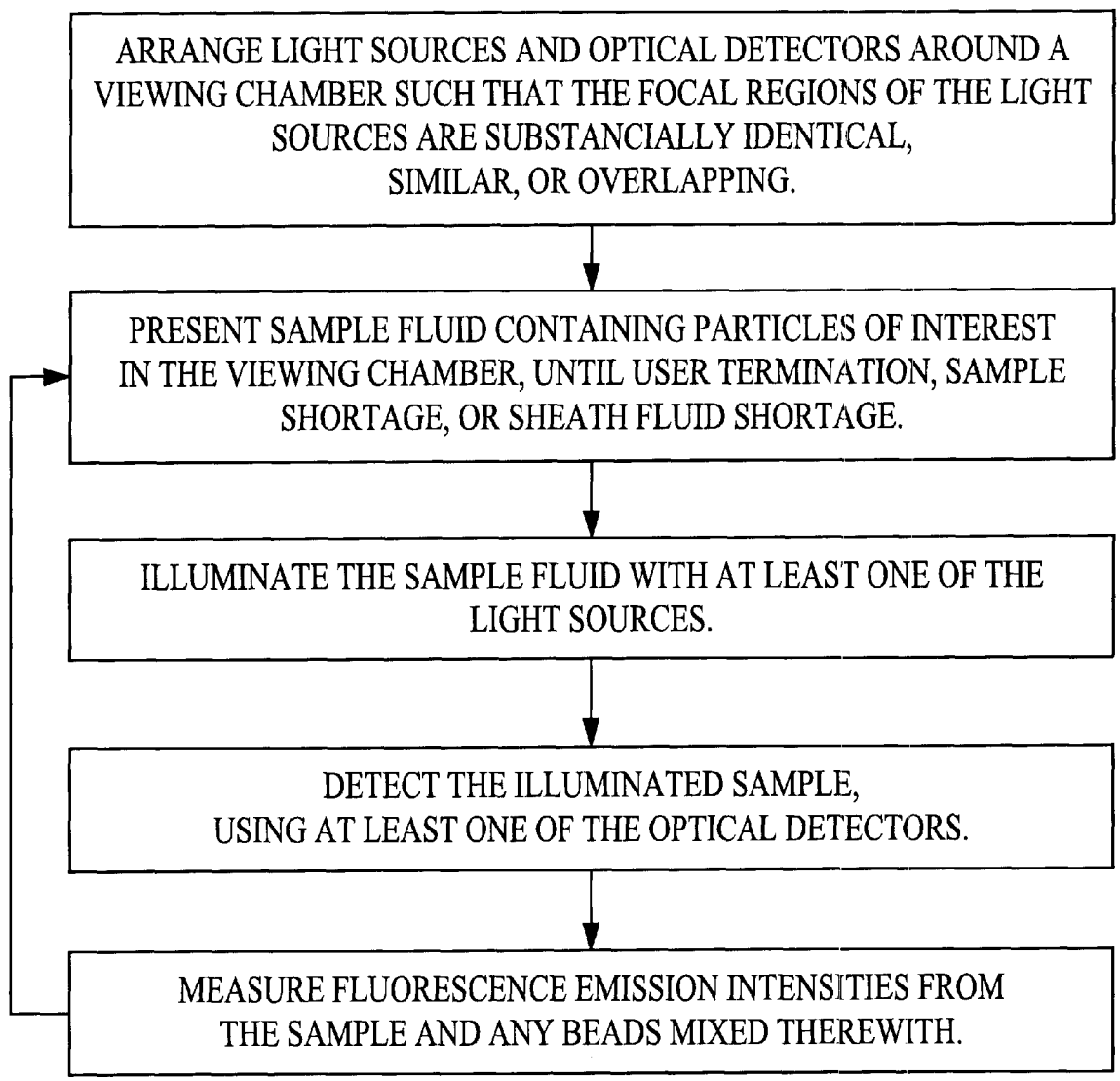
FIG. 42 is a flow chart of an illustrative embodiment is of a method of operation for a flow analyzer consistent with the instant invention.

An illustrative general method of operation of the diagnostic system includes the steps as shown, by way of example, in FIG. 41. In step S100, a biological sample is run through a flow analyzer until user termination, sample shortage, or sheath fluid shortage. In Step S110, the presence and quantity of one or more analytes of interest in the biological sample substantially simultaneously to the running step. Acceptable alternative embodiments of the method of operation are optionally found in U.S. Ser. No. 09/102,034 to Applicant, and U.S. Ser. No. 09/000,286, to Applicant, Jerrold R. Fulton, and Mark B. Chandler, both references being incorporated herein by reference.

CONTROL AND ANALYSIS SOFTWARE OVERVIEW

The control and analysis software controls operation of the flow cytometer and performs real-time digital analysis of one or more biological samples for one or more analytes of interest, simultaneously or substantially simultaneously including sequentially. Real-time analysis according to the instant-invention is intended to include, but is not limited to, determining an identity and quantity of, at least one of and, optionally, each, analyte of interest in a biological sample by substantially simultaneously or substantially contemporaneously performing the following steps or sub-steps. Microsphere or particle classification data and reactant-analyte complex measurement data are collected. For example, each microsphere are classified according to its subset of microspheres. The amount of reactant-analyte complex associated with each subset of microspheres are quantified.

The software operate on any standard operating system platform, for example, Microsoft Windows 95 operating system located on a personal computer, standard network, or other global network. Alternate operating platforms include Solaris, Linux, Java, Mac OS, and/or IBM OS/2, for example. A controller optionally integrates the software and the communications interface to the flow analyzer 25.

Figure 20:
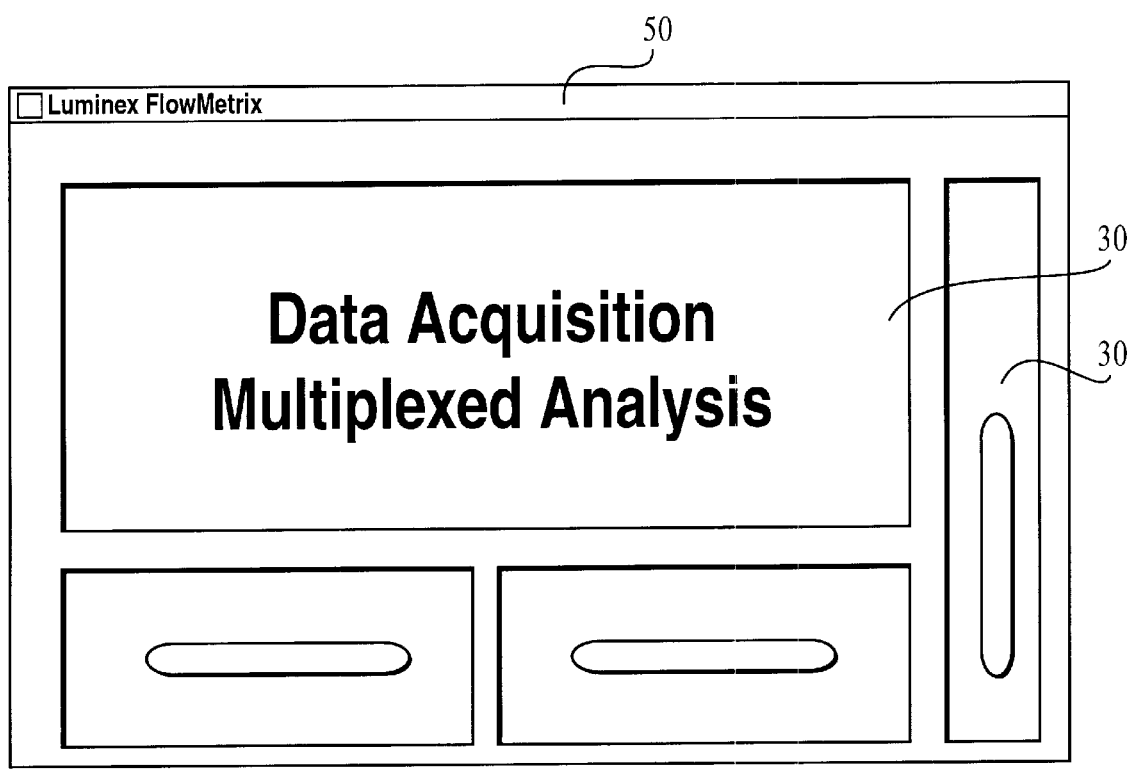
FIG. 20 is an illustrative embodiment of an initial screen display of the instant control and analysis software.

The control and analysis software 50 according to the present invention includes two modules, as illustrated in FIG. 20. One module is called Data Acquisition 300, and the other one is called Multiplexed Analysis 305. The control and analysis software 50 communicates with appropriate standard libraries. These libraries, for example, include an application programming interface library, such as a LumAPI library, and/or a mathematics library, such as a MHMath library, both of which being described hereinbelow.

The control and analysis software 50, for example, includes a standard interface used to collect data from the flow cytometer 25 via the serial or parallel connection interface card 15. The control and analysis software 50 initializes and obtains status information from the flow cytometer 25. It also permits user entry of assay kit information, including bead subset data. For example, if an Immunoglobulin G, A, M Isotyping Assay were intended, standard kit information concerning the Ig GAM Assay Kit produced by Luminex Corporation is optionally entered.

The control and analysis software 50 instructs the flow cytometer 25 to process a biological sample. The software 50 displays a graph of an appropriate linear trend line for prediction. A Logit Log transformation, for example, is used to calculate such a linear trend line for prediction. Such a calculation is as follows $$\text{Logit}\left(\frac{MIF}{MIFo}\right) = \ln\left(\left(\frac{MIF}{MIFo}\right) \Big/ \left(\frac{1-MIF}{MIFo}\right)\right)$$

where $MIF_o$=negative control, and MIF=control

The predicted value using a Logit Log transformation, is $$10^{\ln((\frac{MIF}{MIFo})/(\frac{1-MIF}{MIFo}))} - \frac{yintercept}{slope}$$

The intercept and/or slope values are calculated using the polynomial trendline routines in a standard mathematics library, such as MHMath. The software 50 produces a report indicating success or failure of detection of analytes of interest in each sample and, optionally, reasons for failure. The report is, for example, in tabular form. The report, for example, includes a header with pertinent run information such as data, operator, and/or a description of the run. For example, the report optionally includes concentration levels of large G, A, M, for patient samples, if an Ig G, A, M assay were run. The software 50, for example, produces an x-y graph displaying $$\text{Logit}\left(\frac{MIF}{MIF_o}\right)$$

on the y-axis and $$\text{Log}\left(\frac{mg}{dL}\right)$$

on x-axis. A standard trend line from, for example, the first control value of a concentration level to, for example, the fifth control value of a concentration level is optionally drawn.

The control and analysis software 50 guides an operator through steps necessary to complete a diagnostic run. The software, for example, allows the operator to define a new sample diagnostic run. The user invokes a new run through the software interface. The system dictates the order in which the samples are processed, preventing the user from randomly selecting which sample is processed during a run. Optionally, the system permits the user to determine the order of the samples to be processed. The operator or user optionally manually loads the flow cytometer 25 or allows automatic sample acquisition via a movable microtiter plate transport platform 215.

DATA ANALYSIS

The software advantageously includes a method by which a user initiates capture of flow cytometer events.

In use, there may be some spectral overlap in the excitation curves of one or more bead identification fluorescent dyes and one or more analytes of interest identifying dyes. For example, a green fluorescent dye identifying an analyte of interest and an orange fluorescence dye, at least partly identifying a bead subset, may suffer from spectral overlap of the respective excitation curves. Alternatively, for example, an orange fluorescent dye identifying an analyte of interest and red fluorescent dye and an infrared fluorescent dye identifying a bead subset are used. In such a case, for example, the orange fluorescent dye and the red fluorescent dye may suffer from spectral overlap of the respective excitation curves.

To correct this, a standard color compensation function to account for the amount of green fluorescence present in the orange reading and vice-versa is optionally included in the software 50. Color compensation optionally is applied immediately to the events as received using a standard color compensating algorithm. Thus, events optionally are adjusted to indicate their actual levels of orange and green in real-time. The performance of the color compensation process optionally is less than 1000, equal to 1000, or greater than 1000 events per second.

Advantageously, the system optionally ignores events due to aggregated beads and other events that do not correspond to the size of a single bead. For example, the system optionally ignores events by gating the side scatter collector to a narrow range defined by the assay after the events have passed through the color compensation function. Optionally, the output of the gating process optionally includes events corresponding to a uniform shape of a single bead of known diameter, for example, 5.5 $\mu$m. Optionally, the performance of the gating process optionally conforms to a rate of less than 1000 events per second, 1000 events per second, or more than 1000 events per second.

Bead Identification

The software 50 collates or categorizes bead types based, at least in part, on color content. Naturally, in addition, the system optionally categorizes bead types based on other or additional factors, such as size and magnetic coding.

Bead identification includes a function of the fluorescence channels FL2 and FL3 parameters for a given event. Advantageously, I predefined regions for each bead in the system described in an x-y grid. The FL2 values, for example, make up the x-axis, the FL3 values, for example, make up the y-axis. The units along the axes optionally are units of fluorescent channels or fluorescence. For example, each axis includes 1024 fluorescent channels. Plainly, each axis alternatively can have more than 1024 fluorescent channels as dyes with greater emission spectrum definition become available or as greater emission spectrum definition becomes possible with present, standard dyes. The bead identification process, for example, maps an event to a specific bead subset identification number and optionally dismisses the event as not being a valid bead. A classified bead includes a bead identification from, for example, the FL2 and FL3 values and a FL1 measurement designating the presence and/or amount of analyte of interest on the bead.

The event collection and bead identification process is optionally capable of identifying less than 1000 beads per second, 1000 beads per second, or greater than 1000 beads per second.

Calculating Bead Statistics for each Bead

Once the software has identified the event as belonging to a specific bead classification, bead statistics are optionally calculated.

For example, account statistic optionally tracks the number of beads of a given bead subset classification that have been acquired during the current sample. Plainly, the sum of all bead counts must equal the number of beads collected in the current sample. Again, performance is optionally less than, equal to, or greater than 1000 events per second.

A FL1 Linear Mean determination optionally is performed after an event is identified as belonging to a specific bead classification. FL1 Linear Mean, for example, equals the sum of all FL1 linear values of a given bead type divided by the count of beads collected for that type. Performance, for example, is as discussed above.

A FL1 Linear Standard Deviation is optionally calculated. It, for example, includes the standard deviation calculation for the linear FL1 values of a given bead type as is done for each bead type in the current sample after an event has been identified as belonging to a specific bead classification. Performance, for example, is as discussed above.

A FL1 Linear Coefficient of Variation (Linear CV) optionally is also calculated. It, for example, includes the standard deviation of linear FL1 values as represented as a percentage of its linear mean. Before performing this calculation, the software optionally calculates the linear standard deviation and linear mean measurements for the given bead classification. The linear CV measurement for each bead type in the current sample is then calculated. Performance is optionally as discussed above.

A FL1 Linear Peak optionally is also calculated. It, for example, includes the linear FL1 value having the most occurrences during the current sample for each bead type, after an event is identified as belonging to a specific bead classification. Performance optionally is as discussed above. Linear peak measurement equals, for example, integers from 0 to 1023, assuming 1024 fluorescent channels. Plainly, acceptable linear peak measurement values are more or less depending on the number of fluorescent channels.

The above-mentioned FL1 calculations are, for example, used to ascertain statistically significant concentration levels of an analyte of interest. Optionally, such ascertaining includes comparisons to background FL1 concentration levels in a sample.

DATA ACQUISITION MODULE

The Data Acquisition module 300 acquires fundamental data coming from the machine, and is not necessarily bead specific. That is, the Data Acquisition module 300 yields statistics for, by way of illustration, the side scatter channel and/or the different fluorescent channels, such as, Fluorescent channel 1 (FL1), Fluorescent channel 2 (FL2), and Fluorescent channel 3 (FL3) using standard techniques. The fluorescent channels represent the state of fluorescence of a detected bead. Thus, the Data. Acquisition module 300 optionally yields data that relate to an event. For example, data provided by the Data Acquisition module 300 includes, for example, a cell that has been stained, a fluorescently labeled bead, or an indication that no beads are present.

The Data Acquisition application module 300 includes, for example, a simplex analysis application module or option for use with, for example, single bead sets or other particles or cells. Such a simplex analysis option facilitates the initial setup of an experiment when settings, gates, and/or reagents, for example, have not yet been determined.

The simplex option includes one or more templates, files, or folders that contain stored PMT settings, gates, reagents, bead set values, detection regions, and/or spectral overlap compensation settings for use in experiments. By way of illustration, it is to be understood that the photomultiplier settings are optionally replaced with avalanche photodiode settings or a combination of photomultiplier and avalanche photodiode settings. The simplex analysis option optionally includes a provision whereby a user stores all events, gated and non-gated, to a folder or only those events passing through designated gates. The user optionally selects an established template, establish settings and save them as a new template unique to the user's needs, and/or proceed to the experiment without creating a template. As to the third selection, when the experiment is completed, the user optionally saves the used settings as a new template or folder. Settings, for example, include assay description, assay operator, number of gated events to collect per sample, flow rate, and/or number of samples. Upon completion of exercising the simplex analysis option, the software is optionally ready to acquire and analyze data from the flow analyzer.

FEATURES COMMON TO MULTIPLEXED ANALYSIS MODULE AND THE DATA ACQUISITION MODULE

Fluorescent channel 1, Fluorescent channel 2 and Fluorescent channel 3, for example, include fluorescent signals of same or different wavelengths. A light source, such as a laser, excites the fluorescent signal at one wavelength, but the fluorescent signals then emit fluorescence at, for example, different wavelengths detected at different windows or filter units. The fluorescence data is inputted into the software for multiplexed analysis. The invention classifies a data event as, for example, a bead or cell data unit, using, for example, gating on a forward light-scatter channel and/or a side light scatter channel. For example, the beads are identified by using a gating filter calibrated by a user or a manufacturer to appropriately identify a range of forward and/or side light scatter data associated with a bead type. Using such a filter on any incoming event, for example, if a side light scatter channel does not read a meaningful event, then the invention optionally throws out the event and does not collect data.

Figure 21:
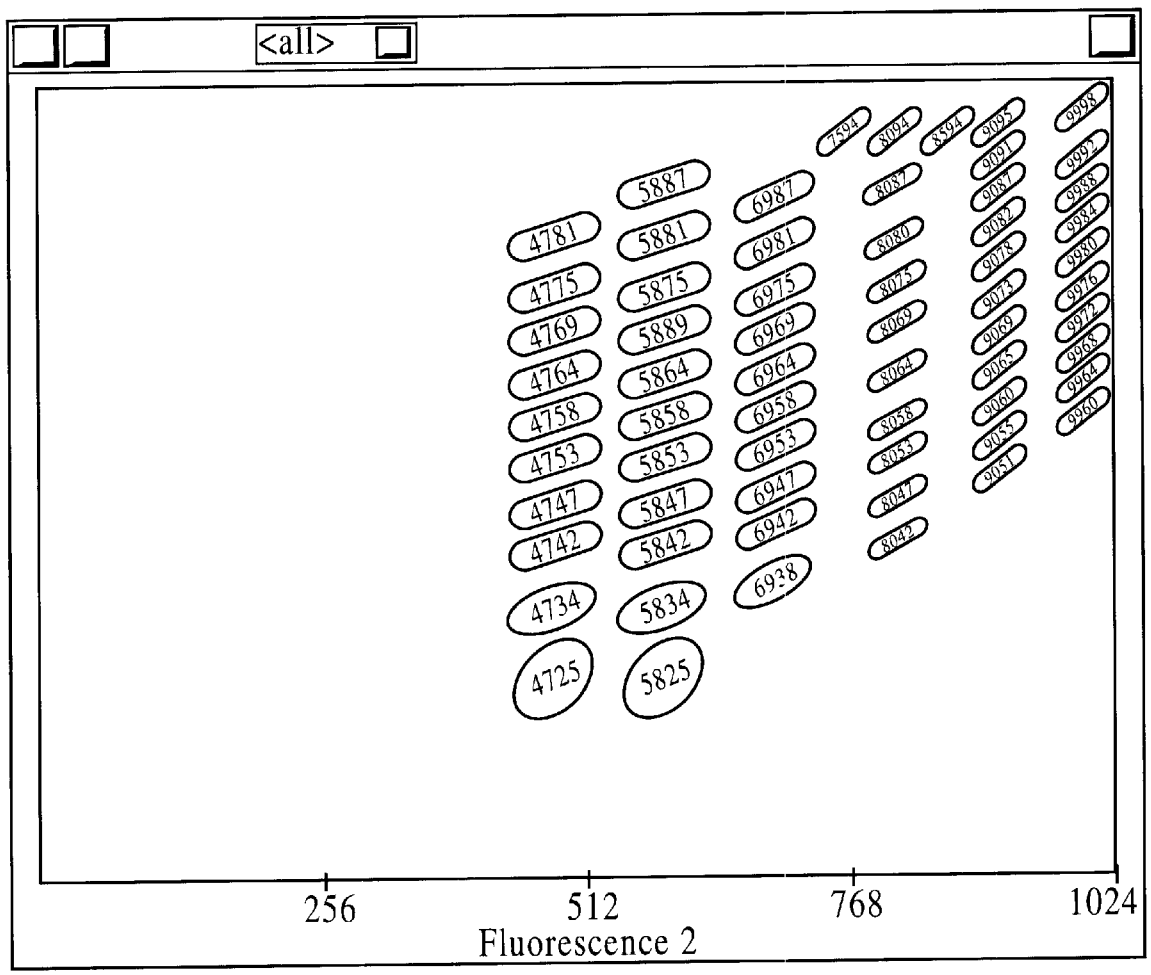
FIG. 21 is an illustrative embodiment of a grid having predetermined bead regions of characteristic fluorescence emissions.

Bead data are placed or stored in a logical bucket, or a database. Signals from the bead are passed through, for example, the side light scatter channel. If the bead (beads) passes the side scatter filter, then the bead type is optionally determined. The FL2 and FL3 channels may yield varying signals, optionally corresponding to predefined regions associated with respective bead types, for example. So if, for example, FL3 on the Y axis and FL2 on the X axis are plotted in a spectral table, each bead optionally has a predefined spectral region. This predefined region optionally includes an elliptical region of where beads of a given subset are designated to fall into, for example, as shown in FIG. 21. These regions may suffer from spectral overlap because of FL1 signals, for example, thereby rendering the bead regions indistinguishable. By way of illustration, each bead region has an alphanumeric identifier. Each identifier optionally corresponds to a respective analyte of interest. If a processed signal is identified as belonging to a particular bead region, then automatically, its alphanumeric identifier and analyte of interest are known, and appropriate tracking variables are optionally updated.

So, while these events are processed in real-time, color compensation to correct spectral overlap are optionally performed to determine the real fluorescent values for FL2 and FL3. Then, the bead fluorescence are matched with the spectral table to determine whether they fall into one of the predefined bead subset regions. If the fluorescence does not match then the data is not included in the statistics. Examples of errors include beads that fall slightly out of the regions, trash, spurious noise, and/or the like.

It is to be understood that the above processes are performed using the simplex option or a multiplexed analysis option. Data are recorded to, for example, Flow Cytometry Standard (FCS) files for list mode analysis and/or spreadsheet compatible files, such as CSV files, for spreadsheet analysis.

By way of non-limiting illustration, the Data Acquisition application module 305 and/or the Multiplexed Analysis application module 305 includes a graphical display 320, for example, as shown, by way of example, in FIG. 22 and as described hereinbelow. For example, the graphical display 320 includes, as shown, by way of illustration, in FIG. 23, a title bar 325 indicating, for instance, the experiment folder or template name currently open. The display includes, as shown, by way of illustration, in FIG. 23, a main menu bar 330 having a number of options, such as pull-down menu options. For example, the options include one or more of the following.

Title and Main Menu Bar

Figure 24:
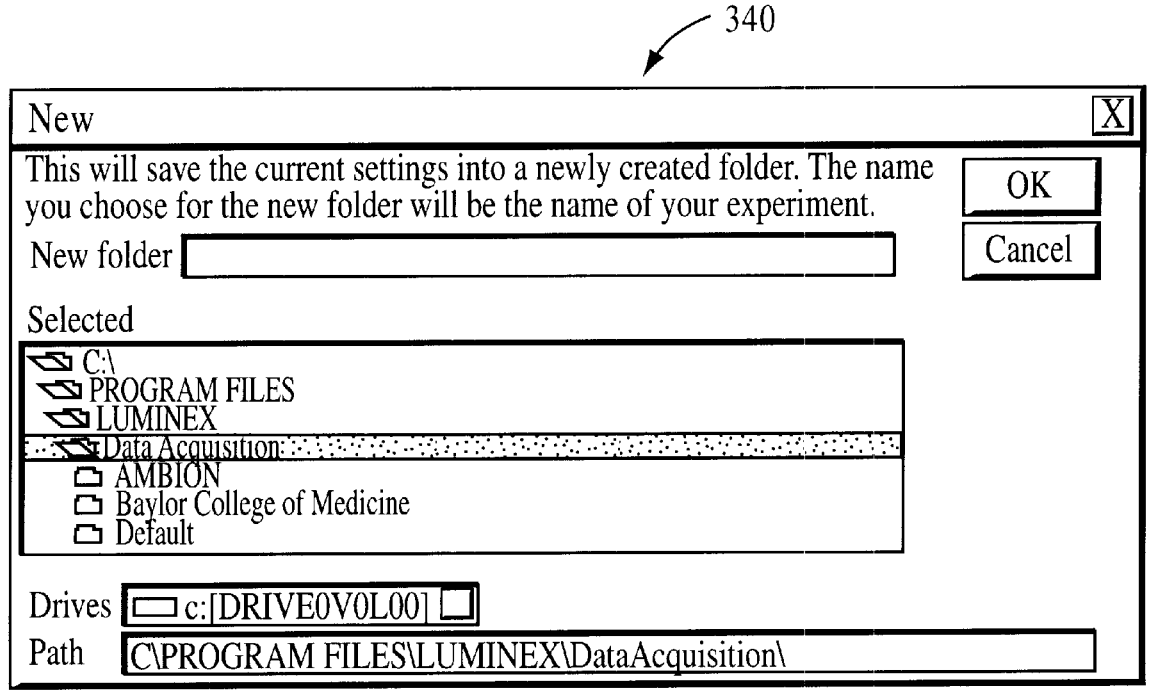
FIG. 24 is an illustrative embodiment of a new folder graphical display window.

The Main Menu Bar 330 optionally includes a "Folder" option 335, which, in turn, includes one or more of the following choices. A "New" folder choice 340 provides means or functionality for creating a new experiment folder using standard techniques that are provided, for example, in a windows-like environment. This means also include choosing a new experiment folder as shown, by way of illustration, in FIG. 24. This means also include choosing a folder or template, choosing a location for the new experiment, and/or naming the folder in which the data and experiment settings will be stored. An "Open" folder choice provides means for opening an existing folder. A "Save" folder choice provides means for saving a folder with a current name. A "Save As" folder choice includes means for saving the folder with a new name. A "Print" folder choice provides means for selecting which components to be printed by, for example, selecting or checking the appropriate box, such as, for a results table, a dot plot, and/or a histogram. A "Create Template" folder choice includes means for saving PMT settings, gates, regions, etc., as a template file to be used in future experiments. Note that experimental data need not be stored through this option, but rather template settings.

Figure 23:
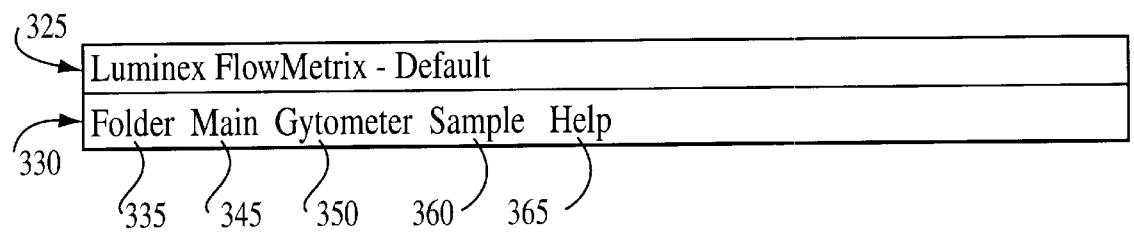
FIG. 23 is an illustrative embodiment of a title bar and main menu bar.

A "Main" option 345, as shown, by way of illustration, in FIG. 23, includes means for returning, the user to an opening screen or window for the control and analysis software.

Figure 25:
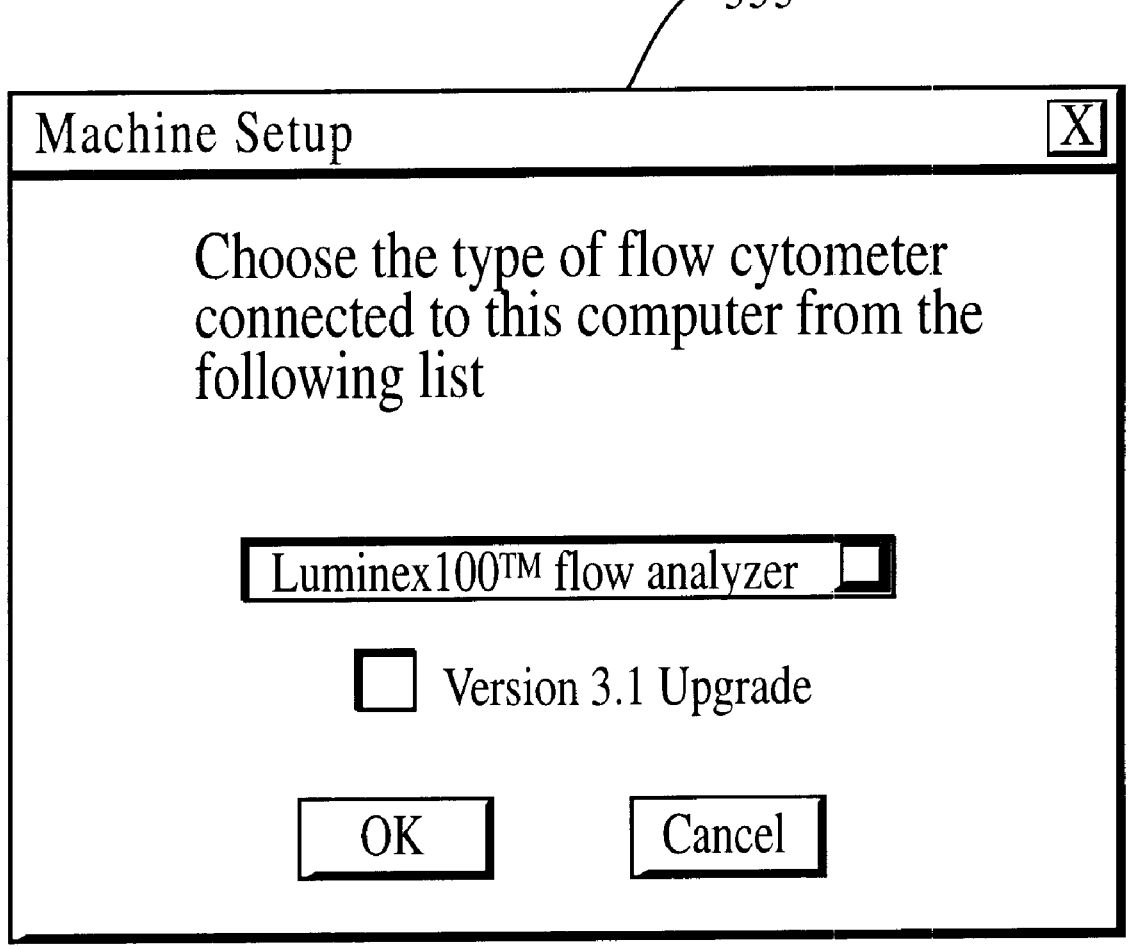
FIG. 25 is an illustrative embodiment of a machine setup graphical display window.

A "Flow Analyzer" or "Cytometer" option 350, as shown, by way of illustration, in FIG. 23, includes one or more of the following choices. A "Machine Set Up" choice 355, as shown, by way of example, in FIG. 25, provides means for selecting among a number of flow analyzers having characteristics included in the software. A "Calibrate" choice includes means for calibrating the flow analyzer and/or stores in a data file the information obtained. By way of example, this operation is performed advantageously immediately upon installation of the analyzer and, for instance, monthly thereafter. A "Connect" choice includes means for establishing an initial connection between the software and certain flow analyzers, such as the Becton Dickinson FACSCalibur model. Note that other flow analyzers, such as the Luminex Corporation's LUMINEX100™ model, do not require this procedure.

A "Sample" option 360 provides means for displaying data from a previous experiment. For example, the "Sample" option includes a "Load Data" choice. After an existing folder is opened and one or more samples are highlighted, the "Load Data" choice, which includes means for retrieving data histograms, and/or dot plots to a display or printer. Optionally, this "Load Data" choice includes means for displaying data incrementally.

A "Help" option 365 includes means for getting help relative to common procedures, errors, and/or frequently asked questions.

Results Table

Figure 22:
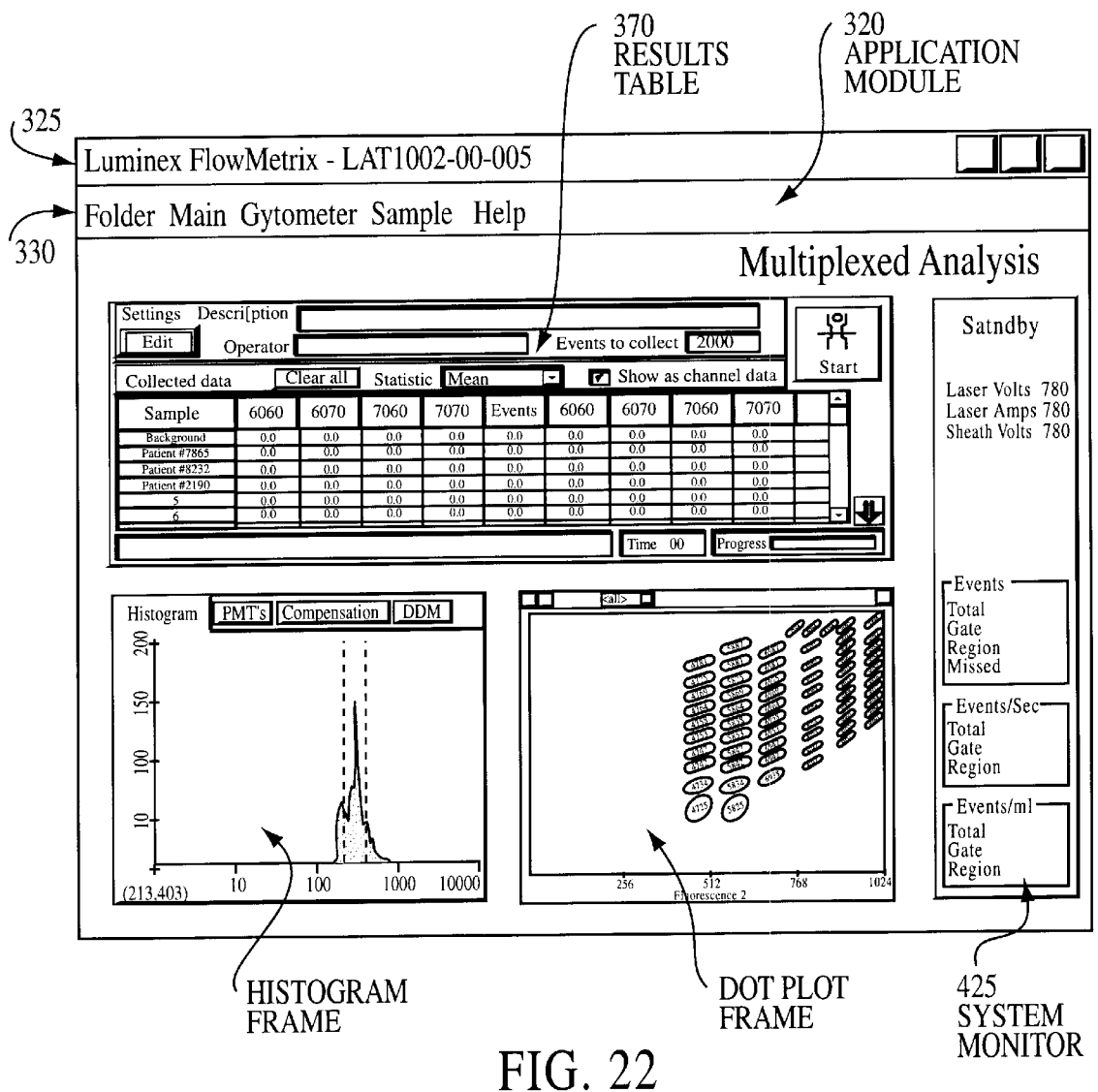
FIG. 22 is an illustrative embodiment of an overall screen display.
Figure 26:
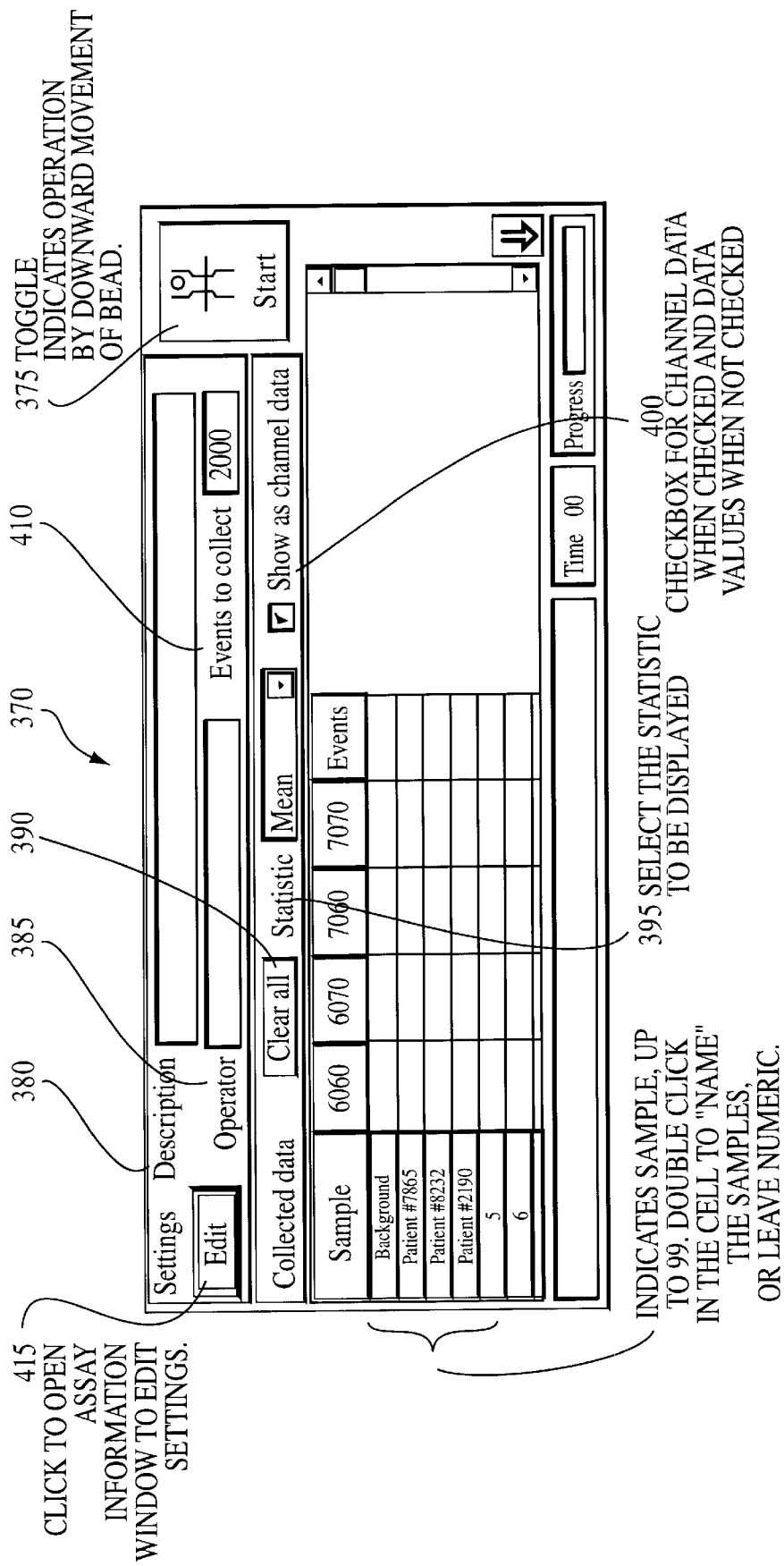
FIG. 26 is an illustrative embodiment of a results table.

The graphics display for the Data Acquisition application module and/or the Multiplexed Analysis application module includes a graphical result table 370, as shown, by way of illustration, in FIGS. 22 and 26. The results table 370 is optionally displayed upon first entering the module. The Results table 370 includes means for displaying data collected during an experiment as the cytometer acquires it.

The Results table 370 includes one or more of the following features. A "Start" option or virtual button 375 provides means for toggling acquisition of data via the flow analyzer 25. Optionally, the "Start" button, for example, includes a graphical indication of operation, such as by downward movement of a bead through an examination zone. That is, for example, although a flow cytometer 25 is set to "Run", optionally, no data is acquired until the "Start" button 375 is clicked or selected. Advantageously, such a feature permits a user to leave the flow cytometer 25 on "Run" between biological samples and to resume data acquisition upon selected the "Start" button 375. Optionally, with the sample table on the flow cytometer 25 on "Run", the sample continues to pass through the flow cytometer 25. In such a manner, data optionally is not collected, although the flow cytometer 25 continues to use sheath fluid and/or produce waste.

The Results table 370 optionally includes a row or column indicating a name or number of one or more samples and/or a background or baseline. The Results table 370 also optionally includes one or more columns or rows each labeled for a respective bead region, or analyte of interest. Each such column or row would track the number of events processed, and identified as one of the respective bead regions. The Results table 370 also optionally includes an "Events" column or row, tracking the total number of events processed for a sample or a background test.

A "Description" user entry option or virtual button 380 includes means for recording and/or displaying a description of the experiment. The "Description" option 380 optionally includes, for example, input taken from the template selected.

An "Operator" user-entry option or virtual button 385 includes means for recording and/or displaying an individual or team conducting the experiment. The "Operator" option 385 includes, for example, relevant information taken from the selected template.

A "Clear All" user-entry option or virtual button 390 includes means for clearing a display, such as a screen, of, for example, all data and graphs, and optionally delete associated files. Optionally, the "Clear All" option 390 further includes means for prompting a user with a warning message prior to execution such as, "Continuing will clear the table, graphs, and collected data files. Do you want to continue?"

A "Statistic" user-entry option or virtual button 395 includes means for offering one or more of the following statistics to be displayed for each parameter in the table: mean, coefficient of variation (Standard Deviation/Mean× 100), Count for Gated events, for example, if gates are set), Peak value, Standard Deviation from the Mean. The offering means include, for example, a pull-down menu.

A "Show as channel data" user-entry option 400, such as a check box, or virtual button, includes means for allowing a user to select which type of data will be displayed in the table. This option, for example, does not affect storage of data, but rather affects the display of data. Optional types of data, for example, include channel data, such as, data displayed in channel numbers regardless of whether the signals were collected from the flow analyzer in, for example, linear or log mode. Alternatively, optional types of data, for example, include data values, such as, data collected in log value if signals were collected using log amplification or in linear value if signals were collected using linear amplification.

An "Events to collect" user-entry option or virtual button 410 includes means for indicating the number of events to be collected for each sample as set in, for example, an Assay information display or window. For example, this option optionally includes a column or row indicating a corresponding parameter such as, Forward Scatter (FSC), Side Scatter (SSC), Fluorescence channel 1 (FL1), Fluorescence channel 2 (FL2), and/or Fluorescence channel 3 (FL3). The option 410, in addition or alternatively, optionally includes a total number of gated events captured for a given sample.

Figure 27:
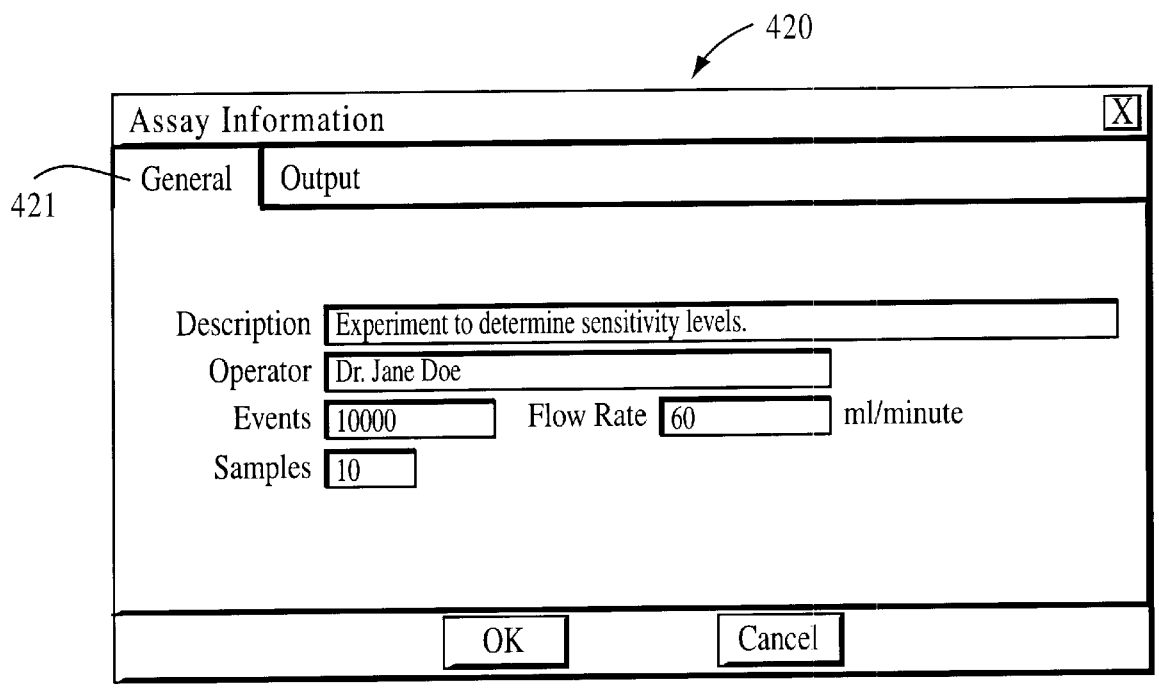
FIG. 27 is an illustrative embodiment of an assay information graphical display window.
Figure 28:
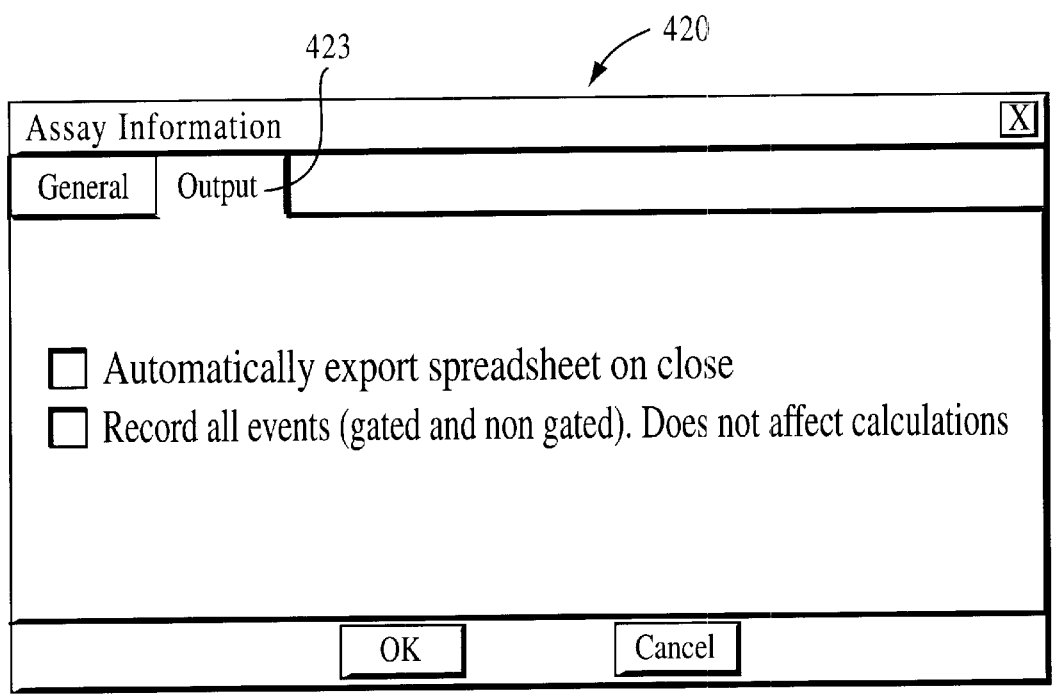
FIG. 28 is an illustrative embodiment of an assay information graphical display window.

The Results table 370 optionally includes an "Edit" user-entry option or virtual button 415 to open an Assay information graphical display window 420, as shown, by way of example, in FIGS. 27 and 28, to edit settings therein. The Assay Information window includes, for example a General tab or frame 421. For example, the General tab 421 includes an Assay on Description entry, an Operator entry, a Number of Events entry, a Number of Samples entry, and/or a Flow Rate entry. The Output tab 423, for example, includes a check box for automatically exporting data to a spreadsheet upon closing the software and/or a check box for recording all gated and non-gated events.

System Monitor

Figure 29:
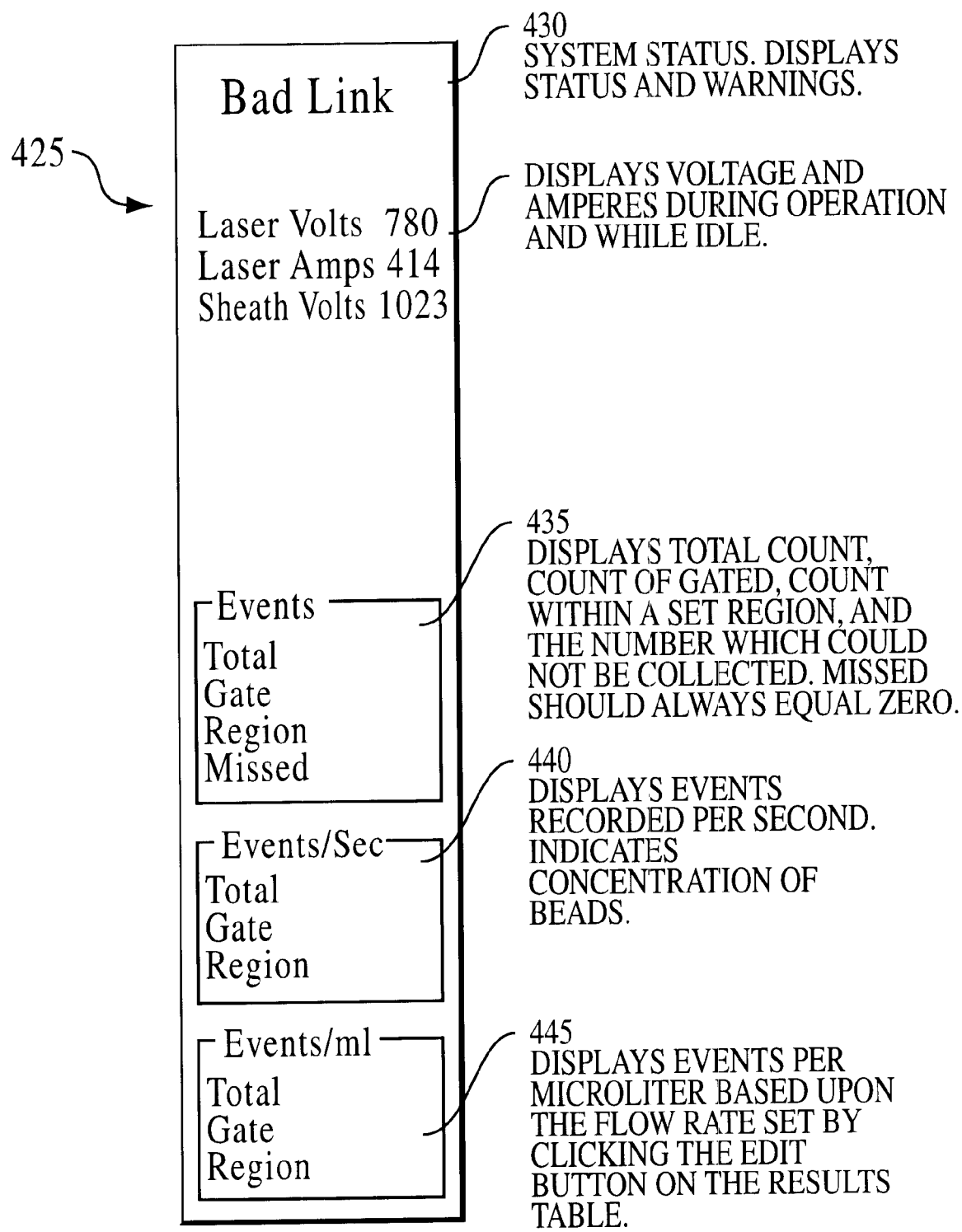
FIG. 29 is an illustrative embodiment of a graphical display of a system monitor.

The graphical display for the Data Acquisition application module and/or the Multiplexed Analysis application module optionally includes a graphical System Monitor 425, as shown, by way of example, in FIG. 29. For example, the System Monitor 425 includes a vertical information bar located on:the left or right side of the display or screen. Plainly, the System Monitor 425 alternatively includes a horizontal information bar located on the top or the bottom of the display or screen. Optionally, the System Monitor 425 is non-contiguous, whereby portions thereof are located in areas of the display or screen convenient to the user.

The System Monitor 425 include one or more of the following features. A "System Status" display 430 includes means for displaying current status of the operation and/or warnings, such as "Ready", "Standby", "Pressure", and/or "Bad Link". Optionally, the System Monitor 425 includes an "Events" display 435 for displaying a total count of events, a count of gated events, a count within a set region, and/or a number of missed events or events for which data could not be collected. Preferably, the number of missed events should always equal zero. Optionally, the System Monitor 425 optionally includes an "Events/Unit time" display, such as "Events/second" display 440 for displaying events recorded per second, thereby indicating the concentration of beads. The "Events/second" display 440 includes a total concentrating value, a concentration value for gated events, and/or a concentration value for a set region. Optionally, the System Monitor 425 includes an "Events/liquid unit" display, such as an "Events/$\mu L$" display 445, for displaying events per microliter based, for example, upon the flow rate set by selecting the edit option on the Results table 370.

Histogram Frame

Figure 30:
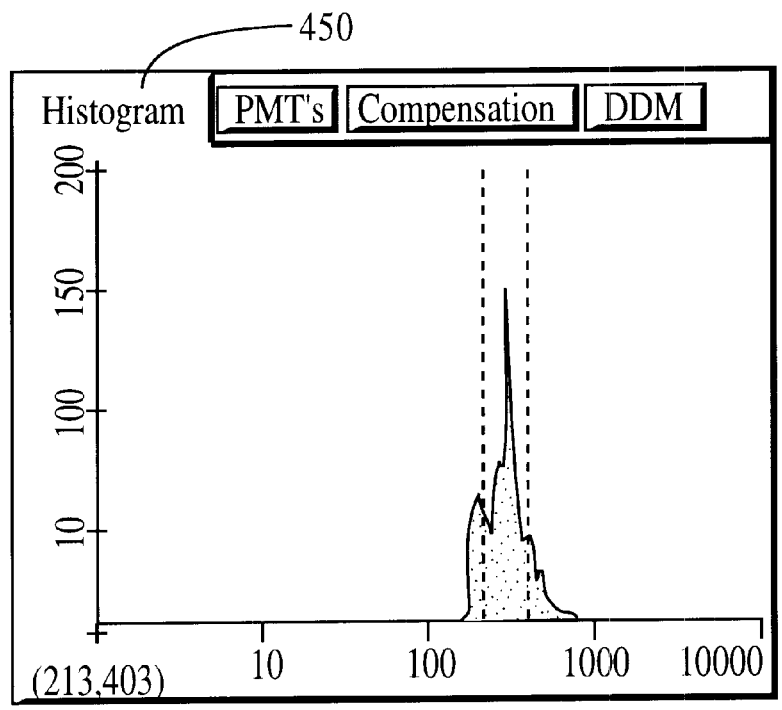
FIG. 30 is an illustrative embodiment of a graphical display of a histogram tab graphical display.

The graphical display for the Data Acquisition application module 300 and/or the Multiplexed Analysis application module 305 includes a user-selectable frame having one or more selectable feature tabs. One such feature tab includes one or more data graphs such as a histogram tab or frame 450, as shown, by way of illustration, in FIG. 30. The data graph optionally provides a graphical display of the real-time data gathered or a graphical display of data gathered and shown on a time-delayed basis. The data graph cooperates with other elements of the graphical display, such as, the "show as Channel Data" option or check box 400 in the Results Table 370.

By way of illustration, to view the assay results in linear channels a user selects or checks the "show as Channel Data" check box 400 in the Results Table 370. Such optional default data are reported in the mode in which it is collected and stored if the "show as Channel Data" check box is not checked. Optionally, at least one of the features are selected by a virtual pointer, such as by placing a mouse pointer on the histogram tab 450 and clicking on the right or left mouse button for a desired feature. The histogram tab 450, which for example, is a default data graph type, includes one or more of the following features or functions. It is, of course, understood that the below-mentioned X and Y axes are interchangeable as may be beneficial to the user.

An X-Axis function provides means for selecting, by a user, which parameter, will be displayed on the X-axis of the histogram. Optional parameters include, for example, forward scatter, side scatter, Fluorescence channel 1, Fluorescence channel 2, Fluorescence channel 3, Fluorescence channel 4, Fluorescence amplitude, and/or Fluorescence width.

A Gate function includes means for adjusting, by a user, the gate in the histogram or other data graph. Once a gate is set, data reflected in the Results Table 370 are processed through that gate and/or through the Dot Plot, as mentioned above, if set.

A Switch function includes means for switching the histogram to display the parameter in which the acquisition gate has been defined.

A Create function includes means for creating a new gate. The means include adjusting a new gate by positioning a mouse pointer, for example, on a gate border, such as a dotted vertical line, selecting the dotted line, and dragging it to a new desired position to form a border of the new gate.

A Delete function includes means for deleting or removing a current gate.

An AutoScale function includes means for setting, by a user, one or more histograms, such as for fluorescence Channel 1, Fluorescence Channel 2, and/or Fluorescence Channel 3, to the same Y-Axis scale.

A Set Scale function includes means for setting, optionally manually, by the user, the Y-Axis scale. The user sets and enters a maximum number of events, using this means.

Figure 31:
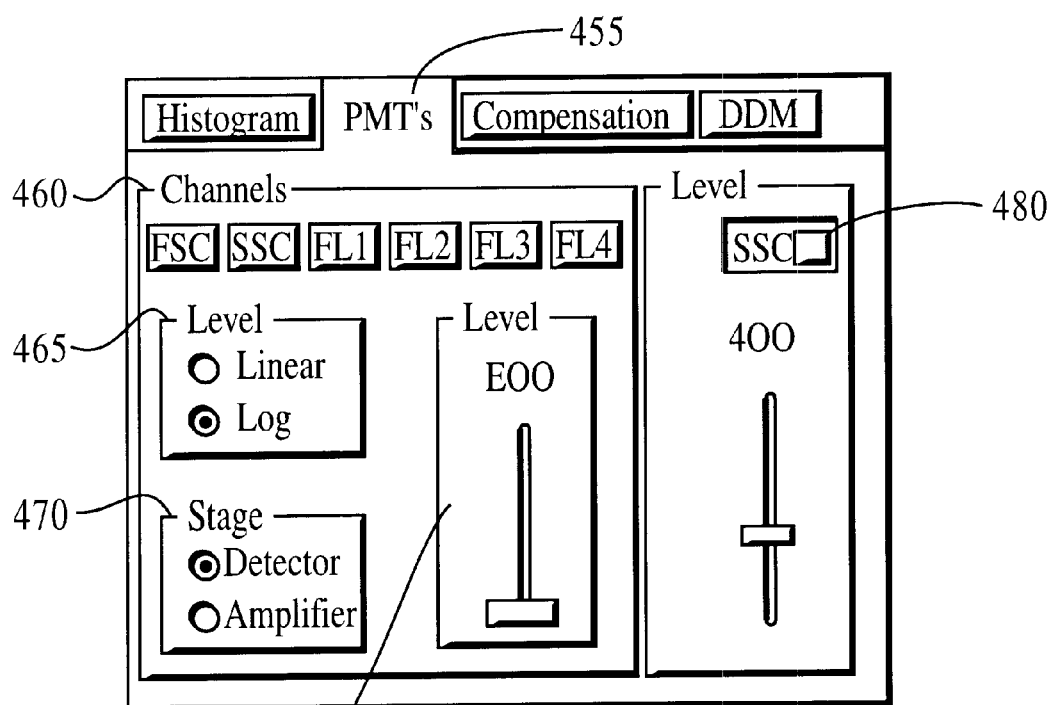
FIG. 31 is an illustrative embodiment of an optical amplifiers tab graphical display.

The frame includes a user-selectable optical amplifiers or PMT's frame or tab 455, which includes means for controlling the photomultiplier or optical amplifier settings of the flow analyzer as shown, by way of example, in FIG. 31. Optionally, changes made via this means are optionally reflected on a control panel of the flow analyzer.

The PMT tab 455 includes a Channels option 460. This option includes means for selecting a parameter, such as forward scatter, side scatter, Fluorescence Channel 1, Fluorescence Channel 2, Fluorescence Channel 3, and/or Fluorescence Channel 4. Fluorescence Channel 4 is used, for example, with an appropriately modified FACS Caliber model Becton-Dickinson flow cytometer. Once the parameter, is chosen, details thereof are optionally displayed in the frame. Optionally, all changes to the parameters are stored irrespective of whether they are displayed.

The PMT tab 455 optionally includes a Data Mode option 465 including means for selecting, by a user, either linear or log mode. The PMT tab 455 optionally also includes a Stage option 470 having means for selecting, by a user, a Detector feature for adjusting the voltage of a optical amplifier, such as a PMT, and/or Amplifier feature for adjusting the linear gain if the Linear Data Mode is selected. The PMT tab 455 optionally includes a Level option 475 having means for establishing the optical amplifier or PMT voltage or gain for the selected channel, depending, for example, on the Data Mode 465 and/or Stage 470 selected, for example, using a graphical slide.

The PMT tab 455 optionally also includes a Threshold option 480 having a channel selector and/or a threshold slider. The channel selector includes, for example, a pull-down menu allowing a user to select an appropriate parameter to be adjusted using the threshold slider. For example, a default parameter is side scatter. The threshold slider includes means for adjusting the channel number for the threshold if the selected parameter. That is, by manipulating the slider, the user establishes a minimum channel limit for detection of an event.

Figure 32:
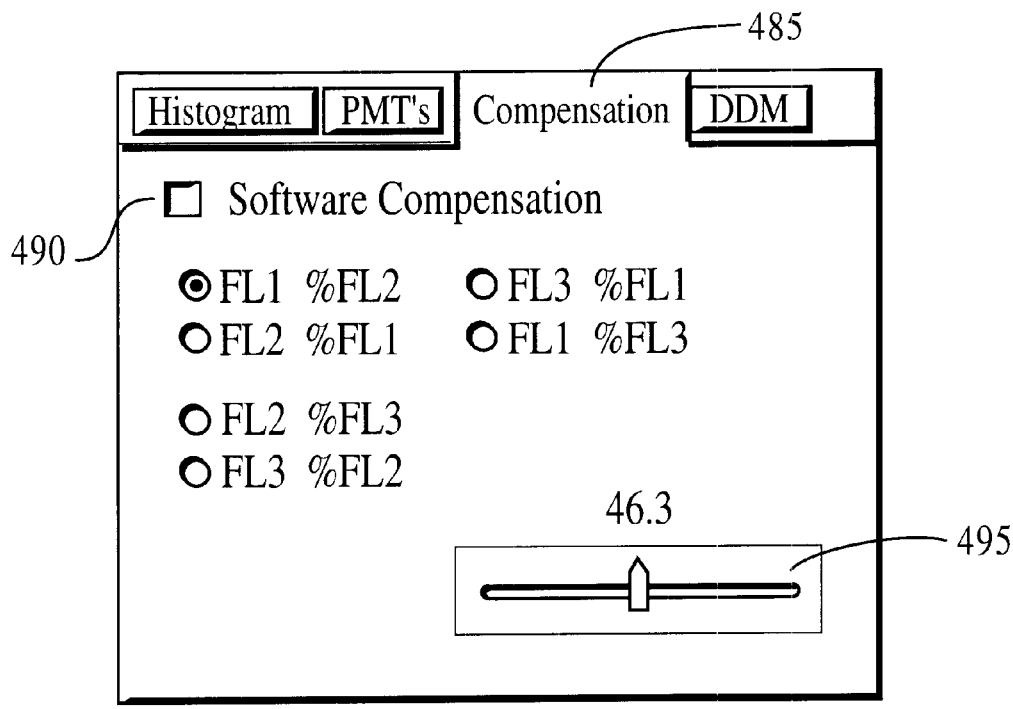
FIG. 32 is an illustrative embodiment of a color compensation tab graphical display.

The frame optionally also includes user-selectable Compensation tab 485, as shown, by way of example, in FIG. 32. The Compensation tab 485 includes means for setting, by a user, percentages (for example, from 0% to 99%) of software spectral overlap compensation override for one or more of the fluorescence channels offered using the threshold slider. The Compensation tab 485 also optionally includes a selection or check box 490, for example, for selecting the software compensation override. The feature also includes the fluorescence channels available for software compensation override. To this end, by way of illustration, if the software compensation override check box 490 is not checked or selected, the compensation levels established by the flow analyzer hardware remains in effect.

Each fluorescence channel includes a selectable option button, for example. When an option button for a channel is selected, the compensation level is optionally displayed, for example, on the tab. Optionally, all of the established compensation levels are sorted even when not displayed on the tab. The Compensation tab 485, for example, includes one or more of the following fluorescence channel ranges, which are adjustable by, for example, a graphical compensation slide 495 compensation:

% FL1-% FL2 (which decreases interference of fluorescence from Fluorescence channel 2 into Fluorescence channel 1)

% FL2-% FL1 (which decreases interference of fluorescence from Fluorescence channel 1 into Fluorescence channel 2)

% FL2-% FL3 (which decreases interference of fluorescence from Fluorescence channel 3 into fluorescence channel 2)

% FL3-% FL2 (which decreases interference of fluorescence from Fluorescence channel 2 into Fluorescence channel 3)

% FL2-% FL1 (which decreases interference of fluorescence from Fluorescence channel 1 into Fluorescence channel 2)

% FL1-% FL3 (which decreases interference of fluorescence from Fluorescence channel 3 into Fluorescence channel 1).

Figure 33:
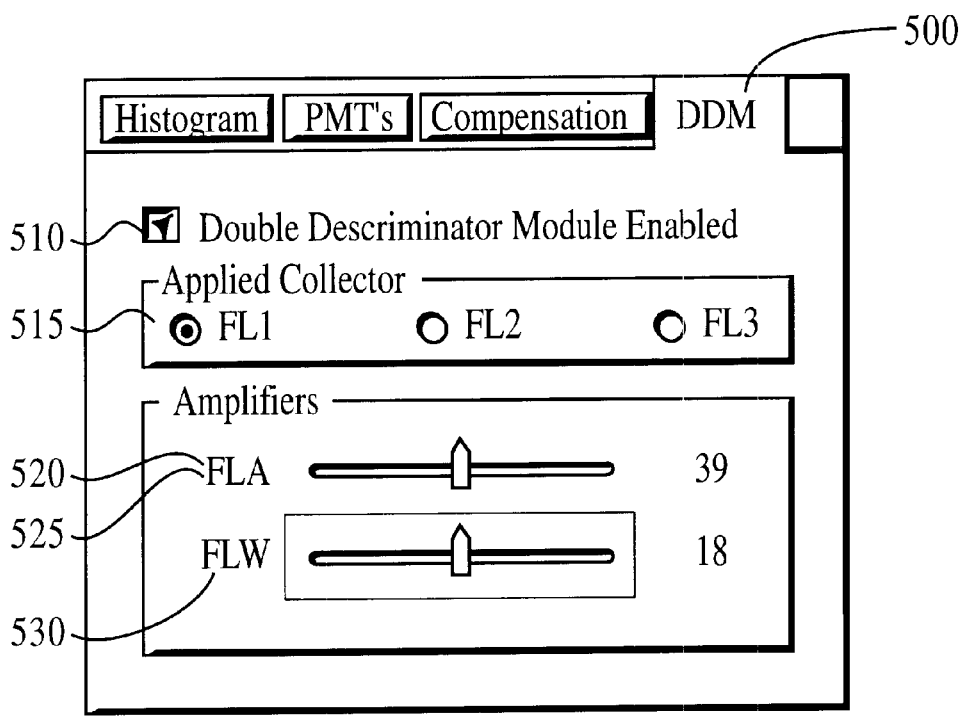
FIG. 33 is an illustrative embodiment of a doublet discriminator tab graphical display.

The graphical color compensation slide 495, for example, permits a user to set percentages for the above channel ranges, such as from 0% to 99.9%. The frame optionally includes a Doublet Discrimination Module (DDM) tab 500, as shown, by way of example, in FIG. 33, having means for distinguishing between singlets (single beads) and doublets (two or more beads non-purposely affixed to each other). The DDM tab 500 includes, for example, a selectable checkbox 510 for enabling the feature. Optionally, the DDM checkbox 510 is optionally always checked, or is checked as a default feature, if the associated flow analyzer 25 is capable of detecting doublets. The DDM tab 500 optionally includes an Applied Collector feature 515 having means for selecting, by a user, a appropriate parameter for pulse processing. By way of illustration, a user selects one or more channels, such as Fluorescence channel 1, Fluorescence channel 2, and/or Fluorescence channel 3, to obtain more specific data. The DDM tab 500 optionally includes an amplifier feature 525 having means for setting, by the user, a gain via a virtual slider, for example. By way of illustration, an FL-A slider optionally enables a user to set the signal area for the channel selected in the Applied Collector feature. Similarly, by way of example, an FL-W slider 530 optionally enables a user to set the signal width for the channel selected in the Applied Collector feature 515.

Dot Plot Frame

Figure 34:
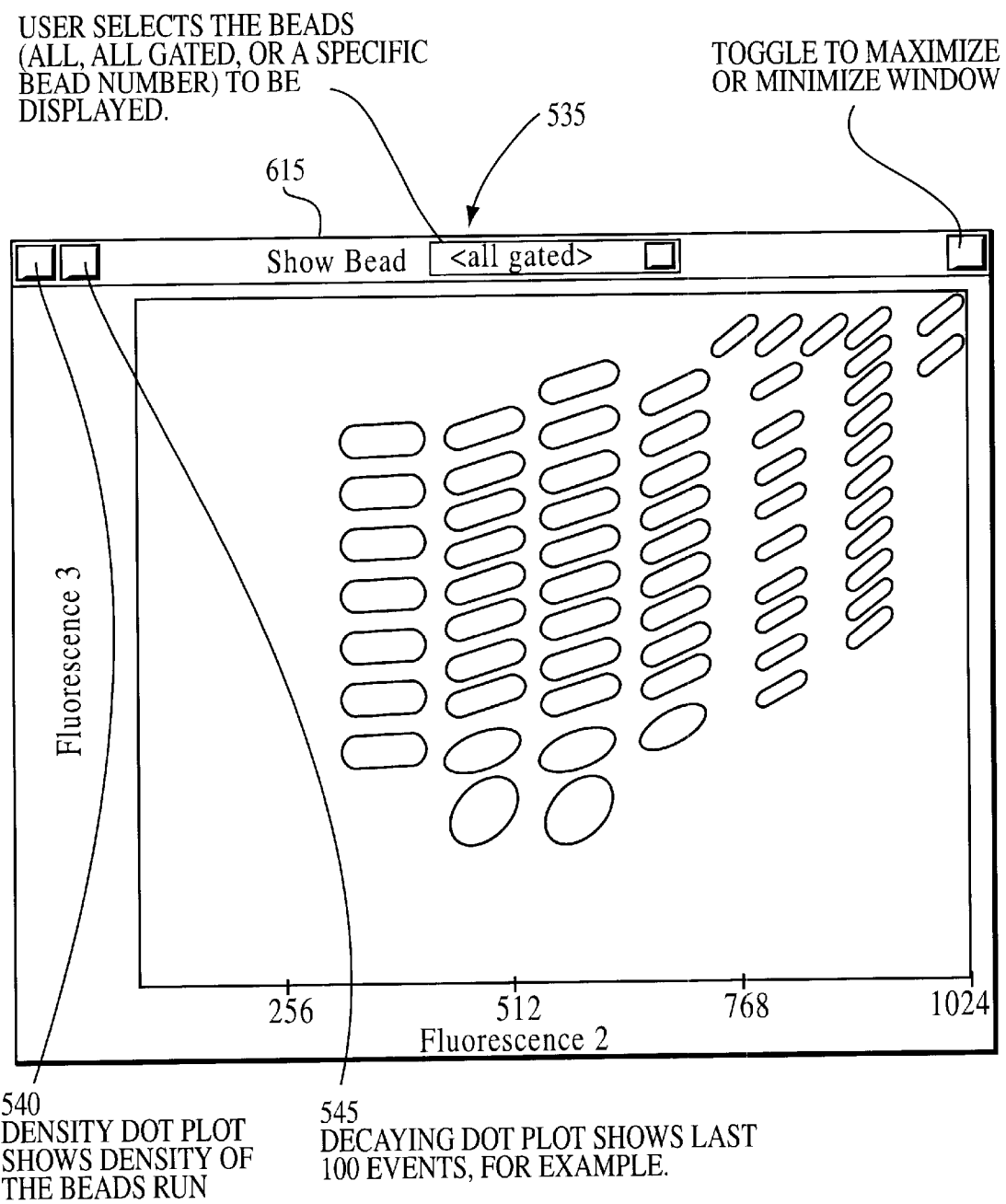
FIG. 34 is an illustrative embodiment of a dot plot graphical display.

The graphical display for the Data Acquisition application module 300 and/or the Multiplexed Analysis application module 305 optionally includes another frame for displaying a real-time, two-parameter graphical display such as a Dot Plot graphic display 535 of the collected data, as shown, by way of illustration, in FIG. 34. It is understood that this display is optionally time-delayed and/or includes more than two parameters. The Dot Plot graphic display, for example, depicts the data as accumulations of tiny dots, each dot representing a data point based on the two parameters, for example.

The Dot Plot graphic display 535 includes one, two, or more choices for the display of the data. For example, an optional choice includes a Density Dot Plot 540 having means for displaying constant accumulation of events with increasing or decreasing density depicted by, for example, contrasting or differing colors, shading, and/or hatching. The Dot Plot graphic display 535, alternatively or in addition, includes a Decaying Dot Plot 545 having means for displaying a number, for example, 1, 10, or 100 or more, of the most recent events acquired by the flow cytometer. Optionally, the Decaying Dot Plot 545 is updated continuously, i.e., in real-time, as data are collected, or updated on a time-delayed basis.

Additional optional features of the Dot Plot Frame 535 include one or more of the following. They, for example, are selected by a virtual pointer, such as via clicking on the right or left mouse button in the Dot Plot frame. For instance, optional X-Axis and/or Y-Axis choices include, for example, respective pull-down menus to set one or more of the following parameters forward scatter, side scatter, Fluorescence channel 1, Fluorescence channel 2, Fluorescence channel 3, Fluorescence Area, and/or Fluorescence Width. Alternatively, or in addition, the user may define or re-define these parameters by selecting, for example, by left or right clicking of a mouse, on the X-Axis or the Y-Axis.

A Region choice is an optional Dot Plot Frame feature. Optionally, it is available only in the Data Acquisition application module. The Region choice includes means for establishing, by a user, regions for viewing data specific to the user's needs. In turn, the Region choice includes one or more of the following options. A Show option includes means for shifting, when selected, the display to those parameters in which the specified region exists. A Create option includes means for creating, by a user, a new region by, for example, one or more of the following steps. A mouse pointer, for example, is moved to an area in the Dot Plot where the new region is to be created. A left or right mouse button is depressed while dragging the associated cursor over the appropriate area encompassing the desired region. Optionally, the encompassed region optionally changes color, for example, from gray to white, indicating the location and area of the new region. To modify an established region, for example, a keyboard key, such as, the shift key, and the left or right mouse button is optionally held down while the mouse is dragged to alter the region.

Figure 35:
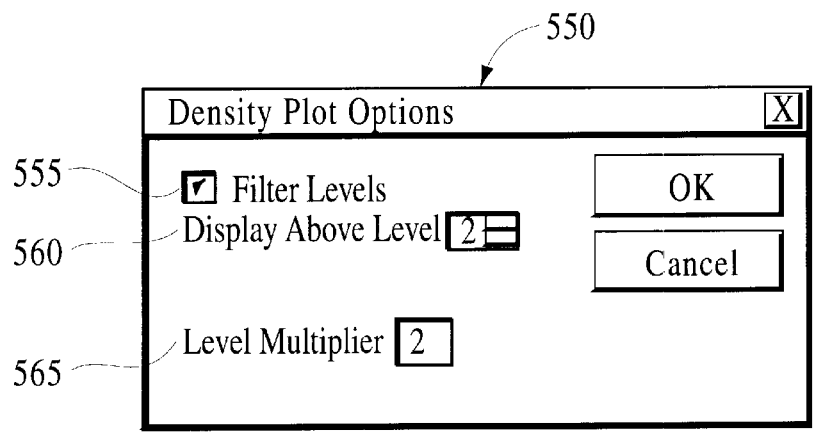
FIG. 35 is an illustrative embodiment of a density plot graphical display window.

A Density Plot Options feature 550, as shown, by way of example, in FIG. 35. The options feature 550 includes means for adjusting the scale and/or other features of the Density Dot Plot, and/or means for eliminating data values determined to be insignificant to the display. For example, the Options choice includes an entry selection or checkbox 555 for Filter Levels, which includes means for filtering put events that fall below a desired level. For instance, if the Filter Levels checkbox 555 is not checked, a "Display above level" option 560, for example, is optionally not available, and a Level Multiplier option 565, for example, has no effect. The "Display above level" option 560, in operation, includes means for setting, by the user, the level at which events will be displayed in the dot plot 535. Events below this level are optionally ignored. This level is a number, which, for example, include an exponent of the Level Multiplier 565, and is optionally set, for example, between 1 and 8, although levels greater than 8 are also possible. The Level Multiplier 565 includes means for establishing, by the user, the necessary base number of events that must fall within a region before being displayed.

By way of illustration, if the Filter Level checkbox is checked, the "Display above level" option 560 is set at 3, and the Level Multiplier 565 is set at 2, events optionally are not displayed until 8 or more events have been registered. According to this illustration, a first color level in the dot plot display 535 is at 8 events, a second color level is at 16 events, a third color level is at 32 events, etc.

OPTIONAL ADDITIONAL FEATURES OF THE MULTIPLEXED ANALYSIS MODULE

The Multiplexed Analysis Module 305 optionally adds to the functionality available in the Data Acquisition module. Optional features of the Multiplexed Analysis Module 305 are described as follows.

Figure 36:
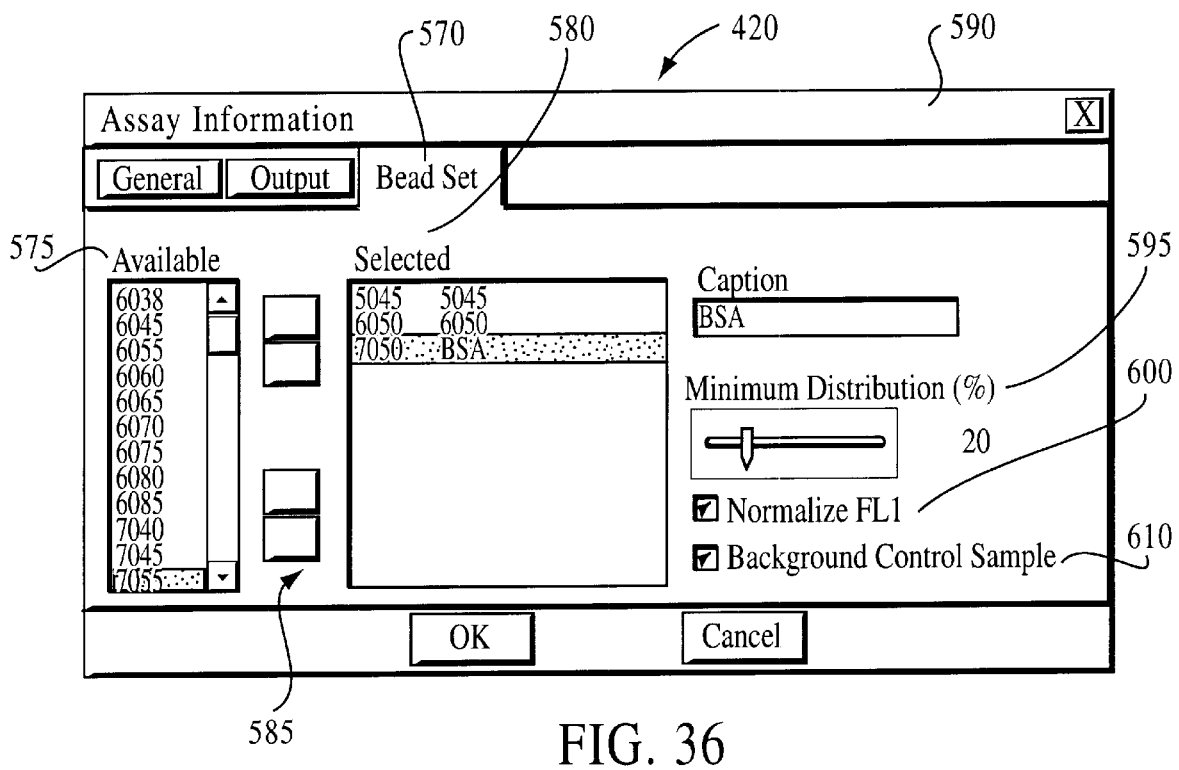
FIG. 36 is an illustrative embodiment of an assay information graphical display window.

The Multiplexed Analysis module 305 includes, for example, an Assay Information graphical display window 420 having one or more feature tabs, as shown, by way of illustration, in FIG. 36. For example, in addition to or alternative to the General tab and the Output tab described above, an optional Bead Set tab 570 includes one or more of the following options.

The Bead Set tab 570 optionally includes an "Available" option 575 having means for listing one or more, up to all, available bead sets. The Bead Set tab 570 optionally includes a "Selected" option 580 having means for storing for ease of visual recall, by the user, those bead sets selected for use in an experiment. Optional virtual arrow buttons 585 located on the Bead Set tab 570 between the. Available option area and the Selected option area provides means for adding or removing, by a user, singularly or as a group, the bead sets to be used. For example, the arrow buttons 585 optionally includes a single right arrow button and a single left arrow button for add on selected bead set and remove one selected bead set, respectively. In addition to or alternatively, for example, a double right arrow button and a double left arrow button are optionally implemented to add all bead sets to the "Selected" option area and to remove all bead sets from the Selected Option area, respectively.

The Bead Set tab 570 optionally includes a Caption option 590 having means for labeling or renaming beads, by a user, to correspond to a specific assay or function, for example, for ease of user recognition. Optionally, in the selected option area or window, an original numeric or alphanumeric designation of the bead is optionally included with a label or name provided by the user, for example, using the Caption option 590.

The Bead Set Tab 570 includes a Minimum Distribution (%) option 595. This option includes means, such as a virtual slider, for selecting, by a user, a minimum distribution level between, for example, 1 and 99% that allows the instant system to disregard, for example, any bead set that does not collect enough events to be statistically significant. For example, if the instant system is set up to collect 1600 events per sample and 16 bead sets are included in each sample, then a mean of 100 events per bead set is expected. The user optionally decides the minimum number of events per set which is statistically acceptable. That is, for instance, if all but one bead set register between 85 and 120 events and one bead set registers 7 events, it is likely that a problem exists with that one bead set. However, by setting the Minimum Distribution (%) option 595 to, for example, 25%, each set must register 25 events (25% of 100 beads per set) or it will be discarded from the data collection. As such, data optionally is not collected and/or displayed for a bead set that falls below the desired minimum distribution level.

The Bead Set tab 570 optionally includes a "Normalize Fluorescence Channel 1 (FL1)" option 600. This option includes a user-selection entry area or checkbox and means for prompting the system to eliminate spurious data points that could throw off the data as a set, when this checkbox is selected or clicked, for example.

The Bead Set tab 50 optionally includes a "Background Control Sample" option 610. I have discovered that the dyes contained within standard microspheres or beads bleed to some degree into the Fluorescence Channel 1, the channel arbitrarily chosen to reflect the detected fluorescence of the analytes of interest. This spectral overlap, or bleeding, optionally, is advantageously corrected in the Histogram frame on the Compensation tab by using, for example, a FL1-% FL2 setting of approximately 40%.

However, I determined that a more accurate method of this spectral overlap correction includes recording the mean sample spillover of each bead type in the absence of any analyte and reporter. This mean spillover is optionally subtracted from the later sample or samples mean to obtain the samples' true mean fluorescent readings.

The "Background Control Sample" option 610 includes a user-selection entry area or checkbox, for example. Checking or selecting the "Background Control Sample" checkbox 610 activates this option. Optionally, as a default measure, if this checkbox is not selected or Checked, compensation is optionally still adjustable via the Compensation tab 485.

When this option is so activated, the first sample in the Results Table 370, for example, reads "Background" and, for example, is optionally not able to be renamed once set. After running the sample, the user optionally saves the results as a template for future experiments, thereby allowing reuse of these spectral spillover values in future folders without running a background sample first. To ensure the greatest possible accuracy, optionally, the background sample advantageously is run with each experiment, and advantageously after calibration or changes to the optical amplifier or PMT's settings.

The Multiplexed Analysis application module 305 optionally includes, for example, a Permanent Bead Grid in Dot Plot Display 535. As mentioned above, each bead set, used in accordance with the instant invention, advantageously has a unique, spectral region in the Fluorescence Channel 2, Fluorescence Channel 3 (FL2×FL3) dot plot that advantageously corresponds to the bead sets's user-selected or manufacturer-selected unique numeric or alphanumeric designation. The region, for example, is pre-defined. If the bead sets selected for use do not fall in their respective regions, the user is advantageously alerted to the need to recalibrate the flow analyzer. The Dot Plot Display 535 includes means of showing the results of a sample run, displaying all gated events, for example, all events passing through the side scatter gate.

The Dot Plot Display 535 optionally includes a Show Bead option 615. This option, for example, includes a pull-down menu and means for viewing all bead sets (gated and ungated), all gated events only, and/or a specific bead set by selecting, by the user, from an all events option, an all gated events option, and/or a bead number option from the pull-down menu. By way of example, the all events option includes means for showing all beads, gated and ungated, and includes events outside designated bead set region. The all gated events option includes means for showing events registering in, for example, the side scatter gate and includes events outside the designated bead set regions. The bead number option includes means for showing up to all data associated with the bead type selected. Thus, data is optionally discriminated by, for example, the side scatter gate and the bead type region.

Optionally, the Dot Plot Display 535 includes means for viewing specific bead data by clicking or selecting, by a user, in the desired bead type region on the Dot Plot Display 535. The Dot Plot Display 535 optionally further include means for displaying Bead Details for that bead type in, for example, a box or tabular format. For instance, the box optionally displays the original bead type alphanumeric code, the user-selected bead type name, and/or the count, i.e., the number of events collected in that bead type region.

Assay Development Overview

Assays, in accordance with the instant invention, are set up in any standard configuration for standard binding assays. For example, direct binding of a fluorescent molecule, capture/sandwich assays with a fluorescent "secondary" antibody, competitive inhibition assays with a fluorescent ligand, and/or DNA hybridization assays and enzymatic assays are performed. By way of illustration, set up of an acceptable assay include the following. A target molecule is coupled to each bead in a bead set. A reporter molecule is labeled with, for example, a green fluorescent reporter group. The assay is optionally optimized, for example, for concentrations of target and reporter molecules, numbers of beads, and/or assay conditions.

As to target coupling, sample procedures for coupling, for example, proteins, or oligonucleotides to beads of a given subset are as follows. These procedures are intended only as non-limiting, exemplary guidelines for initial assay setup. By way of illustration, the guidelines include coupling of near-maximal amounts of target molecules to the beads. Alternatively, the guidelines include coupling of minimum detectable quantities of target molecules to the beads.

SAMPLE METHOD OF OPERATION

In view of the above-described apparatus, a method of operation therefor, given by way of illustration only, is provided herewith. As indicated above the beads are identified into their respective, separate subsets. Each has a bead identifier (ID) associated with it. For each bead ID, for example, fluorescence channel 1, FL1 statistics are collected. It is the FL1 statistics that the researcher or the clinic is generally interested in, because it is an indicator of how much biological activity is seen on the bead. The beads include a set amount of Fluorescence channel 2, (FL2) and Fluorescence channel 3 (FL3). But, it is in an individual sample, e.g., the human serum, wherein reactant-analyte interaction defines how much of the FL1 signal or fluorescence is found or detected.

For example, a hundred events of each bead type are collected. However, the assay is what is to be read. For those one hundred events, all of the FL1 signals are summed, and an average or peak reading or standard deviation, coefficient of variation, and a variety of statistics are taken therefrom. Once the statistics have been collected, the software application generates a data table, the rows representing the different samples that have been run.

While the software and hardware are running, the events come in and are optionally displayed in real time on, for example, OCX graphic controls, such as described above and illustrated in the figures. In general, an OCX is an Object Linking and Embedding (OLE) custom control, a special-purpose program that can be created for use by applications running on Microsoft's Windows systems. Advantageously, use of OLE supports the development of "plug-and-play" programs that can be written in any language and used dynamically by any application in the system. These programs are known as components, and the application in which they are run is known as a container. In the instant invention, the OCX, for example, are responsible for displaying, for example, histograms for any one of the channels. Thus, the control and analysis software 50 has, for example, two controls which are OLE controls. The control and analysis software 50 instructs a graphics component called "LumGraph component," or LumGraph.OCX 700, to behave, for example, as a histogram or to behave, for example, as an X-Y plot.

Figure 43:
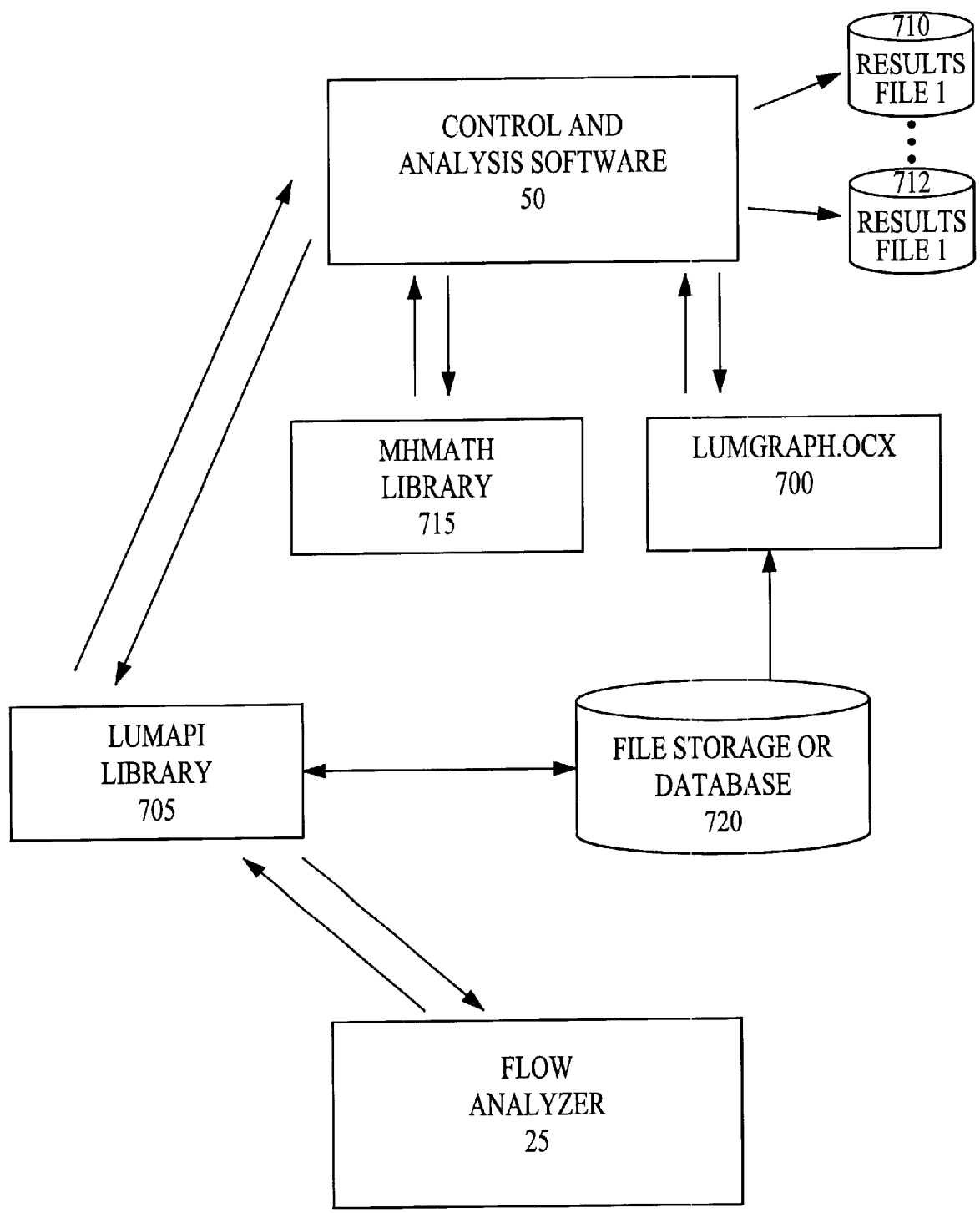
FIG. 43 is a schematic of an embodiment of the computer-implemented process cooperating with the flow analyzer.
Figure 44:
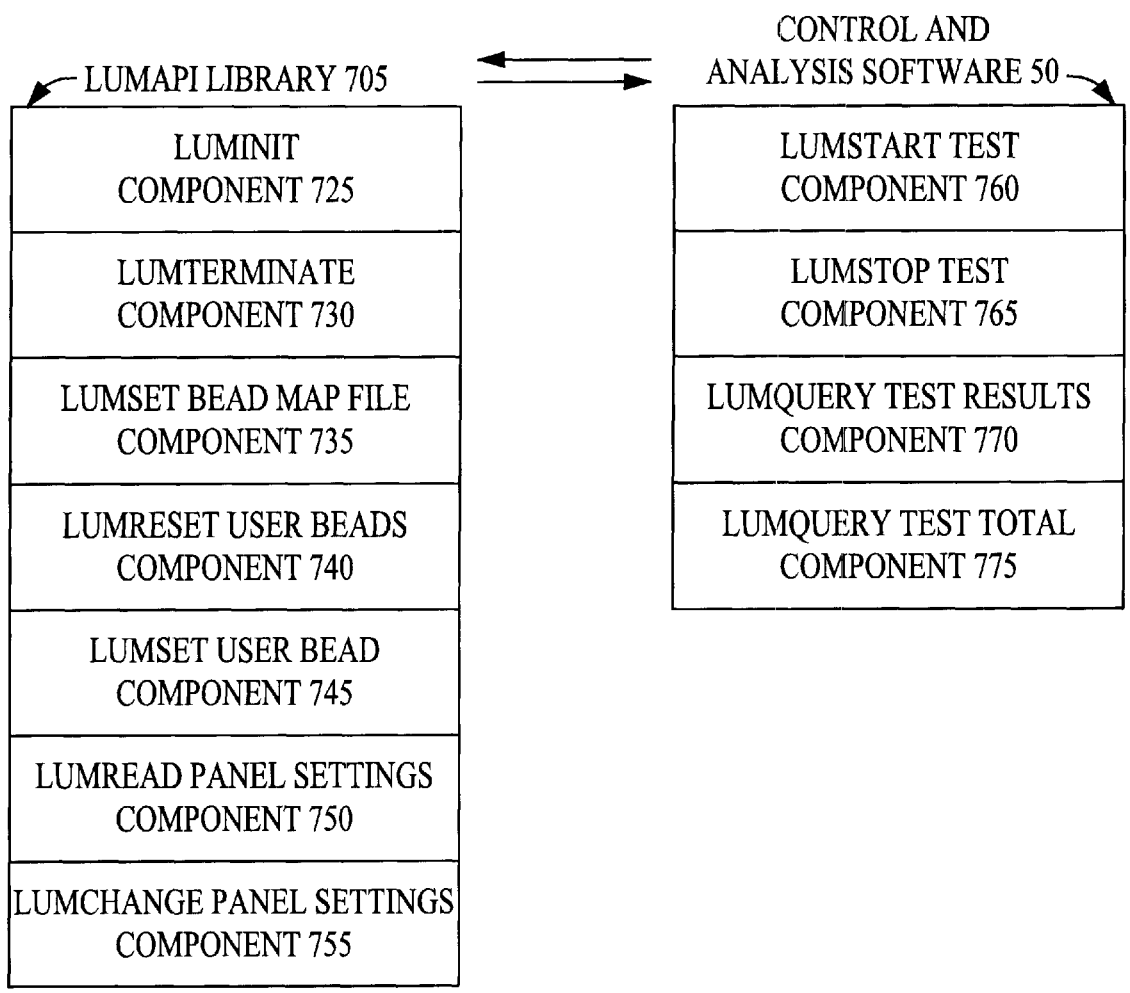
FIG. 44 is a block diagram of exemplary components of an application programming interface library and of a control and analysis software consistent with the instant invention.

A LumAPI application program interface component 705, when it gets the machine information in real time from the flow analyzer, for example, spews things out to a file, as shown schematically in FIGS. 43 and 44. An API, or application program interface, is the specific method prescribed by a computer operating system or by another application program by which a programmer writing an application program can make requests of the operating system or another application. Advantageously, the LumAPI component 705 includes a dynamic link library (DLL). A DLL is a collection of small programs, any of which can be called when needed by a larger program that is running in the computer.

The small program lets the larger program communicate with a specific device such as a daughter board, which is often packaged with a DLL program (usually referred to as a DLL file). Advantageously, the LumAPI component 705, optionally implemented as a DLL file, need not be in random access memory (RAM) together with the main program, thereby saving RAM space in the computer.

As shown in FIG. 43, the control and analysis software 50 links the LumGraph component 700 and the LumAPI component together 705, for example, by telling the LumGraph component 700 what the real-time output is going to be. The LumGraph component 700, for example, then accesses this real time output. Then, the LumGraph component 700 outputs the data into these displays which are available via control and analysis software 50. The control and analysis software 50 initializes the LumAPI component 705, and tells it what machine to talk to and for which bead types to look. It has, for example, sixty-four possible bead types. Other numbers of bead types are, of course, acceptable.

The LumAPI component 705, for example, stores in a database 720 an output of events, and raw data representing upper channels, side scatter, FL1, FL2, and/or FL3. The LumGraph component 700, for example, accesses the same data in a graphical way for presenting into the control and analysis software 50, which then displays the data.

Statistics are, for example, generated in the LumAPI component. The control and analysis software 50 retrieves the statistics from the LumAPI component 705, and re-polls it, periodically or aperiodically, to obtain the latest statistics. Thus, the statistics go back to the control and analysis software 50, which displays them appropriately, for example, in a table in real time. The software 50, performs statistical analysis, for example. It then optionally records any results of the statistics to one, two, or more external file types 710 and 712, for example, in a spreadsheet format.

As to the apparatus components, it is to be understood that the test probe, or needle, for example, enters the sample tube to draw the sample out of the tube and into the machine. For example, the syringe pump actually goes down and draws that sample in through a valve. The valve optionally includes a three way valve in the syringe pump, so that after the sample is drawn into a standard sample loop. Then, the valve is switched over to inject the sample through another tube into the optical assembly. Advantageously, the inclusion of the sample loop prevents sample fluid from contaminating the syringe pump. The sample, for example, goes into the optical assembly through a needle, the droplets-forming at the tip of that needle.

As mentioned above, the droplets comprise the beads and solution. There are, for example, a billion beads, or more or less, in a tube. The beads are, for example, so small that one cannot see them with the naked eye. Indeed, the mixture of the beads and the solution, for example, looks like clear water. The droplets are formed, for example, at the tip of that needle inside the cuvette on the optical assembly.

As mentioned above, the system includes a sheath fluid container holding the sheath fluid supply, such as a water-supply. A compressor pump provides air pressure over the top of the water, forcing the water into the system at, for example, approximately 5.5 psi. A pinch valve shuts off that water supply, when samples are not running so as to conserve water. The air pressure drives this water into, for example, the very same optical assembly after it passes the pinch valve. There, it fills the cuvette up to the neck down region of the cuvette, which resembles an inverted half of an hour glass.

Sheath fluid, e.g., water, fills up the large portion of the cuvette and as the water gets forced into the neck down region, the water accelerates very rapidly. So, instead of moving at about, for example, a tenth of meter, per second, the sheath fluid moves at, for example, about five meters per second in that neck down region just because of the volume restriction. The water accelerating causes the sample drop that forms on the end of the needle to be elongated. The hydro-dynamic principles behind this are well known. By the time the fluid arrives at the area of the optical assembly where the lasers are, the sample has been stretched into a very tiny strand that is, for example, about twelve microns in diameter. Of course, other sized strands, larger or smaller are also effectively used.

At the viewing area, there is a two hundred micron chamber or capillary, having, for example, a 200 micron cross-section. The outer 188 microns of the cross-section contains water, and the very center or substantially center of the cross-section, for example, the inner most 12 microns, contains the sample. The optical sources, such as lasers, are aligned, or pointing, to a precise point along the capillary from for example, substantially opposites sides, concentrating a beam, for example, about 30×60 microns wide and long under the same spot. As the beads and the sample fluid pass through the laser beam, the beads, which have fluorescent dye inside, are illuminated and then they start fluorescing, which means that they emit a longer wavelength at which they were excited.

Optical detectors surround the viewing area or chamber, and also point to that very same spot where the lasers pointed. The optical detectors substantially focus on the same spot and image the bead as it is passing through the light beam. That is, the fluorescence values, corresponding to, for example, fluorescence channels, 1, 2, and 3, detected are transmitted to a fiber optic cable connected to each or all of the optical detectors. The cable optionally includes a multi-mode fiber, wherein the light travels down the fiber and through an optical filter. The optical filter, for example, only allows certain wavelengths of interest to pass through into the electronics, for instance, four filters, four channels, and four detectors.

After the light in the band of interest passes through the filters, it enters an optical amplifier, such as a standard avalanche photodiode. An avalanche photodiode is a circuit that converts light or photons into electrons. The more light that goes into an avalanche photodiode, the more current is admitted by the avalanche diode. That current is then converted to a voltage by a transmit beads amplifier with a gain of, for example, about a million times, i.e., re-amplified a million times, for example. The current is then inputted to an op-amp filter that band limits the signal to eliminate substantially all high frequency noise to, for example, about 450 kHz. The output of the op-amp optionally is then amplified one more time before it goes into, for example, one of four A to D converters. Alternatively, a greater number of A to D converters are also possible and is limited only by the processing power of the associated central processing unit. For example, five or eight A to D converters are optionally included. On the back side of each A to D converter, is, for example, a DSP, such as a 2181 digital signal processor which reads each of the four A to D converters, thereby performing, for example, four million read operations every second, i.e., one million read operations for each of the A to D converters. Plainly, if, for example, five A to D converters would entail five million read operations every second. It stores it in one or more circular buffers inside the DSP's memory.

Another thread of the DSP's operation constantly searches the sample data for the presence of an event. An event includes signal levels above the background level, and appears as one or more pulses created by the avalanche photodiode in increasing numbers via the A to D converters to the DSP. When the number gets above the certain threshold, optionally set by the user, an event is triggered and that pulse is analyzed by the DSP software. Optionally, and advantageously, if it is a single bead event as opposed to two beads passing through the beam at the same time, the DSP accepts that as a valid event, based again by analysis of its waveform. The values for all the fluorescence channels, the peak values for each fluorescence channel, are then passed on in record form to, for example, a micro controller.

The micro controller, which is advantageously linked to the DSP through direct memory access, takes these packets out of the DSP memory, formats them, and passes them onto the control and analysis software. The micro controller is also responsible for a number of other functions. It optionally controls the syringe pump, for example, telling it how much to draw, how fast to draw, and/or whether to expel waste. It optionally controls performance of a wash cycle on the syringe pump to prevent sample carryover, for instance. The micro controller optionally controls the pinch valve which starts and stops the sheath flow into the instrument. It optionally controls the high voltage bias of the avalanche photodiodes. The avalanche photodiodes optionally require very high voltage to operate, and so the micro controller optionally sets the precise voltage for each fluorescence channel based on the properties of each particular avalanche photodiode.

An avalanche photodiode optionally needs as little as. 10 volts in order to operate at minimum efficiency or as much as 200 volts to operate at maximum efficiency. The micro controller, optionally regulates this operating voltage also. It optionally also senses a switch when the aspirator arm is down to know to begin drawing sample. The micro controller optionally also monitors the air pressure to ensure sufficient air pressure on the sheath fluid to provide a valid sample of, for example, 12 micron core size. Obviously, the lower the pressure on the sheath fluid, the larger the core size, whereas the higher the pressure, the smaller the core size.

Advantageously, at sheath fluid pressure of 6 psi to 7.5 psi, for example, approximately 6.5 psi, and an injection rate of the sample at approximately 1 microliter per second, the desirable 12 micron sample core is obtained. It also monitors the high voltage and reads it back to make sure that everything is operating properly and does numerous diagnostics. The top of the system optionally includes an air cylinder that optionally shares the same air pressure pump that drives the sheath fluid through the system. The extra pressure is used to move the air cylinder up and down. The air cylinder is optionally attached to the test probe. Consequently, by forcing air either into the top or the bottom of the air cylinder, the sample needle is moved up and down. Such a configuration advantageously reduces the operator's responsibility largely to pressing the start button to "on" in the instant diagnostic system.

There are several advantages of this overall system. The light source setup, such as the laser setup, is very stable since all components are mounted to the same base, permitting a smaller or tighter spot beam for the lasers. That is, because the setup is so stable, a fairly accurate spot on the fluid flow stream is obtained for reading the beads. Another feature of the present invention is that as a result of the stability, low power lasers are used, such as those having 10 milliwatt power requirements. However, lasers having power requirements less than or equal to 3 milliwatts up to 30 milliwatts are alternatively used.

Another feature of the present invention is that a compressor with fairly low psi rating is used relative to other cytometers that require very expensive compressors with fairly high psi ratings. Fast cytometers that can run upwards of 20,000 beads per second usually require a lot of pressure, such as 30 psi and up. So, the compressor being used in the instant invention is much less expensive, more compact, and longer lasting than prior flow cytometers.

Another important feature of the invention is that the optical assembly is made of many different pieces, but are optionally bolted together onto one solid piece that holds the cuvette, the viewing chamber, the lasers and the detectors, all securely mounted together. Advantageously, the assembly comprises stainless steel, although other sturdy materials may also be used. In addition, the laser/detector assembly is compact, durable, and is easily shipped with little or no functional damage.

SAMPLE PROGRAM COMPONENT

A LumAPI Library 705 includes, for example, a standard application programming interface library, which communicates with the flow cytometer via the serial or parallel connection. The LumAPI Library 705 optionally includes standard communication functions, such as shown, byway of example, in FIG. 44.

A standard MHMath Library 715, such as shown in FIG. 43, includes routines for calculating a polynomial trend-line, using an arbitrary number of data points, for example, one, two, three, or more, for input, and for calculating a polynomial of any order. The algorithms therein are, for example, derived from *C/C++ Mathematical Algorithms for Scientists and Engineers*, Namir C. Shammas, ©1995, McGraw-Hill, incorporated herein by reference.

As shown in FIG. 43, the control and analysis software 50 communicates with either or both of these libraries. It includes a main user interface program, which includes the GUI between a user and the instant invention. This program or diagnostic system application is developed using, for example, Microsoft Visual Basic or any other suitable programming language. It optionally includes visual components, such as screen displays, user input facilities, such as dialog boxes, and/or user option facilities, such as, for printing. The diagnostic system application also includes a controlling program to communicate with the LumAPI library 705, which in turn communicates to the flow analyzer via the serial or parallel connection.

The diagnostic system application includes an initialization means or component. The initialization component includes, for example, a LumInit component 725, which initializes the device interface for the flow cytometer to use flow cytometer resources. The LumInit component 725, for example, includes one or more standard callable software functions, discussed below, which are called prior to calling another LumAPI function. The initialization component, for example, returns a non-zero return value indicating an occurrence of an error during initialization. In such a case, a default return value, for example, is zero. The steps performed by the initialization component includes one or more of the following steps.

Initialization Functions
LumInit Component

A LumInit component means 725, or function, for example as shown in FIG. 44, as mentioned above, initializes the device interface for the flow cytometer. Optionally, the LumInit component 725 is one of the available LumAPI functions. Advantageously, the control and analysis software, for example, calls it prior to calling any other LumAPI function. The LumInit component 725 includes initializing a multimedia timer for background processing to poll the DSP, for example, by:

starting the background task;

calling a flow cytometer initialize function, which includes initializing relevant data structures;

calling an instrument reset function to initialize the data structures, to load the DSP binary values into memory, to reset the DSP and optionally, pause to load the DSP binary to the serial or parallel connection interface board and look for an initialization "O.K." status, to set an error status if the initialization status is not "O.K.", and to notify the DSP of the operational status of the computer communicating therewith; and/or initializing flow cytometry standard values. Once finished with using the LumAPI library 705, the control and analysis software 50 calls, for example, a LumTerminate component or function 730.

LumTerminate Component

A LumTerminate component means 730, or function, for example as shown in FIG. 44, closes a device session with a flow cytometer, thereby freeing any flow cytometer resources used created by calling the LumInit function 725. Optionally, the LumTerminate component 730 is a LumAPI function. The LumTerminate standard functions, for example, include:

killing the background task;

freeing memory; and/or calling an instrument terminate function.

LumSet Bead Map File Component

A LumSet Bead Map File component means 735, or function, such as shown in FIG. 44, loads a file, which defines, for example, a two-dimensional bead map used to distinguish one bead type from another, i.e., beads of one bead subset from those of another. Optionally, the LumSet Bead Map File component 735 is a LumAPI function. By way of example, if only one fluorescent dye is used per bead type, a one-dimension bead map is used.

LumReset User Beads Component

A LumReset User. Beads component means 740, or function, for example as shown in FIG. 44, is the first function called when a user is defining which beads an assay will be using. Optionally, the LumReset User Beads component 740 is a LumAPI function. The LumReset User Beads function 740, for example, resets an internal table, of user beads in the LumAPI library 705.

Optionally, a user makes repeated calls to a LumSet User Beads function 745 to build a list of bead types needed for an assay. Alternatively, in an alternative embodiment of the function, the user makes a single call to the LumReset User Beads function 740 to build the list of needed bead types. Optionally, the LumReset User Beads function 740 is omitted if, for example, the LumSet User Bead function 745 discussed hereinbelow, can write over values stored in the LumAPI's table of needed bead types.

LumSet User Bead Component

A LumSet User Bead component means 745, or function, such as shown in FIG. 44, informs the LumAPI library 705 that a user will be interested in acquiring bead statistics for a bead by a unique identifier associated with the given bead type. Optionally, the LumSet User Bead Component 745 is a LumAPI function.

The user, for example, makes repeated calls to the LumSet User Bead function 745 to add additional beads to the list of interested bead types. In an alternative embodiment, the user makes a single call to the LumSet User Bead function 745, add additional beads to the list of interested bead types. The user, as discussed above, calls the LumReset User Beads function 740 prior to calling the LumSet User Beads function 745 to clear the internal list of beads. Optionally, a parameter in the LumSet User Bead function 745 includes a user-supplied literal to be associated with the given bead type.

DSP Control and Monitoring Components

LumRead Panel Settings Component

A LumRead Panel Settings component means 750, or function, such as shown in FIG. 44, copies a current set of flow analyzer settings into a user-supplied buffer. Optionally, the LumRead Panel Settings component 750 indicates which, if any, of the settings have changed since a previous call to the LumRead Panel Settings function 750.

LumChange Panel Settings Component

A LumChange Panel Settings component means 755, or function, such as shown in FIG. 44, allows a user to change one or more flow analyzer settings at a time. The settings in a user-supplied buffer, which holds the desired panel settings, are optionally modified beginning with the first parameter in the supplied settings which needs changing and ending with the last parameter in the supplied settings which needs changing.

Sample Acquisition and Result Reporting Components

LumStart Test Component

A LumStart Test component means 760, or function, such as shown in FIG. 44, tells the LumAPI library 705 to begin acquiring bead statistics for the current sample loaded on the flow analyzer using, for example, a background task. Prior to calling the LumStart Test function 760, the sample fluid to be analyzed is loaded into the flow analyzer, and the flow analyzer is placed in the RUN mode. Alternatively, the sample fluid loading and flow analyzer running is automatically operated by the instant software, either by the LumStart Test component 760 or an operatively linked function.

LumStop Test Component

A LumStop Test component means 765, or function, such as shown in FIG. 44, ends the acquiring of bead statistics for the current sample.

LumQuery Test Results Component

A LumQuery Test Results component means 770, or function, such as shown in FIG. 44, copies the most current bead statistics into a user-supplied buffer. Bead statistics are contained, for example, in a user-supplied table of test result-data structures. The table is large enough to store, for example, less than 100 test result data structures, 100 such data structures, or more than 100 such data structures.

The LumQuery Test Results component 770 is called at any time after the LumStart Test component 760 is called to get substantially immediate statistics prior to collecting all of the requested beads. In an alternate embodiment, the LumQuery Test Results component 770 is called prior to or concurrently with the LumStart Test component 760, provided that the LumQuery Test Results component 770 includes a trigger component. That is, the LumQuery Test Results component 770 is optionally dormant, until operation of the LumStart Test component. 760 triggers activity of the LumQuery Test Results component 770.

LumQuery Test Total Component

A LumQuery Test Total component means 775, or function, such as shown in FIG. 44, returns data acquisition statistics.

I have recognized that near-maximal levels of target molecules are not optimal for all assays, depending on the desired properties. For example, capture/sandwich assays are more sensitive with high levels of capture molecules per bead than with high levels of target molecules per bead. As another example, I have determined that inhibition assays are more sensitive with limiting amounts of capture molecules per bead than high levels of capture molecules per bead.

As to reporter labeling, I have recognized that amine-reactive derivatives, for example, of green fluorescent dyes, for example, are well-suited for labeling reporter molecules. Optionally, the same dye is used for all assays multiplexed together. Alternatively, different dyes are used for one or more of the assays multiplexed together. By way of example, fluorescent reporter molecules are prepared by substitution with, for instance, green fluorescent dyes. The BODIPY® dye by Molecular Probes, Inc., for example, is an acceptable green dye for use in assays, according to the instant invention, and, in particular, for preparation of reporter molecules. Alternatively, fluoroscein-labeled reporter groups are also used with a higher spectral overlap compensation setting for "bleed" into, for example, the orange channel than required for BODIPY®-labeled reporter groups. For example, whereas an FL2-%FL1 compensation for BODIPY® is, for instance, set to approximately 20, an FL2-%FL1 compensation for fluoroscein is, for instance, set to approximately 34. FL2-%FL1 compensation for any other green dye, for example, is determined empirically by measuring the percent of any spectral overlap of the green fluorescence (FL1) channel, for example, into the orange fluorescence (FL2) channel, for example, using standard assay development beads.

By way of illustration, virtually any protein or peptide can be labeled using the BODIPY-FL-CASE dye by Molecular Probes, Inc. Proteins or peptides can also be labeled with fluorescein derivatives, such as fluoroscein isothiocynate (FITC). Synthetic oligonucleotides of, for example, 15 to 40 bases can be successfully used for hybrization assays consistent with the instant invention. Oligonucleotides having more than two bases but less than 15 bases, or greater than 40 bases are also acceptable. For example, complementary A and B strands are required for each genetic sequence to be analyzed. That is, one strand is coupled to the target beads, and the other strand is conjugated to, for example, a green fluorescent reporter dye. For example, each oligonucleotide includes a standard spacer and/or linker between the terminal nucleotide and the amino group. To this extent, for example, a C9-spacer and, for example, a C6-amino-terminal linker are used during synthesis. The synthesis, for instance, results in a total length of, for example, approximately fifteen atoms. Fewer or more atoms in the spacer are also permitted. However, for instance, a total spacer instance of less than twelve atoms reduces the performance of the hybridization assays. Oligonucleotides are connected during synthesis, for example, either at the 3' or the 5' end. I have recognized that 5' connections are usually less expensive than 3' connections.

In general, the concentration of target molecules per bead used in the bead coupling reaction are optimized, for example, by filtration in the same way that a coating of a microfilter plate is optimized. Optional concentrations of reporter molecules per bead are determined, for example, by filtration with a fixed number of beads. Optionally, the extent of fluorescent labeling of these molecules are also varied.

I have determined that the number of beads used in an assay affect the amount of target molecules present and/or the analysis time on the flow analyzer. Specifically, I recognized that greater numbers of beads result in more sensitive assays. Using, for example, 1,000 to 10,000 beads per assay allows for analysis in, for example, less than one second, one second, two seconds, three seconds, or up to a minute. However, the number of beads is optionally increased or decreased to improve sensitivity or decrease run time, as desired.

Assay conditions for assays according to the instant invention, for example, are similar to conditions for reactions performed in other standard formats. That is, for example, immunoassays are performed in, for example, a buffer which limits non-specific binding, such as PBS containing approximately 0.1% BSA. As another example, hybridization of nucleic acids are performed in most standard hybridization buffers. When complex mixtures of sequences with disparate guanine and cytosine pairs are present in multiplexed assays, a buffer system, such as tetramethyl ammonium chloride (TeMAC), which minimizes differences in melting points are used advantageously. Because guanine and cytosine pairs include three hydrogen bonds between the bases, and adenine and thymine pairs include two hydrogen pairs, a DNA strand having a higher concentration of guanine and cytosine pairs than adenine and thiamine pairs will have a higher melting point than vice versa.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

GLOSSARY

API Application Program Interface, a set of functions usually in a separate library which the calling program can use.

Bead see Microsphere

Channel Channel can have two similar but separate meanings. A channel normally is synonymous to any PMT reading associated with a given light scattering event. Thus as an object passes through the laser, multiple channels report their readings including Forward Scatter, Side Scatter, FL1, FL2 and FL3.

The alternate meaning refers to the form of data associated with a channel. For the FACScan, channel data is reported as a 10 bit reading, thereby producing a number from 0 to 1023, or 1024 different "channels". The application has the option of reporting the data in its raw form of "channel data" or in a logarithmic mode from 0 to $10^4 -1$. For example, if the documentation describes something as having "only 10 channels of difference," then it is referring to the data for a given channel as it comes into the computer and not to different PMTs.

Doublet A clumping of two or more microspheres. Doublets produce more scattered light signal than single beads and thus can lead to incorrect analysis. Doublets are rejected from analysis by employing a side scatter gate.

DSP Digital signal processor. It is a standard computer processor chip capable of very fast mathematical operations.

FL1 Fluorescence channel one. It is designed to capture only light of a given color, e.g., green. The light first passes through a wavelength filter and is then collected on the FL1 PMT.

FL2 Fluorescence channel two. It is designed to capture only light of a given color, e.g., orange. The light first passes through a wavelength filter and is then collected on the FL2 PMT.

FL3 Fluorescence channel three. It is designed to capture only light of a given color, e.g., red. The light first passes through a wavelength filter and is then collected on the FL3 PMT.

Forward Scatter This refers to the amount of light passing directly through the patient's sample at a given instance. Forward scatter normally provides a measurement for the size of an object passing through the laser beam.

GAM Refers to a test of IgG, IgA and IgM human antibodies. These antibodies are usually present to attach themselves to an infectious agent present in the body so that it is later destroyed.

Gating Gating refers to a method of filtering out events by the application. For purposes of the instant invention, gating involves only allowing events, which belong to a narrow, predefined range in the side scatter channel. This ensures only objects of the size of a single microsphere are collected.

GUI Graphical User Interface, a program that is used to interface to the operator.

IgG The IgG antibody shows up after the IgM antibody and will adapt to provide lifelong immunity to an infectious agent.

IgA The IgA antibody is normally found in the salivary glands.

IgM The human IgM antibody is normally the first antibody to attack an infection and will be present for the first two weeks of an infection.

Microsphere Precisely manufactured 5.5 micron diameter spheres with a tolerance of ±0.1 micron. Spheres of other sizes are acceptable.

MIF Mean Intensity of Fluorescence (a.k.a. MFI—Mean Fluorescence Intensity)

PMT Photo multiplier tube. Located inside the flow cytometer, it amplifies low levels of light and provides a method for digital conversion. A given wavelength of light can be measured by supplying a light filter.

Sheath Fluid A relatively rapid stream consisting of what is usually highly filtered water. By having the sheath fluid flow much faster than the injected patient sample, the patient sample drawn toward the center of the combined streams. This enables the patient sample to pass through the center of the focused laser beam.

Side Scatter This refers to the amount of light that has been deflected at a right angle to the direction of the laser beam. Side scatter provides an alternate measurement of the relative size and shape of the object passing through the laser beam.

Singlets A single microsphere, one which is not attached to another microsphere. See doublets.

What is claimed is:

1. A multi-analyte diagnostic system for use with a computer, the system comprising:

a flow analyzer including a substantially co-planar optical assembly having a plurality of light sources and at least four optical detectors, said plurality of light sources including overlapping focal regions, and said flow analyzer being communicatable with the computer; and a memory medium readable by the computer and storing computer software, the software including instructions for causing the computer to perform the steps of:
    processing a biological sample using said flow analyzer, and
    determining a presence and quantity of at least one analyte of interest in the biological sample substantially simultaneously to said processing step;
    wherein said flow analyzer further includes a cuvette having a flat air-to-glass interface; said cuvette includes a neck-up region having a hexagonal cross-section; and two of the plurality of light sources are respectively configured to emit two distinct wavelengths of light.

2. The multi-analyte diagnostic system of claim 1, wherein said cuvette includes a neck-up region having a regular polygonal cross-section wherein opposite sides are parallel and have a flat air to surface interface relative to each of said light sources and said optical detectors and wherein the number of sides is at least 6.

3. A multi-analyte diagnostic system for use with a computer, the system comprising:

a flow analyzer including a substantially co-planar optical assembly having a plurality of light sources and a plurality of optical detectors, said plurality of light sources including overlapping focal regions, and said flow analyzer being communicatable with the computer; and a memory medium readable by the computer and storing computer software, the software including instructions for causing the computer to perform the steps of:
    processing a biological sample using said flow analyzer, and
    determining a presence and quantity of at least one analyte of interest in the biological sample substantially simultaneously to said processing step;
    wherein said flow analyzer includes one of a multi-pass filter and a plurality of bandpass filters coupled in parallel to at least one of said plurality of optical detectors via a respective multi-mode cable.

4. The diagnostic system according to claim 3, wherein said flow analyzer includes, for each band-pass filter, an amplifying photo-detector and an analog-to-digital converter connected in series thereto.

5. The diagnostic system according to claim 4, wherein said amplifying photo-detector includes one of a photomultiplier tube, an avalanche photo-diode, and a p-i-n photo-diode.

6. The diagnostic system according to claim 4, wherein said flow analyzer includes for each band-pass filter, an inverting amplifier in series with a low pass Nyquist filter, connected between said amplifying photo-detector and said analog-to-digital converter.

7. The diagnostic system according to claim 3, further comprising a digital interface board connectable to the computer and to said flow analyzer.

8. The diagnostic system according to claim 7, wherein said digital interface board includes:
- a microcontroller in communication with said flow analyzer, and
- a digital signal processor in communication with said microcontroller and each analog-to-digital converter.

9. The diagnostic system according to claim 8, wherein said analog-to-digital converter includes a circular memory buffer having a first movable pointer, a second movable pointer, and a plurality of storage positions, said first pointer pointing to an oldest storage position into which new sample data may be stored, said second pointer pointing to a storage position from which said digital signal processor analyzes old sample data stored therein.

10. The diagnostic system according to claim 9 wherein said flow analyzer includes a cuvette, a sample pump communicating with said microcontroller and connected to said cuvette, and a sheath fluid reservoir communicating with said microcontroller and connected to said cuvette.

11. The diagnostic system according to claim 10, wherein said flow analyzer includes a waste receptacle, said microcontroller upon assay completion, communicating with said sample pump to one of halt sample fluid flow and to divert any remaining sample to said waste receptacle, and communicating with said sheath fluid reservoir to one of halt sheath fluid flow and divert any remaining sheath fluid to said waste receptacle.

12. The diagnostic system according to claim 4, wherein said flow analyzer includes a single-filter light path from each optical detector to each amplifying photo-detector.

* * * * *